(12) United States Patent
Black et al.

(10) Patent No.: US 7,371,747 B2
(45) Date of Patent: May 13, 2008

(54) CYANOALKYLAMINO DERIVATIVES AS PROTEASE INHIBITORS

(75) Inventors: Cameron Black, Baie d'Urfe (CA); Sheldon N. Crane, Rue D'Amalfi (CA); Dana Davis, Santa Clara, CA (US); Eduardo L. Setti, San Mateo, CA (US)

(73) Assignee: Merck Frosst Canada & Co., Quebec (CA)

( * ) Notice: Subject to any disclaimer, the term of this patent is extended or adjusted under 35 U.S.C. 154(b) by 650 days.

(21) Appl. No.: 10/495,387

(22) PCT Filed: Nov. 13, 2002

(86) PCT No.: PCT/US02/36352

§ 371 (c)(1),
(2), (4) Date: May 11, 2004

(87) PCT Pub. No.: WO03/041649

PCT Pub. Date: May 22, 2003

(65) Prior Publication Data

US 2005/0014941 A1    Jan. 20, 2005

Related U.S. Application Data

(60) Provisional application No. 60/351,316, filed on Nov. 13, 2001.

(51) Int. Cl.
*A61K 31/535*    (2006.01)

(52) U.S. Cl. .............................. 514/231.5; 514/252.13; 514/277; 514/449; 514/520; 544/158; 544/159; 544/383; 544/392; 544/393; 546/262; 546/265; 549/491; 558/190; 558/391; 558/392; 558/436; 558/445

(58) Field of Classification Search ................ 544/158, 544/159, 383, 392, 393; 546/262, 265; 549/491; 558/190, 391, 392, 436, 445
See application file for complete search history.

(56) References Cited

FOREIGN PATENT DOCUMENTS

WO    WO 00/55125    9/2000

*Primary Examiner*—Johann Richter
*Assistant Examiner*—Ebenezer Sackey
(74) *Attorney, Agent, or Firm*—Nicole A. Beeler; David A. Muthard

(57) ABSTRACT

The present invention is directed to novel cyanoalkylamino derivatives that are inhibitors of cysteine protease such as cathepsins K, S, B and L, in particular cathepsin K Pharmaceutical composition comprising these compounds, method of treating diseases mediated by unregulated cysteine protease activity, in particular cathepsin K utilizing these compounds and methods of preparing these compounds are also disclosed.

17 Claims, No Drawings

US 7,371,747 B2

CYANOALKYLAMINO DERIVATIVES AS PROTEASE INHIBITORS

CROSS-REFERENCE TO RELATED APPLICATIONS

This application claims priority to U.S. Provisional application Ser. No. 60/351,316, filed on Nov. 13, 2001, the disclosure of which is incorporated herein by reference in its entirety.

BACKGROUND OF THE INVENTION

1. Field of Invention

The present invention is directed to novel cyanoalkylamino derivatives that are inhibitors of cysteine protease such as cathepsins K, S, B and L, in particular cathepsin K. Pharmaceutical composition comprising these compounds, method of treating diseases mediated by unregulated cysteine protease activity, in particular cathepsin K, utilizing these compounds and methods of preparing these compounds are also disclosed.

2. State of the Art

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increase expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteoarthritis, *pneumocystis carinii*, acute pancreatitis, inflammatory airway disease and bone and joint disorders.

The prominent expression of cathepsin K in osteoclasts and osteoclast-related multinucleated cells and its high collagenolytic activity suggest that the enzyme is involved in osteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogeneic immune responses, including, but not limited to, rejection of organ transplants or tissue grafts.

In view of the number of diseases wherein it is recognized that an increase in cysteine protease activity contributes to the pathology and/or symptomatology of the disease, molecules which are shown to inhibit the activity of this class of enzymes, in particular molecules which are inhibitors of cathepsins B, K, L and/or S, will be useful as therapeutic agents.

SUMMARY OF THE INVENTION

In one aspect, the present invention is directed to a compound of Formula I:

$$\text{Ar---X}^1\text{---}\underset{R^4\ R^5}{\overset{R^6\ R^{6a}}{\diagdown\diagup}}\text{---}\underset{O}{\overset{R^3}{\diagdown}}\text{N---}\underset{R^1\ R^2}{\overset{}{\diagup}}\text{CN}$$ 
I wherein:
$X^1$ is —O—, —NR—, —S—, —S(O)— or —S(O)$_2$— where R is hydrogen, (C$_{1-6}$)alkyl, halo-substituted (C$_{1-6}$)alkyl, or aryl(C$_{1-6}$)alkyl;
$R^1$ is hydrogen or (C$_{1-6}$)alkyl;
$R^2$ is a group selected from hydrogen, (C$_{1-6}$)alkyl, halo-substituted (C$_{1-3}$)alkyl, —X$^2$NR$^7$R$^7$, —X$^2$NR$^7$C(O)R$^7$, —X$^2$C(O)NR$^7$R$^7$, —X$^2$NR$^7$C(O)OR$^7$, —X$^2$OC(O)NR$^7$R$^7$, —X$^2$NR$^7$C(O)NR$^7$R$^7$, —X$^2$NR$^7$C(NR$^7$)NR$^7$R$^7$, —X$^2$OR$^7$, —X$^2$C(O)R$^7$, —X$^2$C(O)OR$^7$, —X$^2$OC(O)R$^7$, —X$^2$S(O)$_2$NR$^7$R$^7$, —X$^2$P(O)(OR$^7$)OR$^7$, —X$^2$OP(O)(R$^7$)OR$^7$, —X$^2$SR$^7$, —X$^2$S(O)R$^8$, —X$^2$S(O)$_2$R$^8$, —X$^2$NR$^7$S(O)$_2$R$^8$, —X$^2$NR$^9$R$^{10}$, —X$^2$NR$^9$C(O)R$^{10}$, —X$^2$C(O)NR$^9$R$^{10}$, —X$^2$S(O)$_2$NR$^9$R$^{10}$, —X$^2$NR$^9$S(O)$_2$R$^{10}$, —X$^2$OC(O)NR$^9$R$^{10}$, —X$^2$NR$^9$C(O)NR$^9$R$^{10}$, —X$^2$NR$^9$C(NR$^9$)NR$^9$R$^{10}$, —R$^{10}$, —X$^2$OR$^{10}$, —X$^2$C(O)R$^{10}$, —X$^2$C(O)OR$^{10}$, —X$^2$OC(O)R$^{10}$, —X$^2$SR$^{10}$, —X$^2$S(O)R$^{10}$, and —X$^2$S(O)$_2$R$^{10}$, wherein:
$X^2$ is (C$_{1-6}$)alkylene or (C$_{2-6}$)alkenylene;
$R^7$ at each occurrence independently is hydrogen, (C$_{1-6}$)alkyl, or halo-substituted (C$_{1-3}$)alkyl;
$R^8$ is (C$_{1-6}$)alkyl or halo-substituted (C$_{1-3}$)alkyl;
$R^9$ is hydrogen or (C$_{1-6}$)alkyl; and
$R^{10}$ is —X$^3$R$^{11}$ wherein X$^3$ is a bond or (C$_{1-6}$)alkylene; and R$^{11}$ is either:
(i) (C$_{3-8}$)cycloalkyl;
(ii) (C$_{3-8}$)cycloalkenyl;
(iii) heterocycloalkyl;
(iv) heterocycloalkenyl;
(v) (C$_{6-14}$)aryl; or
(vi) heteroaryl;
wherein said cycloalkyl, cycloalkenyl, heterocycloalkyl or heterocycloalkenyl is optionally substituted with one to three groups independently selected from the group consisting of (C$_{1-6}$)alkyl, (C$_{1-6}$)alkylidene, (C$_{1-6}$)alkylimino, cyano, halo, halo-substituted (C$_{1-4}$)alkyl, imino, nitro, oxo, thioxo, —X$^3$NR$^7$R$^7$, —X$^3$NR$^7$C(O)R$^7$, —X$^3$C(O)NR$^7$R$^7$,
—X$^3$NR$^7$C(O)OR$^7$, —X$^3$OC(O)NR$^7$R$^7$, —X$^3$NR$^7$C(O)NR$^7$R$^7$, X$^3$NR$^7$C(NR$^7$)NR$^7$R$^7$, —X$^3$OR$^7$, —X$^3$C(O)R$^7$, —X$^3$C(O)OR$^7$, —X$^3$OC(O)R$^7$, —X$^3$S(O)$_2$NR$^7$R$^7$, —X$^3$P(O)(OR$^7$)OR$^7$, —X$^3$OP(O)(OR$^7$)OR$^7$, —X$^3$SR$^7$, —X$^3$S(O)R$^8$, —X$^3$S(O)$_2$R$^8$ and —X$^3$NR$^7$S(O)$_2$R$^8$; and
said aryl or heteroaryl is optionally substituted with one to three groups independently selected from the group consisting of (C$_{1-6}$)alkyl, cyano, halo, halo-substituted (C$_{1-4}$)alkyl, nitro, —X$^3$NR$^7$R$^7$, —X$^3$NR$^7$C(O)R$^7$, —X$^3$C(O)NR$^7$R$^7$,
—X$^3$NR$^7$C(O)OR$^7$, —X$^3$OC(O)NR$^7$R$^7$, —X$^3$NR$^7$C(O)NR$^7$R$^7$, —X$^3$NR$^7$C(NR$^7$)NR$^7$R$^7$, —X$^3$OR$^7$, —X$^3$C (O)R⁷, —X³C(O)OR⁷, —X³OC(O)R⁷, —X³S(O)₂ NR⁷R⁷, —X³P(O)(OR⁷)OR⁷, —X³OP(O)(OR⁷)R⁷, —X³SR⁷, —X³S(O)R⁸, —X³S(O)₂R⁸ and —X⁷NR⁷S (O)₂R⁸ wherein X³, R⁷ and R⁸ are as defined above; or R¹ and R² together with the carbon atoms to which R¹ and R² are attached form (C₃₋₈)monocyclic cycloalkylene or monocyclic heterocycloalkylene;

R³ is hydrogen or (C₁₋₆)alkyl;

R⁶ and R⁶ᵃ together with the carbon atoms to which they are attached form:
(i) (C₃₋₇)monocyclic cycloalkylene;
(ii) (C₇₋₈) bridged polycyclic cycloalkylene;
(iii) (C₃₋₇)monocyclic cycloalkenylene;
(iv) (C₇₋₈) bridged polycyclic cycloalkenylene;
(v) (C₇₋₈)spirocycloalkylene;
(vi) monocyclic heterocycloalkylene having three to seven ring atoms;
(vii) bridged polycyclic heterocycloalkylene having seven or eight ring atoms;
(viii) monocyclic heterocycloalkenylene having three to seven ring atoms;
(ix) bridged polycyclic heterocycloalkenylene having seven or eight ring atoms;
(x) phenylene; or
(xi) heteroarylene having five or six ring atoms; and further wherein said monocyclic or bridged cycloalkylene, monocyclic or bridged cycloalkenylene, monocyclic or bridged heterocycloalkylene, or monocyclic or bridged heterocycloalkenylene ring is optionally substituted with one, two or three groups independently selected from the group consisting of (C₁₋₃)alkyl, hydroxy, fluoro, chloro, and oxo and said phenylene or heteroarylene ring is optionally substituted with one or two groups independently selected from the group consisting of methyl, chloro, fluoro, and bromo;

R⁴ and R⁵ independently hydrogen, fluoro, (C₁₋₆)alkyl or R⁴ and R⁵ together with the carbon atoms to which they are attached form —(C₃₋₆)monocyclic cycloalkylene or monocyclic heterocycloalkylene having three to six ring atoms; and Ar is selected from the group consisting of:
(i) —(C₀₋₃)alkylene-Ar¹ where Ar¹ is (C₆₋₁₂)aryl, heteroaryl, heterocycloalkyl, or heterocycloalkenyl;
(ii) —(C₀₋₃)alkylene-Ar¹—X⁴—Ar² where Ar¹ is as defined above;
(iii) —(C₀₋₃)alkylene-Ar¹—X⁴—Ar²—X⁵—Ar³ where Ar¹ is as defined above; and
(iv) —(C⁰⁻³)alkylene-Ar¹—X⁴—Ar²—X⁵—Ar³—X⁶—Ar⁴ where Ar¹ is as defined above;

wherein:
X⁴, X⁵ and X⁶ are independently selected from the group consisting of a bond, (C₁₋₆)alkylene, —X⁷NR¹⁵X⁸—, —X⁷NR¹⁵C(O)X⁸—, —X⁷C(O)NR¹⁵X⁸, —X⁷NR¹⁵C(O)OX⁸—, —X⁷OC(O) NR¹⁵X⁸—, —X⁷NR¹⁵C(O)NR¹⁵X⁸—, —X⁷NR¹⁵C(NR¹⁵) NR¹⁵X⁸—, —X⁷OX⁸—, —X⁷C(O)X⁸—, —X⁷C(O)OX⁸—, —X⁷OC(O)X⁸—, —X⁷S(O)₂NR¹⁵X⁸—, —X⁷SX⁸—, —X⁷S(O)X⁸—, —X⁷S(O)₂X⁸—, —X⁷NR¹⁵S(O)₂X⁸—, and heteroalkylene, and X⁴ and X⁷ can additionally be (C₂₋₆)alk-1-ynyl, wherein X⁷ and X⁸ independently are a bond or (C₁₋₆)alkylene and each R¹⁵ is hydrogen or (C₁₋₆) alkyl; and Ar², Ar³ and Ar⁴ are independently selected from the group consisting of:
(i) (C₃₋₈)cycloalkyl;
(ii) (C₃₋₈)cycloalkenyl;
(iii) heterocycloalkyl;
(iv) heterocycloalkenyl;
(v) (C₆₋₁₄)aryl; and
(vi) heteroaryl;
provided that only one of Ar¹, Ar², Ar³, and Ar⁴ can be cycloalkyl, cycloalkenyl, heterocycloalkyl, heterocycloalkenyl, aryl or heteroaryl having more than six ring atoms;

and furthermore when Ar¹, Ar², Ar³, and Ar⁴ is cycloalkyl, cycloalkenyl, heterocycloalkyl or heterocycloalkenyl it is optionally substituted with one, two, or three groups independently selected from the group consisting of (C₁₋₆)alkyl, (C₁₋₆)alkylidene, (C₁₋₆)alkylimino, cyano, halo, halo-substituted (C₁₋₄)alkyl, imino, nitro, oxo, thioxo, —X⁹NR¹⁶R¹⁶, —X⁹NR¹⁶C(O)R¹⁶, —X⁹C(O) NR¹⁶R¹⁶, —X⁹NR¹⁶C(O)OR¹⁶, —X⁹OC(O)NR¹⁶R¹⁶, —X⁹NR¹⁶C(O)NR¹⁶R¹⁶, —X⁹NR¹⁶C(NR¹⁶) NR¹⁶R¹⁶, —X⁹OR¹⁶, —X⁹C(O)R¹⁶, —X⁹C(O)OR¹⁶, —X⁹OC(O)R¹⁶, —X⁹S(O)₂NR¹⁶R¹⁶, —X⁹P(O) (OR¹⁶)OR¹⁶, —X⁹OP(O)(OR¹⁶)OR¹⁶, —X⁹SR¹⁶, —X⁹S(O)R¹⁷, —X⁹S(O)₂R¹⁷, and —X⁹NR¹⁶S(O)₂ R¹⁷, wherein X⁹ is a bond, (C₁₋₆)alkylene, or (C₂₋₆)alk-1-ynyl, R¹⁶ at each occurrence independently is hydrogen, (C₁₋₆)alkyl, or halo-substituted (C₁₋₃)alkyl, and R¹⁷ is (C₁₋₆)alkyl or halo-substituted (C₁₋₃)alkyl; and when Ar¹, Ar², Ar³, and Ar⁴ is aryl or heteroaryl it is optionally substituted with one, two, or three groups independently selected from the group consisting of (C₁₋₆)alkyl, cyano, halo, halo-substituted (C₁₋₄)alkyl, nitro, —X⁹NR¹⁶R¹⁶, —X⁹NR¹⁶C(O)R¹⁶, —X⁹C(O) NR¹⁶R¹⁶, —X⁹NR¹⁶C(O)OR¹⁶, —X⁹OC(O)NR¹⁶R¹⁶, —X⁹NR¹⁶C(O)NR¹⁶R¹⁶—X⁹NR¹⁶C(NR¹⁶)NR¹⁶R¹⁶, —X⁹OR¹⁶—X⁹C(O)R⁶, —X⁹C(O)OR¹⁶, —X⁹OC(O) R¹⁶, —X⁹S(O)₂NR¹⁶R¹⁶, —X⁹P(O)(OR¹⁶)OR¹⁶, —X⁹OP(O)(OR¹⁶)OR¹⁶, —X⁹SR¹⁶, —X⁹S(O)R¹⁷, —X⁹S(O)₂R¹⁷, —OS(O)₂R¹⁷, —X⁹NR¹⁶S(O)₂R¹⁷, and heteroalkyl wherein X⁹ is a bond or (C₁₋₆)alkylene, R¹⁶ at each occurrence independently is hydrogen, (C₁₋₆)alkyl, or halo-substituted (C₁₋₃)alkyl, and R¹⁷ is (C₁₋₆)alkyl, or halo-substituted (C₁₋₃)alkyl; and individual isomers and mixtures of isomers; and pharmaceutically acceptable salts thereof provided that there are no more than 5 ring systems in a compound of Formula I.

In a class, a compound of Formula I:

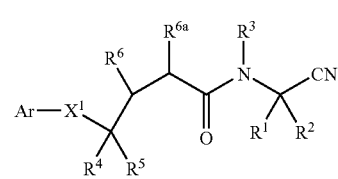

I wherein:
X¹ is —O—, —NR—, —S—, —S(O)— or —S(O)₂— where R is hydrogen or (C₁₋₆)alkyl;

R¹ is hydrogen or (C₁₋₆)alkyl;

R² is a group selected from hydrogen, (C₁₋₆)alkyl, halo-substituted (C₁₋₃)alkyl, —X²NR⁷R⁷, —X²NR⁷C(O)R⁷, —X²C(O)NR⁷R⁷, —X²NR⁷C(O)OR⁷, —X²OC(O)NR⁷R⁷, —X²NR⁷C(O)NR⁷R⁷, —X²NR⁷C(NR⁷)NR⁷R⁷, —X²OR⁷, —X²C(O)R⁷, —X²C(O)OR⁷, —X²OC(O)R⁷, —X²S(O)₂ NR⁷R⁷, —X²P(O)(OR⁷)OR⁷, —X²OP(O)(OR⁷)OR⁷, —X²SR⁷, —X²S(O)R⁸, —X²S(O)₂R⁸, —X²NR⁷S(O)₂R⁸, —$X^2NR^9R^{10}$, —$X^2NR^9C(O)R^0$, —$X^2C(O)NR^9R^{10}$, —$X^2S(O)_2NR^9R^{10}$, —$X^2NR^9S(O)_2R^{10}$, —$X^2OC(O)NR^9R^{10}$, —$X^2NR^9C(O)NR^9R^{10}$, —$X^2NR^9C(NR^9)NR^9R^{10}$, —$R^{10}$, —$X^2OR^{10}$, —$X^2C(O)R^{10}$, —$X^2C(O)OR^{10}$, —$X^2OC(O)R^{10}$, —$X^2SR^{10}$, —$X^2S(O)R^{10}$, and —$X^2S(O)_2R^{10}$, wherein:

$X^2$ is $(C_{1-6})$alkylene or $(C_{2-6})$alkenylene;

$R^7$ at each occurrence independently is hydrogen, $(C_{1-6})$alkyl, or halo-substituted $(C_{1-3})$alkyl;

$R^8$ is $(C_{1-6})$alkyl or halo-substituted $(C_{1-3})$alkyl;

$R^9$ is hydrogen or $(C_{1-6})$alkyl; and $R^{10}$ is —$X^3R^{11}$ wherein $X^3$ is a bond or $(C_{1-6})$alkylene; and $R^{11}$ is either:

(i) $(C_{3-8})$cycloalkyl;
(ii) $(C_{3-8})$cycloalkenyl;
(iii) heterocycloalkyl;
(iv) heterocycloalkenyl;
(v) $(C_{6-14})$aryl; or
(vi) heteroaryl;

wherein said cycloalkyl, cycloalkenyl, heterocycloalkyl or heterocycloalkenyl is optionally substituted with one to three groups independently selected from the group consisting of $(C_{1-6})$alkyl, $(C_{1-6})$alkylidene, $(C_{1-6})$alkylimino, cyano, halo, halo-substituted $(C_{1-4})$alkyl, imino, nitro, oxo, thioxo, —$X^3NR^7R^7$, —$X^3NR^7C(O)R^7$, —$X^3C(O)NR^7R^7$, —$X^3NR^7C(O)OR^7$, —$X^3OC(O)NR^7R^7$, —$X^3NR^7C(O)NR^7R^7$, —$X^3NR^7C(NR^7)NR^7R^7$, —$X^3OR^7$, —$X^3C(O)R^7$, —$X^3C(O)OR^7$, —$X^3OC(O)R^8$, —$X^3S(O)_2NR^7R^7$, —$X^3P(O)(OR^7)OR^7$, —$X^3OP(O)(OR^7)OR^7$, —$X^3SR^7$, —$X^3S(O)R^8$, —$X^3S(O)_2R^8$ and —$X^3NR^7S(O)_2R^8$; and said aryl or heteroaryl is optionally substituted with one to three groups independently selected from the group consisting of $(C_{1-6})$alkyl, cyano, halo, halo-substituted $(C_{1-4})$alkyl, nitro, —$X^3NR^7R^7$, —$X^3NR^7C(O)R^7$, —$X^3C(O)NR^7R^7$, —$X^3NR^7C(O)OR^7$, —$X^3OC(O)NR^7R^7$, —$X^3NR^7C(O)NR^7R^7$, —$X^3NR^7C(NR^7)NR^7R^7$, —$X^3OR^7$, —$X^3C(O)R^7$, —$X^3C(O)OR^7$, —$X^3OC(O)R^7$, —$X^3S(O)_2NR^7R^7$, —$X^3P(O)(OR^7)OR^7$, —$X^3OP(O)(OR^7)OR^7$, —$X^3SR^7$, —$X^3S(O)R^8$, —$X^3S(O)_2R^8$ and —$X^3NR^7S(O)_2R^8$ wherein $X^3$, $R^7$ and $R^8$ are as defined above; or $R^1$ and $R^2$ together with the carbon atoms to which $R^1$ and $R^2$ are attached form $(C_{3-8})$monocyclic cycloalkylene or monocyclic heterocycloalkylene;

$R^3$ is hydrogen or $(C_{1-6})$alkyl;

$R^6$ and $R^{6a}$ together with the carbon atoms to which they are attached form:

(i) $(C_{3-7})$monocyclic cycloalkylene;
(ii) $(C_{7-8})$ bridged polycyclic cycloalkylene;
(iii) $(C_{3-7})$monocyclic cycloalkenylene;
(iv) $(C_{7-8})$ bridged polycyclic cycloalkenylene;
(v) monocyclic heterocycloalkylene having three to seven ring atoms;
(vi) bridged polycyclic heterocycloalkylene having seven or eight ring atoms;
(vii) monocyclic heterocycloalkenylene having three to seven ring atoms;
(viii) bridged polycyclic heterocycloalkenylene having seven or eight ring atoms;
(ix) phenylene; or
(x) heteroarylene having five or six ring atoms; and further wherein said monocyclic or bridged cycloalkylene, monocyclic or bridged cycloalkenylene, monocyclic or bridged heterocycloalkylene, or monocyclic or bridged heterocycloalkenylene ring is optionally substituted with one to two groups independently selected from the group consisting of $(C_{1-3})$alkyl, hydroxy, and oxo and said phenylene or heteroarylene ring is optionally substituted with one or two groups independently selected from the group consisting of methyl, chloro, fluoro, and bromo;

$R^4$ and $R^5$ independently hydrogen, fluoro, $(C_{1-6})$alkyl or $R^4$ and $R^5$ together with the carbon atoms to which they are attached form —$(C_{3-6})$monocyclic cycloalkylene or monocyclic heterocycloalkylene having three to six ring atoms; and Ar is selected from the group consisting of:

(i) —$(C_{0-3})$alkylene-$Ar^1$ where $Ar^1$ is $(C_{6-12})$aryl, heteroaryl, heterocycloalkyl, or heterocycloalkenyl;

(ii) —$(C_{0-3})$alkylene-$Ar^1$—$X^4$—$Ar^2$ where $Ar^1$ is as defined above;

(iii) —$(C_{0-3})$alkylene-$Ar^1$—$X^4$—$Ar^2$—$X^5$—$Ar^3$ where $Ar^1$ is as defined above; and (iv) —$(C^{0-3})$alkylene-$Ar^1$—$X^4$—$Ar^2$—$X^5$—$Ar^3$—$X^6$—$Ar^4$ where $Ar^1$ is as defined above;

wherein:

$X^4$, $X^5$ and $X^6$ are independently selected from the group consisting of a bond, —$(C_{1-6})$alkylene, —$X^7NR^{15}X^8$—, —$X^7NR^{15}C(O)X^8$—, —$X^7C(O)NR^{15}X^8$—, —$X^7NR^{15}C(O)OX^8$—, —$X^7OC(O)NR^{15}X^8$—, —$X^7NR^{15}C(O)NR^{15}X^8$—, —$X^7NR^{15}C(NR^{15})NR^{15}X^8$—, —$X^7OX^8$—, —$X^7C(O)X^8$—, —$X^7C(O)OX^8$—, —$X^7OC(O)X^8$—, —$X^7S(O)_2NR^{15}X^8$—, —$X^7SX^8$—, —$X^7S(O)X^8$—, —$X^7S(O)_2X^8$— and —$X^7NR^{15}S(O)_2X^8$—, wherein $X^7$ and $X^8$ independently are a bond or —$(C_{1-6})$alkylene and $R^{15}$ is hydrogen or $C_{1-6}$alkyl; and $Ar^2$, $Ar^3$ and $Ar^4$ are independently selected from the group consisting of:

(i) $(C_{3-8})$cycloalkyl;
(ii) $(C_{3-8})$cycloalkenyl;
(iii) heterocycloalkyl;
(iv) heterocycloalkenyl;
(v) $(C_{6-14})$aryl; and
(vi) heteroaryl;

provided that only one of $Ar^1$, $Ar^2$, $Ar^3$, and $Ar^4$ can be cycloalkyl, cycloalkenyl, heterocycloalkyl, heterocycloalkenyl, aryl or heteroaryl having more than six ring atoms;

and furthermore when $Ar^1$, $Ar^2$, $Ar^3$, and $Ar^4$ is cycloalkyl, cycloalkenyl, heterocycloalkyl or heterocycloalkenyl it is optionally substituted with one, two, or three groups independently selected from the group consisting of $(C_{1-6})$alkyl, $(C_{1-6})$alkylidene, $(C_{1-6})$alkylimino, cyano, halo, halo-substituted $(C_{1-4})$alkyl, imino, nitro, oxo, thioxo, —$X^9NR^{16}R^{16}$, —$X^9NR^{16}C(O)R^{16}$, —$X^9C(O)NR^{16}R^{16}$, —$X^9NR^{16}C(O)OR^{16}$, —$X^9OC(O)NR^{16}R^{16}$, —$X^9NR^{16}C(O)NR^6R^{16}$, —$X^9NR^{16}C(NR^{16})NR^{16}R^{16}$, —$X^9OR^{16}$, —$X^9C(O)R^{16}$, —$X^9C(O)OR^{16}$, —$X^9OC(O)R^{16}$, —$X^9S(O)_2NR^{16}R^{16}$, —$X^9P(O)(OR^{16})OR^{16}$, —$X^9OP(O)(OR^{16})OR^{16}$, —$X^9SR^{16}$, —$X^9S(O)R^{17}$, —$X^9S(O)_2R^{17}$ and —$X^9NR^7S(O)_2R^{17}$, wherein $X^9$ is a bond or $(C_{1-6})$alkylene, $R^{16}$ at each occurrence independently is hydrogen, $(C_{1-6})$alkyl, or halo-substituted $(C_{1-3})$alkyl, and $R^{17}$ is $(C_{1-6})$alkyl or halo-substituted $(C_{1-3})$alkyl; and when $Ar^1$, $Ar^2$, $Ar^1$ and $Ar^4$ is aryl or heteroaryl it is optionally substituted with one, two, or three groups independently selected from the group consisting of $(C_{1-6})$alkyl, cyano, halo, halo-substituted $(C_{1-4})$alkyl, nitro, —$X^9NR^{16}R^{16}$, —$X^9NR^{16}C(O)R^{16}$, —$X^9C(O)NR^{16}R^{16}$, —$X^9NR^{16}C(O)OR^{16}$, —$X^9OC(O)NR^{16}R^{16}$, $X^9NR^{16}C(O)NR^{16}R^{16}$, —$X^9NR^{16}C(NR^{16})NR^{16}R^{16}$, —$X^9OR^{16}$, —$X^9C(O)R^{16}$, —$X^9C(O)OR^{16}$, —$X^9OC(O)R^{16}$, —$X^9S(O)_2NR^{16}R^{16}$, —$X^9P(O)(OR^{16})OR^{16}$, —$X^9OP(O)(OR^{16})OR^{16}$, —$X^9SR^{16}$, —$X^9S(O)R^{17}$, —$X^9S(O)_2R^{17}$ and —$X^9NR^7S(O)_2R^{17}$, wherein $X^9$ is a bond or $(C_{1-6})$alkylene, $R^{16}$ at each occurrence independently is hydrogen, $(C_{1-6})$alkyl, or halo-substituted $(C_{1-3})$alkyl, and $R^{17}$ is $(C_{1-6})$alkyl, or halo-substituted $(C_{1-3})$alkyl; and individual isomers and mixtures of isomers; and pharmaceutically acceptable salts thereof provided that there are no more than 5 ring systems in a compound of Formula I.

In a second aspect, this invention is directed to a pharmaceutical composition comprising a compound of Formula I, individual isomer, mixture of isomers or pharmaceutically acceptable salt thereof in admixture with one or more pharmaceutically suitable excipients. The pharmaceutical composition comprising a compound of Formula I can additionally contain one or more active ingredient(s) selected from the group consisting of (i) a therapeutically effective amount of a bisphosphonic acid or an acid ester thereof or a pharmaceutically acceptable salt thereof and (ii) a therapeutically effective amount of an estrogen receptor agonist or a pharmaceutically acceptable salt thereof.

The bisphosphonic acid(s) used in the composition of the present invention is/are selected from the group consisting of 4-amino-1-hydroxybutylidene-1,1-bisphosphonic acid, 1,1-dichloromethylene-1,1-diphosphonic acid, 1-hydroxy-3-pyrrolidin-1-ylpropylidene-1,1-bisphosphonic acid, 1-hydroxyethylidene-1,1-diphosphonic acid, 1-hydroxy-3-(N-methyl-N-pentylamino)propylidene-1,1-bisphosphonic acid, 6-amino-1-hydroxyhexylidene-1,1-bisphosphonic acid, 3-(dimethylamino)-1-hydroxypropylidene-1,1-bisphosphonic acid, 3-amino-1-hydroxypropylidene-1,1-bisphosphonic acid, 2-pyrid-2-ylethylidene-1,1-bisphosphonic acid, 1-hydroxy-2-pyrid-3-ylethylidene-1,1-bisphosphonic acid, 4-chlorophenylthiomethylenebisphosphonic acid and 1-hydroxy-2-(1H-imidazol-1-yl)ethylidene-1,1-bisphosphonic acid or acid ester thereof or a pharmaceutically acceptable salt thereof.

An embodiment of this aspect includes pharmaceutical compositions comprising 4-amino-1-hydroxybutylidene-1,1-bisphosphonic acid or alendronate monosodium trihydrate or a pharmaceutically acceptable salt thereof.

In a third aspect, this invention is directed to a method of treating a disease in an animal in which inhibition of a cysteine protease, in particular cathepsin K, can prevent, inhibit or ameliorate the pathology and/or symptomatology of the disease, which method comprises administering to the animal a pharmaceutical composition comprising a therapeutically effective amount of compound of Formula I, an individual isomer, mixture of isomers or a pharmaceutically acceptable salt thereof. A preferred method is one wherein the disease is osteoporosis and the animal being treated is a human. Particularly preferred method comprises a post-menopausal woman as the animal being treated and wherein the cysteine protease is cathepsin K activity. The above method can also be carried out by administering to said human a pharmaceutical composition comprising a compounds of Formula I, an individual isomer, mixture of isomers or a pharmaceutically acceptable salt thereof in combination with one or more active ingredient(s) selected from the group consisting of (i) a therapeutically effective amount of a bisphosphonic acid or an acid ester thereof or a pharmaceutically acceptable salt thereof and (ii) a therapeutically effective amount of an estrogen receptor agonist or a pharmaceutically acceptable salt thereof. Preferable, bisphosphonic acids are 1,1-dichloromethylene-1,1-diphosphonic acid, 1,1-dichloromethylene-1,1-diphosphonate monosodium trihydrate or a pharmaceutically acceptable salt thereof.

In a fourth aspect, this invention is directed to an intermediate of Formula 4:

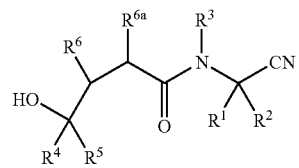

where A, $R^1$-$R^6$ and $R^{6a}$ are as defined in Formula I above. Preferable $R^1$-$R^5$, $R^6$ and $R^{6a}$ groups are as disclosed in the section titled "Classes of Embodiments" below.

In a fifth aspect, this invention is directed to an intermediate of Formula 5:

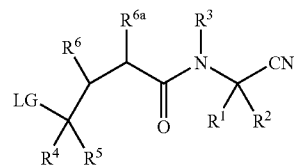

where A, $R^1$-$R^6$ and $R^{6a}$ are as defined in Formula I above and LG is a leaving group. Classes of $R^1$-$R^5$, $R^6$ and $R^{6a}$ groups are as disclosed in the section titled "Classes of Embodiments" below. In a class, the leaving group is chloro, bromo, iodo, mesylate, tosylate, or triflate.

In a sixth aspect, this invention is directed to the processes for preparing compounds of Formula I:

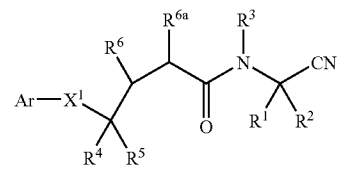

where Ar, $X^1$, $R^1$-$R^{6a}$ are as defined in the Summary of the Invention, which process comprises:

(A) reacting a compound of Formula 5:

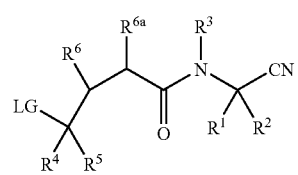

where LG is a leaving group and $R^1$-$R^{6a}$ are as defined in the Summary of the Invention with a compound of the formula Ar—$X^1$H, in which $X^1$ is —NR—, —O—, or —S— and R, and Ar are as defined in the Summary of the Invention;

(B) optionally converting a compound of Formula I obtained in Step A above, where $X^1$ is
—S— to a compound of Formula I where $X^1$ is either
—S(O)— or $S(O)_2$—;

(C) optionally converting a compound of Formula I into a pharmaceutically acceptable salt;

(D) optionally converting a salt form of a compound of Formula I to non-salt form;
(E) optionally separating individual isomers; and
(F) optionally modifying any of the $X^1$, Ar and $R^1$-$R^5$ groups.

The compounds prepared by the above process are those disclosed in section titled "Classes of Embodiments" below.

DETAILED DESCRIPTION OF THE INVENTION

Definitions:

Unless otherwise stated, the following terms used in the specification and claims are defined for the purposes of this application and have the meanings given this section:

"Alkyl" means a straight or branched, saturated aliphatic radical having one to six carbon atoms unless otherwise indicated e.g., $(C_{1-6})$alkyl includes methyl, ethyl, propyl, isopropyl, butyl, sec-butyl, isobutyl, tert-butyl, pentyl, hexyl, and the like. Preferably, methyl, ethyl, propyl, or isopropyl.

"Alkylene" means a straight or branched, saturated aliphatic divalent radical having one to six carbon atoms unless otherwise indicated e.g., $(C_{1-6})$alkylene includes methylene, ethylene, propylene, isopropylene, butylene, sec-butylene, isobutylene, tert-butylene, pentylene, hexylene, and the like. Preferably, $(C_{1-6})$alkylene includes methylene, ethylene, propylene, or isopropylene. When the term $(C_{0-3})$-alkylene is used, it includes a covalent bond (when it is $C_0$), methylene, ethylene, or propylene (including all of its isomers).

"Alkenylene" means a straight or branched, unsaturated aliphatic divalent radical having two to six carbon atoms unless otherwise indicated e.g., $(C_{2-6})$alkenylene includes —CH=CH—, —CH$_2$CH=CH$_2$—, —CH$_2$CH$_2$CH=CH—, —CH=CH$_2$CH=CH—, and the like. Preferably, —CH=CH— or —CH$_2$CH=CH$_2$—.

"Alkylidene" means a straight or branched, unsaturated aliphatic divalent radical having the number of carbon atoms indicated e.g., $(C_{1-6})$alkylidene includes (=CH$_2$), (=CHCH$_3$), (=CHCH$_2$CH$_3$), and the like. Preferably, (=CH$_2$).

"Alkylimino" means a radical (=NR) where R is an alkyl group as defined above, e.g., $(C_{1-6})$alkylimino includes (=NCH$_3$), (=NCH$_2$CH$_3$), (=NCH$_2$CH$_2$CH$_3$), [=NCH$_2$CH(CH$_3$)CH$_3$], and the like.

"Acyl" means a radical —COR where R is alkyl as defined above, e.g., acetyl, propionyl, and the like.

"Aryl" means an aromatic monocyclic, polycyclic or fused polycyclic ring system containing 6-14 carbon atoms unless otherwise indicated wherein each ring contained therein is comprised of 6 annular members e.g., $(C_{6-14})$aryl includes phenyl, naphthalenyl, or anthracenyl, preferably phenyl.

"Animal" includes humans, non-human mammals (e.g., dogs, cats, rabbits, cattle, horses, sheep, goats, swine, deer, etc.) and non-mammals (e.g., birds, etc.).

"Cycloalkyl" means a saturated, monocyclic, polycyclic, or fused polycyclic ring system containing 3 to 8 annular carbon atoms unless otherwise indicated, e.g., $(C_{3-8})$cycloalkyl includes cyclopropyl, cyclobutyl, cyclopentyl, or cyclohexyl, preferably cyclopropyl, cyclopentyl, or cyclohexyl. Preferably, cyclopropyl, cyclopentyl, or cyclohexyl.

"Cycloalkenyl" means a partially unsaturated, monocyclic, polycyclic, or fused polycyclic ring system containing the number of annular carbon atoms indicated, or otherwise contains 3 to 8 carbon ring atoms, e.g., $(C_{3-8})$cycloalkenyl includes cyclopropenyl, cyclobutenyl, cyclopentenyl, cyclohexenyl, 2,5-cyclohexadienyl, decahydronaphthalenyl, and the like. Preferably, cyclopropenyl, cyclobutenyl, cyclopentenyl, or cyclohexenyl.

"Bridged polycyclic cycloalkylene" means a saturated divalent bridged polycyclic ring system containing from seven or eight ring carbon atoms unless otherwise indicated. For example, when $R^6$ and $R^{6a}$ together with the carbon atoms to which they are attached form a bridged polycyclic cycloalkylene moiety it includes, but is not limited to, the following rings:

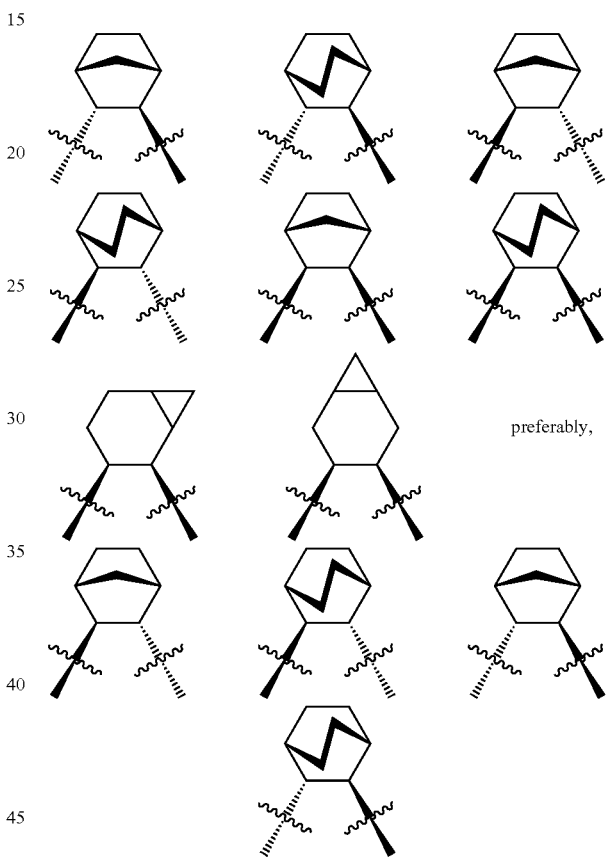

preferably,

"Bridged polycyclic cycloalkenylene" means a partially unsaturated divalent bridged polycyclic ring containing seven or eight ring carbon atoms unless otherwise indicated. Examples include, but are not limited to, rings such as

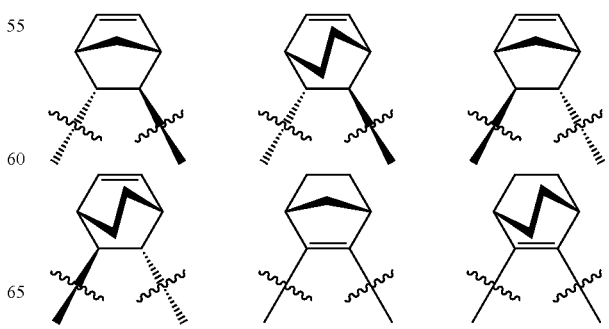

preferably,

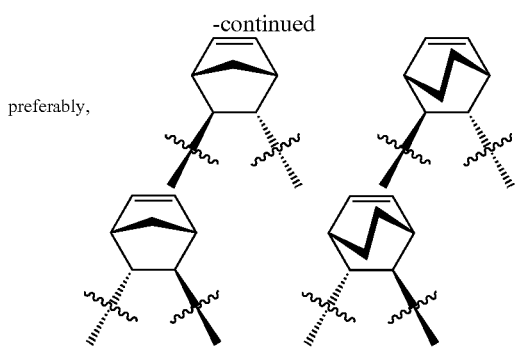

"Bridged polycyclic heterocycloalkylene" means a saturated divalent bridged polycyclic ring system containing seven or eight ring atoms unless otherwise indicated, wherein one or more, preferably one, two, or three of the ring atoms is a heteroatom moiety independently selected from N, NR, O, S(O)$_n$ (where R is hydrogen, (C$_{1-6}$)alkyl, and n is 0, 1, or 2), preferably NR, O, S(O)$_n$. For example, when R$^6$ and R$^{6a}$ together with the carbon atoms to which they are attached form a bridged polycyclic heterocycloalkylene moiety it includes, but is not limited to,

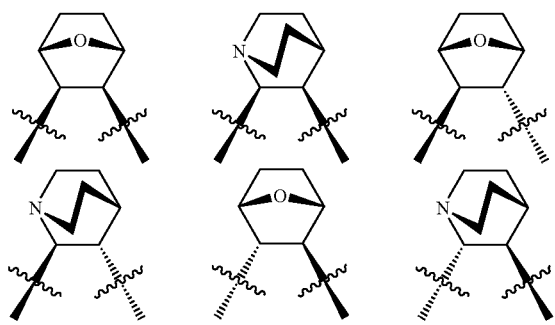

"Bridged polycyclic heterocycloalkenylene" means a partially unsaturated divalent bridged polycyclic ring system containing seven or eight ring atoms unless otherwise indicated, wherein one or more of the ring atoms is a heteroatom moiety independently selected from N, NR, O, S(O)$_n$ (where R is hydrogen, (C$_{1-6}$)alkyl, and n is 0, 1, or 2), preferably NR, O, S(O)$_n$. For example, when R$^6$ and R$^{6a}$ together with the carbon atoms to which they are attached form a bridged polycyclic heterocycloalkenylene moiety it includes, but is not limited to, the following ring:

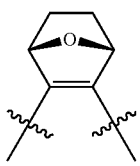

It will readily apparent to a person skilled in the art that the double bond can be moved to other positions in the above ring.

"Disease" specifically includes any unhealthy condition of an animal or part thereof and includes an unhealthy condition which may be caused by, or incident to, medical or veterinary therapy applied to that animal, i.e., the "side effects" of such therapy.

"Halo" means fluoro, chloro, bromo or iodo.

"Halo-substituted alkyl" means an alkyl group as defined herein wherein one, two, or three hydrogen atoms in the alkyl group has been replaced by a halo group as defined above, e.g., trifluoromethyl, difluorochloromethyl, tribromomethyl, chlorofluoroethyl, dichlorofluoroethyl, chlorodifluoromethyl including all the isomeric forms thereof, and the like.

"Heteroalkyl" means an alkyl radical as defined above, wherein one or two carbon atoms in the alkyl radical have been replaced by a group independently selected from —O—, —S—, —SO—, —SO$_2$—, —SO$_3$—, —NH—, —NHCO—, —CONH—, —NHSO$_2$—, —SO$_2$NH—, —NHC(O)O—, —OC(O)NH—, —C(O)—, —C(O)O—, —OC(O)—, and further wherein the alkyl radical is optionally substituted with one or two substituents independently selected from halo, —NR$^a$R$^b$, —OR$^c$, or —S(O)$_n$R$^d$ (wherein n is an integer from 0 to 2, R$^a$ is hydrogen, alkyl, halo substituted alkyl, or acyl; R$^b$ is hydrogen, alkyl, aryl, aryl(C$_{1-6}$)alkyl, heteroaryl, or heteroaryl(C$_{1-6}$)alkyl; R$^c$ is hydrogen, alkyl, or halo-substituted alkyl, and R$^d$ is hydrogen (provided that n is 0), alkyl, halo-substituted alkyl, amino, (C$_{1-6}$)alkylamino or di(C$_{1-6}$)alkylamino). Representative examples include, but are not limited to 2-methoxyethyloxy, 2-dimethylsulfonylaminoethylsulfanyl, 2-hydroxyethylsulfanyl, 2-methylcarbonylaminoethylsulfanyl, and the like.

"Heteroalkylene" means an alkylene radical as defined above, wherein one or two carbon atoms have been replaced by a group indendently selected from —O—, —S—, —SO—, —SO$_2$—, —SO$_3$—, —NH—, NHCO—, —CONH—, —NHSO$_2$—, —SO$_2$NH—, —NHC(O)O—, —OC(O)NH—, —C(O)—, —C(O)O—, —OC(O)—, and further wherein the alkylene radical is optionally substituted with one or two substituents independently selected from halo, —NR$^a$R$^b$, —OR$^c$, or —S(O)$_n$R$^d$ (wherein n is an integer from 0 to 2, R$^a$ is hydrogen, alkyl, halo substituted alkyl, or acyl; R$^b$ is hydrogen, alkyl, aryl, aryl(C$_{1-6}$)alkyl, heteroaryl, or heteroaryl(C$_{1-6}$)alkyl; R$^c$ is hydrogen, alkyl, or halo-substituted alkyl, and R$^d$ is hydrogen (provided that n is 0), alkyl, halo-substituted alkyl, amino, (C$_{1-6}$)alkylamino or di(C$_{1-6}$)alkylamino).

"Heteroaryl" or "heteroarylene" means an aromatic monocyclic, polycyclic, or fused polycyclic ring system containing 5 to 14 ring atoms (unless otherwise indicated) wherein one, two, or three ring atoms are heteroatoms independently selected from N, NR, O, or S(O)$_n$ (wherein R is hydrogen, (C$_{1-6}$)alkyl or a protective group and n is 0, 1, or 2), the remaining ring atoms being carbon. Representative examples include, but are not limited to, thienyl, furyl, pyrrolyl, imidazolyl, pyrimidinyl, pyradizinyl, pyrazinyl, isoxazolyl, oxazolyl, indolyl, benzo[b]thienyl, isobenzofuranyl, purinyl, quinolinyl, isoquinolyl, pterdinyl, perimidinyl, 1-methylimidazolyl, 1-benzylimidazolyl, pyridyl, pyrazolyl, [2,4']bipyridinylyl, 2-phenylpyridinyl, and the like.). The definition of heteroaryl or heteroarylene also includes the N-oxide derivatives (≡N$^+$→O$^-$) i.e., where the nitrogen atom in the ring is oxidized. Suitable protective groups include tert-butoxycarbonyl, benzyloxycarbonyl, benzyl, 4-methoxybenzyl, 2-nitrobenzyl, and the like.

"Heterocycloalkyl" means cycloalkyl, as defined herein, where one or more, preferably one, two, or three of the annular carbon atoms indicated is replaced by a heteroatom independently selected from NR, O or S(O)$_n$ (wherein R is hydrogen, $(C_{1-6})$alkyl or a protective group and n is 0, 1, or 2) e.g., the term heterocycloalkyl includes tetrahydrofuranyl, piperidyl, pyrrolidinyl, pyrrolinyl, imidazolidinyl, quinuclidinyl, morpholinyl, thiomorpholinyl, and the like. The definition of heterocycloalkyl also includes the N-oxide derivatives ($\equiv$N$^+$→O$^-$) i.e., where the nitrogen atom in the ring is oxidized. Suitable protective groups include tert-butoxycarbonyl, benzyloxycarbonyl, benzyl, 4-methoxybenzyl, 2-nitrobenzyl, and the like.

"Heterocycloalkenyl" means cycloalkenyl, as defined herein, where one or more, preferably one, two, or three of the annular carbon atoms indicated is replaced by a heteroatom independently selected from N, NR, O, or $S(O)_n$ (wherein R is hydrogen, $(C_{1-6})$alkyl or a protective group and n is 0, 1, or 2) e.g., the term heterocycloalkenyl includes dihydropyridinyl, tetrahydropyridinyl, tetrahydropyrimidinyl, tetrahydroquinolinyl, tetrahydroquinoxalinyl, tetrahydroindolyl, and the like. The definition of heterocycloalkenyl also includes the N-oxide derivatives ($\equiv$N$^+$→O$^-$) i.e., where the nitrogen atom in the ring is oxidized. Suitable protective groups include tert-butoxycarbonyl, benzyloxycarbonyl, benzyl, 4-methoxybenzyl, 2-nitrobenzyl, and the like.

"Imino" means the radical —(=NH).

"Isomers" mean compounds of Formula I having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diasteromer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 3rd edition, March, Jerry, John Wiley & Sons, New York, 1985). It is understood that the names and illustration used in this Application to describe compounds of Formula I are meant to be encompassed all possible stereoisomers and any mixture, racemic or otherwise, thereof.

"Monocyclic cycloalkylene" means a saturated divalent monocyclic ring containing from three to seven carbon ring atoms unless otherwise indicated. For example, when $R^6$ and $R^{6a}$ together with the carbon atoms to which they are attached form a monocyclic cycloalkylene moiety it includes, but is not limited to, the following rings:

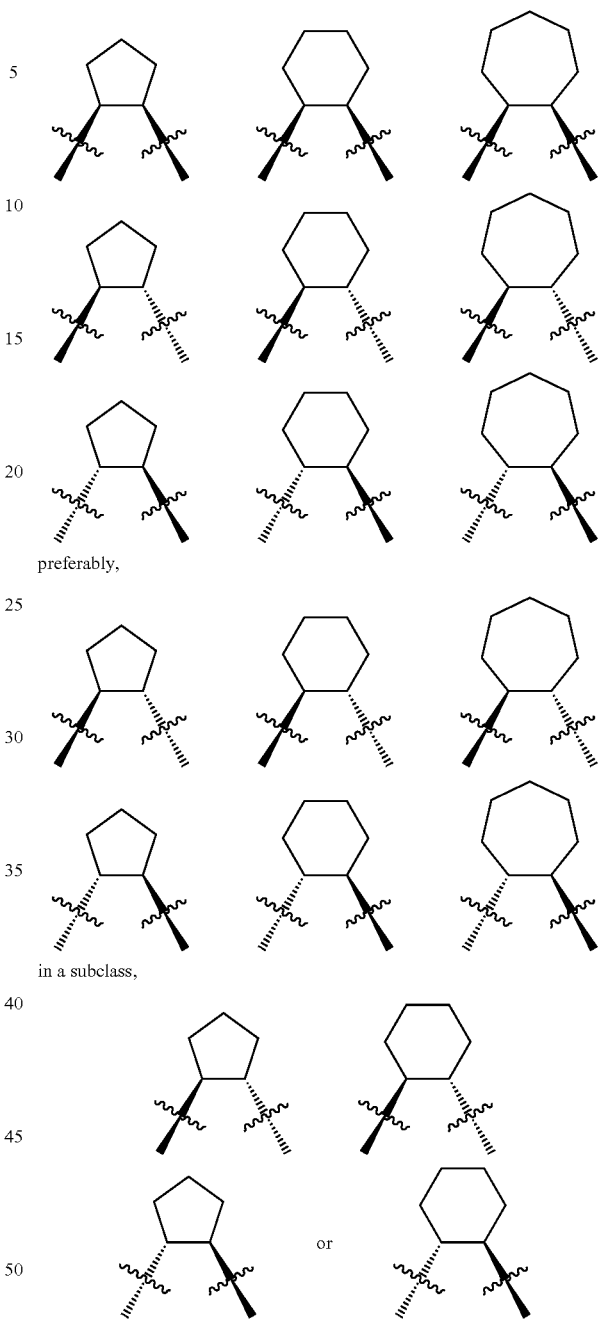

preferably, in a subclass, or

"Monocyclic cycloalkenylene" means a partially unsaturated divalent monocyclic ring containing from three to eight ring carbon atoms unless otherwise indicated. For example, when $R^6$ and $R^{6a}$ together with the carbon atoms to which they are attached form a monocyclic cycloalkenylene moiety it includes, but is not limited to, the following rings:

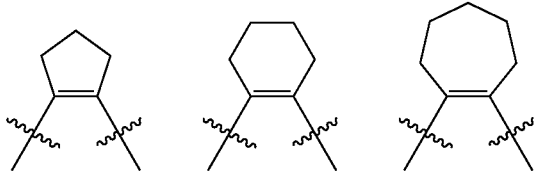

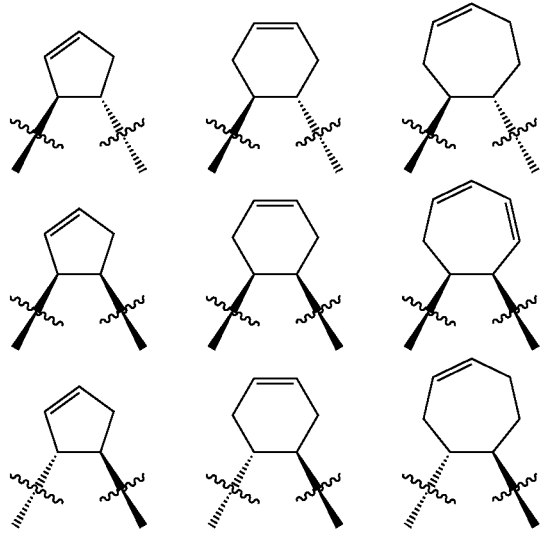

"Monocyclic heterocycloalkylene" means a saturated divalent monocyclic ring system containing from three to eight, preferably three to six ring atoms unless otherwise indicated, wherein one or more, preferably one, two, or three of the ring atoms is a heteroatom moiety independently selected from NR, O, S(O)$_n$ (where R is hydrogen, (C$_{1-6}$)alkyl, and n is 0, 1, or 2). For example, when R$^6$ and R$^{6a}$ together with the carbon atoms to which they are attached form a monocyclic heterocycloalkylene moiety it includes, but is not limited to, the following rings:

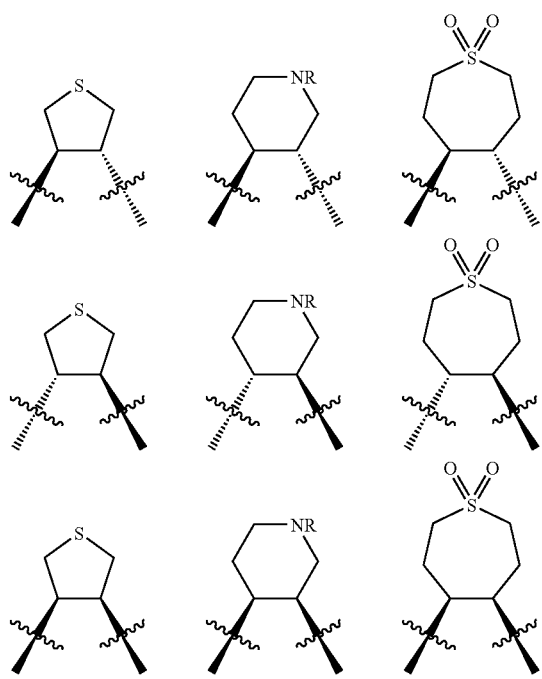

"Monocyclic heterocycloalkenylene" means a partially unsaturated divalent monocyclic ring system containing from three to eight ring atoms, preferably three to six ring atoms unless otherwise indicated, wherein one or more of the ring atoms is a heteroatom moiety independently selected from N, NR, O, S(O)$_n$ (where R is hydrogen, (C$_{1-6}$)alkyl, and n is 0, 1, or 2), preferably NR, O, S(O)$_n$. For example, when R$^6$ and R$^{6a}$ together with the carbon atoms to which they are attached form a monocyclic heterocycloalkylene moiety it includes, but is not limited to, the following rings:

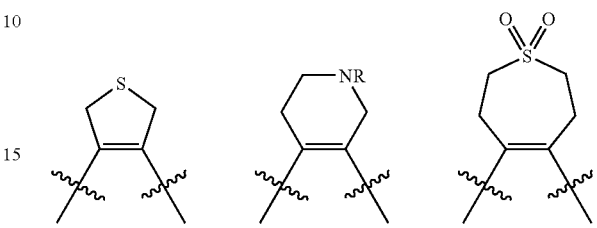

"Nitro" means the radical NO$_2$.

"Optional" or "optionally" means that the subsequently described event or circumstance may or may not occur, and that the description includes instances where the event or circumstance occurs and instances in which it does not. For example, the phrase "Ar is optionally substituted with —(C$_{1-6}$)alkyl" means that —(C$_{1-6}$)alkyl may but need not be present, and the description includes situations where the Ar group is substituted with —(C$_{1-6}$)alkyl and situations where the Ar group is not substituted with —(C$_{1-6}$)alkyl.

"Oxo" means the radical =(O).

"Pathology" of a disease means the essential nature, causes and development of the disease as well as the structural and functional changes that result from the disease processes.

"Pharmaceutically acceptable" means that which is userul in preparing a pharmaceutical composition that is generall safe, non-toxic and neither biologically nor otherwise undesirabale and includes that which is acceptable for veterinary use as well as human pharmaceutical use.

"Pharmaceutically acceptable salts" means salts of compounds of Formula I which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2] oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydoxide. Acceptable organic bases include ethanolamine, diethanolamine, triethanolamine, tromethamine, N-methylglucamine and the like.

"Ring system" as used herein means a monocyclic, bridged, or fused bicyclic ring.

"Spirocycloalkylene" means a saturated divalent polycyclic ring system containing from seven or eight ring carbon atoms that are bonded in such a way that a single carbon atom is common to both rings. Examples include, but are not limited to, rings such as:

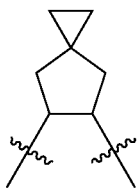

"Sulfanyl" or "thio" as used herein means the radical —S—.

The present invention also includes the prodrugs of a compound of Formula I. Prodrugs means any compound which releases an active parent drug according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs include compounds of Formula I wherein a hydroxy, amino, or sulfhydryl group in compound I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula I, and the like.

The present invention also includes the protected derivatives of a compounds of Formula I. Protected derivatives means derivatives of compounds of Formula I in which a reactive site or sites are blocked with protective groups. Protected derivatives of compounds of Formula I are useful in the preparation of compounds of Formula I or in themselves may be active cysteine protease inhibitors. A comprehensive list of suitable protective groups can be found in T. W. Greene, *Protective Groups in Organic Synthesis*, John Wiley & Sons, Inc. 1981, the disclosure of which is incorporated herein by reference in its entirety.

The present invention also includes the N-oxide derivative of a compound of Formula I. N-oxide derivative of a compound of Formula I can form when the compound of Formula I carries a nitrogen atom at a position that is susceptible to oxidation.

"Thioxo" means the radical =(S).

"Therapeutically effective amount" means that amount which, when administered to an animal for treating a disease, is sufficient to effect such treatment for the disease.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

Nomenclature:

The compounds of Formula I and the intermediates and starting materials used in their preparation are named generally in accordance with IUPAC rules of nomenclature in which the characteristic groups have decreasing priority for citation as the principle group as follows: acids, esters, amides and amidines. For example, a compound of Formula I in which:

Ar is 4-fluorophenyl, $X^1$ is S, A is cyclohexyl and the bonds to the methylene and the —C=O group are trans, and $R^1$, $R^2$, and $R^3$ are hydrogen is named trans-N-cyanomethyl-2-(4-fluorophenylsulfanylmethyl)cyclohexanecarboxamide;

Ar is 4-(4-piperazin-1-ylphenyl)phenyl, $X^1$ is $SO_2$, A is cyclohexyl and the bonds to the methylene and the —C=O group are trans, and $R^1$, $R^2$, and $R^3$ are hydrogen is named trans-N-cyanomethyl-2-[4-(4-piperazin-1-ylphenyl)benzenesulfonylmethyl)cyclohexanecarboxamide; and Ar is benzoxazol-2-yl, $X^1$ is S, A is cyclohexyl and the bonds to the methylene and the —C=O group are trans, and $R^1$, $R^2$, and $R^3$ are hydrogen is named trans-N-cyanomethyl-2-(benzoxazol-2-yl-sulfanylmethyl)cyclohexanecarboxamide.

Classes of Embodiments

While the broadest definition of this Invention is set forth in the Summary of the Invention, certain classes of compounds of Formula I are discussed below.

(A) One class group of compounds is that wherein:

$R^1$ is hydrogen;

$R^2$ is hydrogen, $(C_{1-6})$alkyl or halo substituted $(C_{1-3})$ alkyl; in a subclass hydrogen, methyl, ethyl, propyl or butyl (including all the isomeric forms), or trifluoromethyl; in a further subclass hydrogen;

$R^3$ is hydrogen $R^4$ and $R^5$ independently hydrogen, or $(C_{1-6})$alkyl or $R^4$ and $R^5$ together with the carbon atoms to which they are attached form $(C_{3-6})$monocyclic cycloalkylene or $(C_{3-6})$ monocyclic heterocycloalkylene; in a class $R^4$ and $R^5$ are hydrogen, methyl or ethyl or $R^4$ and $R^5$ together with the carbon atom to which they are attached form cyclopropylene, cyclobutylene, cyclopentylene, cyclohexylene, tetrahydrofuranyl, 2, 3, or 4-piperidinyl, or 1,4-piperazinyl. In a class, $R^4$ and $R^5$ are hydrogen or methyl or $R^4$ and $R^5$ together with the carbon atom to which they are attached form cyclopropylene, in a subclass $R^4$ and $R^5$ are hydrogen.

(B) Another preferred group of compounds is that wherein:

$R^6$ and $R^{6a}$ together with the carbon atoms to which they are attached form $(C_{3-7})$monocyclic cycloalkylene, spirocycloalkylene or $(C_{7-8})$ bridged polycyclic cycloalkylene where said monocyclic alkylene or bridged polycyclic cycloalkylene is optionally substituted with hydroxy or $(C_{1-3})$alkyl, in a class $R^6$ and $R^{6a}$ together with the carbon atoms to which they are attached form $(C_{3-7})$monocyclic cycloalkylene or $(C_{7-8})$ bridged polycyclic cycloalkylene where said monocyclic alkylene or bridged polycyclic cycloalkylene is optionally substituted with hydroxy or $(C_{1-3})$alkyl, in a subclass $R^6$ and $R^{6a}$ together with the carbon atoms to which they are attached form:

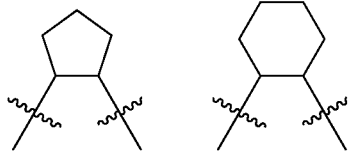 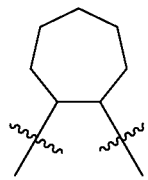 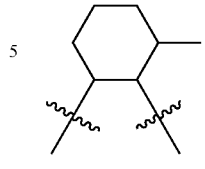 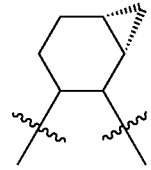
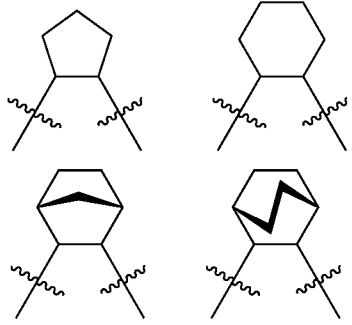 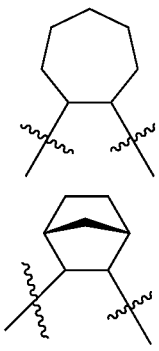 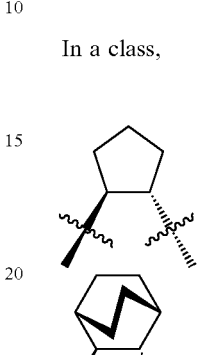
In a class,
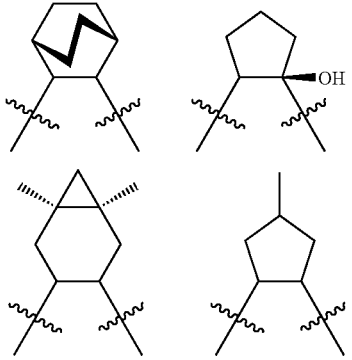  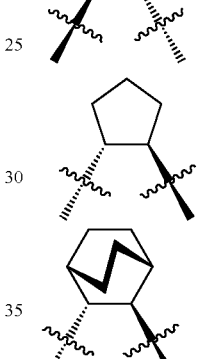
In a subclass,
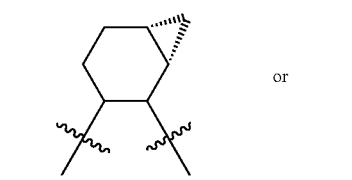 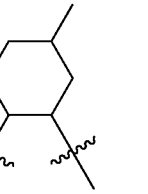 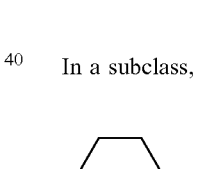
Particularly, exemplifying the invention is,
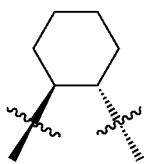 or 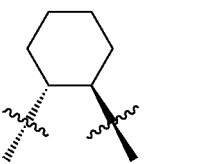
or diastereomeric mixtures thereof.
In a class,
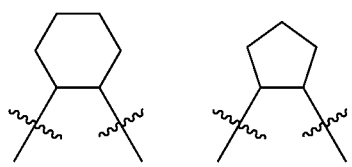 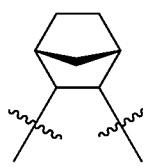 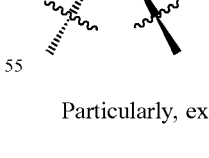
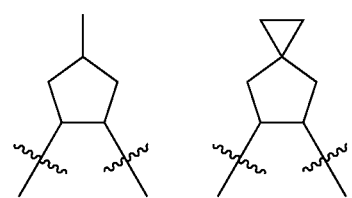 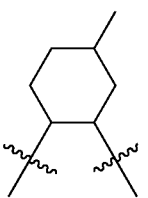 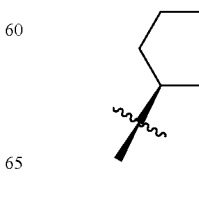

Within this group (1), a subclass of compounds is that wherein:

$R^1$ is hydrogen;
$R^2$ is hydrogen, $(C_{1-6})$alkyl or halo substituted $(C_{1-3})$alkyl; preferably hydrogen, methyl, ethyl, propyl or butyl (including all the isomeric forms), or trifluoromethyl; in a subclass hydrogen;
$R^3$ is hydrogen; and
$R^4$ and $R^5$ independently hydrogen, or $(C_{1-6})$alkyl or $R^4$ and $R^5$ together with the carbon atoms to which they are attached form $(C_{3-6})$monocyclic cycloalkylene or $(C_{3-6})$ monocyclic heterocycloalkylene; in a class $R^4$ and $R^5$ are hydrogen, methyl or ethyl or $R^4$ and $R^5$ together with the carbon atoms to which they are attached form cyclopropylene, cyclobutylene, cyclopentylene, cyclohexylene, tetrahydrofuranyl, 2, 3, or 4-piperidinyl, or 1,4-piperazinyl. Preferably, $R^4$ and $R^5$ are hydrogen, methyl or $R^4$ and $R^5$ together with the carbon atoms to which they are attached form cyclopropylene, in a subclass $R^4$ and $R^5$ are hydrogen.

Within this group (B), another subclass of compounds is that wherein:
$R^1$ and $R^2$ together with the carbon atom to which they are attached form cyclopropyl;
$R^3$ is hydrogen; and
$R^4$ and $R^5$ are hydrogen.

(C) Another subclass of compounds of Formula I is that wherein:
$R^6$ and $R^{6a}$ together with the carbon atom to which they are attached form $(C_{3-7})$monocyclic cycloalkenylene or bridged cycloalkenylene, in a class

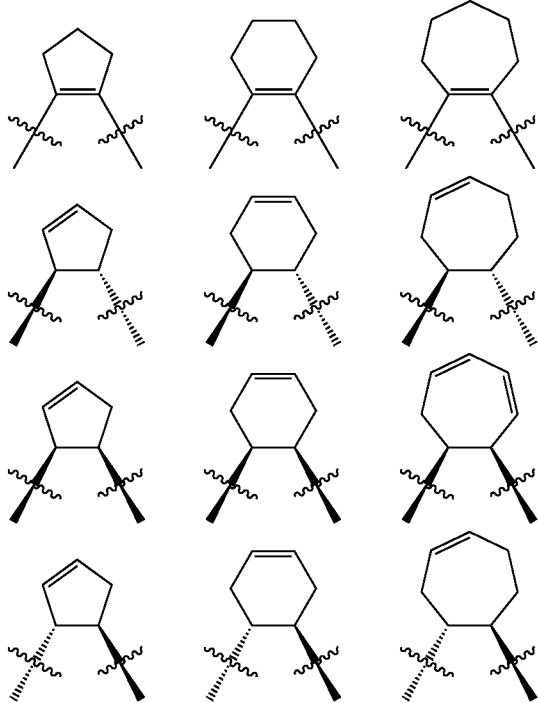

or

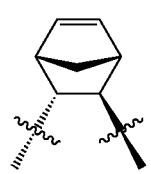

In a subclass,

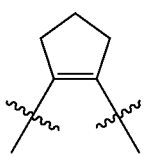 or 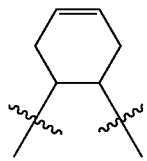

Exemplifying the invention,

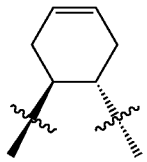

Within this group (C), a subclass of compounds is that wherein:
$R^1$ is hydrogen;
$R^2$ is hydrogen, $(C_{1-6})$alkyl or halo substituted $(C_{1-3})$alkyl; in a class hydrogen, methyl, ethyl, propyl or butyl (including all the isomeric forms), or trifluoromethyl; in a subclass hydrogen;
$R^3$ is hydrogen; and
$R^4$ and $R^5$ independently hydrogen, or $(C_{1-6})$alkyl or $R^4$ and $R^5$ together with the carbon atoms to which they are attached form $(C_{3-6})$monocyclic cycloalkylene or $(C_{3-6})$ monocyclic heterocycloalkylene; in a class, $R^4$ and $R^5$ are hydrogen, methyl or ethyl or $R^4$ and $R^5$ together with the carbon atoms to which they are attached form cyclopropylene, cyclobutylene, cyclopentylene, cyclohexylene, tetrahydrofuranyl, 2, 3, or 4-piperidinyl, or 1,4-piperazinyl.

Preferably, $R^4$ and $R^5$ are hydrogen, methyl or $R^4$ and $R^5$ together with the carbon atoms to which they are attached form cyclopropylene, most preferably $R^4$ and $R^5$ are hydrogen.

Within this group (C), another subclass of compounds is that wherein:
$R^1$ and $R^2$ together with the carbon atom to which they are attached form cyclopropyl;
$R^3$ is hydrogen; and
$R^4$ and $R^5$ are hydrogen.

(D) Another class of compounds of Formula I is that wherein:
$R^6$ and $R^{6a}$ together with the carbon atom to which they are attached form phenylene or heteroarylene, in a subclass, phenylene optionally substituted with methyl, chloro, or fluoro.

Within this group (I), a subclass of compounds is that wherein:
$R^1$ is hydrogen;
$R^2$ is hydrogen, $(C_{1-6})$alkyl or halo substituted $(C_{1-3})$alkyl; in a class hydrogen, methyl, ethyl, propyl, or butyl (including all the isomeric forms), or trifluoromethyl; in a subclass, hydrogen;
$R^3$ is hydrogen; and
$R^4$ and $R^5$ independently hydrogen, or $(C_{1-6})$alkyl or $R^4$ and $R^5$ together with the carbon atoms to which they are attached form $(C_{3-6})$monocyclic cycloalkylene or $(C_{3-6})$ monocyclic heterocycloalkylene; in a class, $R^4$ and $R^5$ are hydrogen, methyl or ethyl or $R^4$ and $R^5$ together with the carbon atoms to which they are attached form cyclopropylene, cyclobutylene, cyclopentylene, cyclohexylene, tetrahydrofuranyl, 2, 3, or 4-piperidinyl, or 1,4-piperazinyl.

In a class, $R^4$ and $R^5$ are hydrogen, methyl or $R^4$ and $R^5$ together with the carbon atoms to which they are attached form cyclopropylene, in a subclass, $R^4$ and $R^5$ are hydrogen.

(i) Within the above classes and subclasses (A-D), a further subclass of compounds is that wherein:

$X^1$ is —O—, S, or —$SO_2$—, in a subclass —S— or —$SO_2$—; and

Ar is $Ar^1$ where $Ar^1$ is phenyl or napthyl, in a class, phenyl, optionally substituted with one, two, or three groups independently selected from the group consisting of $(C_{1-6})$alkyl, cyano, halo, halo-substituted $(C_{1-4})$alkyl, nitro, —$X^9NR^{16}R^{16}$, —$X^9NR^{16}C(O)R^{16}$, —$X^9C(O)NR^{16}R^{16}$, —$X^9NR^{16}C(O)OR^{16}$, —$X^9OC(O)NR^{16}R^{16}$—$X^9NR^{16}C(O)NR^{16}R^{16}$, —$X^9NR^{16}C(NR^{16})NR^{16}R^{16}$, —$X^9OR^6$, —$X^9C(O)R^{16}$, —$X^9C(O)OR^{16}$, —$X^9OC(O)R^{16}$, $X^9S(O)_2NR^{16}R^{16}$, —$X^9P(O)(OR^{16})OR^{16}$, —$X^9OP(O)(OR^{16})OR^{16}$, —$X^9SR^{16}$, —$X^9S(O)R^{17}$, —$X^9S(O)_2R^{17}$, —$OS(O)_2R^{17}$ and —$X^9NR^7S(O)_2R^{17}$, wherein $X^9$ is a bond or $(C_{1-6})$alkylene, $R^{16}$ at each occurrence independently is hydrogen, $(C_{1-6})$alkyl, or halo-substituted $(C_{1-3})$alkyl, and $R^{17}$ is $(C_{1-6})$alkyl, or halo-substituted $(C_{1-3})$alkyl. In a class, the phenyl ring is optionally substituted with one or two substituents independently selected from $(C_{1-6})$alkyl, cyano, halo, halo-substituted $(C_{1-4})$alkyl, nitro, —$NR^{16}R^{16}$, —$NR^{16}C(O)R^{16}$, —$X^9OR^{16}$, —$X^9C(O)OR^{16}$, —$SR^{16}$, —$S(O)_2R^{17}$, —$OS(O)_2R^{17}$ and —$NR^7S(O)_2R^{17}$. In a class, the phenyl ring is optionally substituted with one or two groups independently selected from the group consisting of methyl, ethyl, isopropyl, tert-butyl, chloro, fluoro, bromo, trifluoromethyl, —$NH_2$, —$N(CH_3)_2$, nitro, —$NHCOCH_3$, —NHCHO, —$NHCOCF_3$, —$CH_2OH$, —OH, —$OCH_3$, —$OCHF_2$, —$OCF_3$, —$OCH_2CH_3$, —$OCH(CH_3)_2$, —COOH, —$CH_2COOH$, —$(CH_2)_2$—COOH, —$(CH_2)_3$—COOH, —$SCH_3$, —$SC(CH_3)_3$, —$OSO_2CF_3$, —$SCHF_2$, —$SCH_2CF_3$, —$SO^2NH^2$, —$SO_2CH_3$, —$SO_2NHCH_3$, or —$SO_2N(CH_3)_2$. In a subclass, the phenyl is optionally substituted with one or two groups independently selected from the group consisting of fluoro, bromo, chloro, methyl, —$OCH_3$, —$NHCOCH_3$, nitro, tert-butyl, trifluoromethyl, —OH, —$SCH_3$, and —$SO_2CH_3$.

(ii) Within the above classes and subclasses (A-D), another subclass of compounds is that wherein:

$X^1$ is —O—, S, or —$SO_2$—, in a subclass —S— or —$SO_2$—; and

Ar is $Ar^1$ where $Ar^1$ is phenyl substituted with heteroalkyl, in a class, phenyl substituted with ethoxycarbonylmethylsulfanyl, 3-hydroxypropylsulfanyl, 2-aminoethylsulfanyl, 2-tert-butoxycarbonylaminoethylsulfanyl, 2-(2,2,2-trifluoroethylamino)ethylsulfanyl, 3-dimethylaminopropyloxy, methylaminocarbonylmethylsulfanyl, 2-(acetylamino)ethoxy, 2-aminoethylsulfanyl, 2-(acetylamino)ethylsulfanyl, 2-(ethylsulfonylamino)ethylsulfanyl, 2-(dimethylaminosulfonylamino)-ethylsulfanyl, 2-(methylsulfonyloxy)ethylsulfanyl, 2-hydroxyethylsulfanyl, methoxycarbonylmethoxy, 1-ethoxycarbonylethylsulfanyl, trifluoromethylsulfonyloxy, or 2-bromoethylsulfanyl. In a subclass, phenyl substituted with 2-aminoethylsulfanyl, 2-(methylsulfonyloxy)ethylsulfanyl, 2-tert-butoxycarbonylaminoethyl-sulfanyl, or 2-bromoethylsulfanyl.

(iii) Within the above classes and subclasses (A-D), another subclass of compounds is that wherein:

$X^1$ is —O—, S, or —$SO_2$—, in a subclass, —S— or —$SO_2$—; and

Ar is $Ar^1$ where $Ar^1$ is heteroaryl of 5 or 9 ring atoms containing one or two heteroatoms independently selected from the group consisting of NR (where R is hydrogen or methyl), S, or O, preferably $Ar^1$ is imidazolyl, 1-methylimidazol-2-yl, benzoxazol-2-yl, benzthiazol-2-yl, pyrimidin-2-yl, thiazol-4-yl, or pyridin-4-yl, optionally substituted with —$(C_{1-6})$alkyl, cyano, halo, halo-substituted $(C_{1-4})$alkyl, nitro, —$X^9NR^{16}R^{16}$, —$X^9NR^{16}C(O)R^{16}$, —$X^9C(O)NR^{16}R^{16}$, —$X^9OR^{16}$, —$X^9C(O)R^{16}$, —$X^9S(O)_2NR^{16}R^{16}$, —$X^9SR^{16}$, —$X^9S(O)R^{17}$, —$X^9S(O)_2R^{17}$ and —$X^9NR^7S(O)_2R^{17}$, wherein $X^9$ is a bond or $(C_{1-6})$alkylene, $R^{16}$ at each occurrence independently is hydrogen, $(C_{1-6})$alkyl, or halo-substituted $(C_{1-3})$alkyl, and $R^{17}$ is $(C_{1-6})$alkyl, or halo-substituted $(C_{1-3})$alkyl. Preferably $Ar^1$ is imidazolyl, 1-methylimidazol-2-yl, benzoxazol-2-yl, benzthiazol-2-yl, pyrimidin-2-yl, thiazolyl, or pyridin-4-yl optionally substituted with one or two groups independently selected from the group consisting of methyl, ethyl, isopropyl, tert-butyl, cyano, chloro, fluoro, bromo, trifluoromethyl, —$NH_2$, —$NHCH_3$, —$N(CH_3)_2$, nitro, —$NHCOCH_3$, —$CONH_2$, —$CONHCH_3$, —$CON(CH_3)_2$, —OH, —$OCH_3$, —$OCH_2CH_3$, —$COCH_3$, —COOH, —$COOCH_3$, —$OCOCH_3$, —$SCH_3$, —$SO_2NH_2$, —$SO_2NHCH_3$, —$SO_2N(CH_3)_2$, —$SO_2NHphenyl$, —$SO_2NHbenzyl$, —$SO_2phenyl$, —$SO_2benzyl$. In a subclass, $Ar^1$ is imidazolyl, 1-methylimidazol-2-yl, benzoxazol-2-yl, benzthiazol-2-yl, pyrimidin-2-yl, thiazol-4-yl, or pyridin-4-yl optionally substituted with one or two groups independently selected from the group consisting of fluoro, bromo, methyl, —$OCH_3$, —NHCOCH$_3$, nitro, tert-butyl, trifluoromethyl, —OH, and —$SO_2CH_3$.

(iv) Within the above classes and subclasses (A-D), another subclass of compounds is that wherein:

$X^1$ is —O—, S, or —$SO_2$—, in a subclass, —S— or —$SO_2$—; and

Ar is $Ar^1$ where $Ar^1$ is heterocycloalkyl of 5 to 6 ring atoms containing one or two heteroatoms independently selected from the group consisting of NR (where R is hydrogen or methyl), S, or O, preferably morpholino, pyrrolidino, piperazino, piperidino, or thiomorpholino optionally substituted with —$(C_{1-6})$alkyl, cyano, halo, halo-substituted $(C_{1-4})$alkyl, nitro, —$X^9NR^{16}R^{16}$, —$X^9NR^{16}C(O)R^{16}$, —$X^9C(O)NR^{16}R^{16}$, —$X^9OR^{16}$, —$X^9C(O)R^{16}$, —$X^9S(O)_2NR^{16}R^{16}$, —$X^9SR^{16}$, —$X^9S(O)R^{17}$, —$X^9S(O)_2R^{17}$ and —$X^9NR^7S(O)_2R^{17}$, wherein $X^9$ is a bond or $(C_{1-6})$alkylene, $R^{16}$ at each occurrence independently is hydrogen, $(C_{1-6})$alkyl, or halo-substituted $(C_{1-3})$alkyl, and $R^{17}$ is $(C^{1-6})$alkyl, or halo-substituted $(C_{1-3})$alkyl. In a class, $Ar^1$ is morpholino, pyrrolidino, piperazino, piperidino, or thiomorpholino optionally substituted with one, two, or three groups independently selected from the group consisting of methyl, ethyl, isopropyl, tert-butyl, cyano, chloro, fluoro, bromo, trifluoromethyl, —$NH_2$, —$NHCH_3$, —$N(CH_3)_2$, nitro, —$NHCOCH_3$, —$CONH_2$, —$CONHCH_3$, —$CON(CH_3)_2$, —OH, —$OCH_3$, —$OCH_2CF_3$, —$COCH_3$, —COOH, —$COOCH_3$, —$OCOCH_3$, —$SCH_3$, —$SO_2NH_2$, —$SO_2NHCH_3$, —$SO_2N(CH_3)_2$, —$SO_2NHphenyl$, —$SO_2NHbenzyl$, —$SO_2phenyl$, —$SO_2benzyl$. In a subclass, $Ar^1$ is morpholino, pyrrolidino, piperazino, piperidino, or thiomorpholino optionally substituted with one, two, or three groups independently selected from the group consisting of fluoro, bromo, methyl, —$OCH_3$, —$NHCOCH_3$, nitro, tert-butyl, trifluoromethyl, —OH, and —$SO_2CH_3$.

(v) Within the above classes and subclasses (A-D), another subclass of compounds is that wherein:

$X^1$ is —O—, S, or —$SO_2$—, in a subclass, —S— or —$SO_2$—; and

Ar is 4-fluorophenyl, 4-bromophenyl, 4-chlorophenyl, 4-methylphenyl, 4-methoxyphenyl, 4-(—NHCOCH$_3$)phenyl, 4-nitrophenyl, 4-trifluoromethylphenyl, 4-tert-butylphenyl, 4-trifluoromethylphenyl, 4-methylsulfanylphenyl, 4-methylsulfonylphenyl, 4-hydroxyphenyl, 4-aminophenyl, 2-chlorophenyl, 2,4-dichlorophenyl, 2,5-dichlorophenyl, 2-methylphenyl, 3,4-dichlorophenyl, 3,5-dichlorophenyl, 3-chlorophenyl, 4-dimethylaminophenyl, 3-methylphenyl, 4-trifluoromethoxyphenyl, 3-methoxyphenyl, 3,4-dimethoxyphenyl, 2,5-dimethoxyphenyl, 4-thiolphenyl, 4-isopropyloxyphenyl, 3-trifluoromethylphenyl, 3-(—NHCOCH$_3$)phenyl, 3-fluorophenyl, 3-aminophenyl, 3-carboxymethylphenyl, 4-carboxyphenyl, 3-hydroxyphenyl, 3-formylaminophenyl, 3-trifluoroacetylaminophenyl, 4-hydroxymethylphenyl, 4-trifluoro-sulfonyloxyphenyl, 3-carboxylphenyl, 4-ethylsulfanylphenyl, 3-methylsulfonylaminophenyl, 3,4-dimethylsulfanylphenyl, 3,4-difluorophenyl, 4-tert-butylsulfanylphenyl, 2,4-difluorophenyl, 3-fluoro-4-methylsulfanylphenyl, 4-(3-carboxypropyl)phenyl, 4-(2-carboxyethyl)phenyl, 4-carboxymethyl-phenyl, 4-iodophenyl, 4-(2,2,2-trifluoroethylsulfanyl)phenyl, 4-difluoromethoxyphenyl, 4-difluoromethylsulfanylphenyl, 4-ethoxycarbonyl-methylsulfanylphenyl, 3-hydroxypropylsulfanylphenyl, 2-aminoethylsulfanylphenyl, 4-(2-tert-butoxycarbonylaminoethylsulfanyl)phenyl, 4-[2-(2,2,2-trifluoroethylamino)ethylsulfanyl]phenyl, 4-methylaminocarbonylmethylsulfanylphenyl, 4-[2-(acetylamino)ethoxy]phenyl, 4-[2-aminoethylsulfanyl]phenyl, 4-[2-(acetylamino)ethylsulfanyl]phenyl, 3-fluoro-4-[2-(ethylsulfonylamino)ethylsulfanyl]phenyl, 3-fluoro-4-[2-(dimethylaminosulfonylamino)-ethylsulfanyl]phenyl, 4-[2-(methylsulfonyloxy)ethylsulfanyl]phenyl, 4-[2-hydroxyethylsulfanyl]-phenyl, 4-methoxycarbonylmethoxyphenyl, 4-[1-ethoxycarbonylethylsulfanyl]phenyl, 4-trifluoromethylsulfonyloxyphenyl, or 4-[2-bromoethylsulfanyl]phenyl. In a subclass, Ar is 4-hydroxyphenyl, 4-methylsulfanylphenyl, 4-[2-aminoethylsulfanyl]phenyl, 4-[2-(methyl-sulfonyloxy)ethylsulfanyl]phenyl, 4-[2-tert-butoxycarbonylaminoethylsulfanyl]phenyl, or 4-[2-bromoethylsulfanyl]phenyl.

(vi) Within the above classes and subclasses of compounds (A-D), another subclass of compounds is that wherein:

$X^1$ is —O—, S, or —SO$_2$—, in a subclass, —S— or —SO$_2$—; and

Ar is $Ar^2$—$X^4$—$Ar^1$— where $Ar^1$ is phenyl;

$X^4$ is selected from the group consisting of a bond, —(C$_{1-6}$)alkylene, —X$^7$NR$^{15}$X$^8$—, —X$^7$NR$^{15}$C(O)X$^8$—, —X$^7$C(O)NR$^{15}$X$^8$—, —X$^7$NR$^{15}$C(O)OX$^8$—, —X$^7$OC(O)NR$^{15}$X$^8$—, —X$^7$NR$^{15}$C(O)NR$^{15}$X$^8$—, —X$^7$OX$^8$—, —X$^7$C(O)X$^8$—, —X$^7$C(O)OX$^8$—, —X$^7$OC(O)X$^5$—, —X$^7$S(O)$_2$NR$^{15}$X$^8$—, —X$^7$SX$^8$—, —X$^7$S(O)X$^8$—, —X$^7$S(O)$_2$X$^8$— and —X$^7$NR$^{15}$S(O)$_2$X$^8$—, wherein $X^7$ and $X^8$ independently are a bond or —(C$_{1-6}$)alkylene and R$^{15}$ is hydrogen or —(C$_{1-6}$)alkyl; in a class, $X^4$ is a bond, methylene, ethylene, propylene, —CH$_2$NH—, —NHCH$_2$—, —CH$_2$NHCO—, —CH$_2$NHCO(CH$_2$)$_3$—, —CH$_2$NHCOCH$_2$—, —CH$_2$NHCO(CH$_2$)$_2$—, —NHCONH—, —CONH—, —NHC(O)O—, —OC(O)NH—, —SO$_2$NH—, —NHSO$_2$—, —O—, —CH$_2$O—, —(CH$_2$)$_2$O—, —OCH$_2$—, —S—, —SO$_2$—, —(CH$_2$)$_2$S—, —CH$_2$S—, —(CH$_2$)$_2$SO—, —(CH$_2$)$_2$SO$_2$—, —CH$_2$SO$_2$CH$_2$—, —(CH$_2$)$_2$SO$_2$CH$_2$—, —(CH$_2$)$_2$SCH$_2$—, or —CH$_2$SCH$_2$—; in a class, $X^4$ is a bond, —CH$_2$S—, or —(CH$_2$)$_2$S—; or $X^4$ is heteroalkylene, in a class —CH$_2$NHCOCH$_2$S—, —(CH$_2$)$_2$NHCOCH$_2$S—, —CONH(CH$_2$)$_2$S—, —NHCOCH$_2$S—, —O(CH$_2$)$_2$S—, —(CH$_2$)$_2$NHCOCH$_2$SO$_2$—, —COCH$_2$S—, —COCH$_2$O—, —(CH$_2$)$_2$NHCOCH$_2$O—, —CONH(CH$_2$)$_2$S—, or —CONH(CH$_2$)$_2$O—. In a subclass, $X^4$ is —(CH$_2$)$_2$NHCOCH$_2$S—, —CH$_2$NHCOCH$_2$S—, —O(CH$_2$)$_2$S—, —NHCOCH$_2$S—, —COCH$_2$S—, or —CONH(CH$_2$)$_2$S—; and $Ar^2$ is either:

(a) phenyl optionally substituted with one, two, or three groups independently selected from the group consisting of —(C$_{1-6}$)alkyl, cyano, halo, halo-substituted (C$_{1-4}$)alkyl, nitro, —X$^9$NR$^{16}$R$^{16}$, —X$^9$NR$^{16}$C(O)R$^{16}$, —X$^9$C(O)NR$^{16}$R$^{16}$, —X$^9$NR$^{16}$C(O)OR$^{16}$, —X$^9$OC(O)NR$^{16}$R$^{16}$, —X$^9$NR$^{16}$C(O)NR$^{16}$R$^{16}$, —X$^9$NR$^{16}$C(NR$^{16}$)NR$^{16}$R$^{16}$, —X$^9$OR$^{16}$, —X$^9$C(O)R$^{16}$, —X$^9$C(O)OR$^{16}$, —X$^9$OC(O)R$^{16}$, —X$^9$S(O)$_2$NR$^{16}$R$^{16}$, —X$^9$P(O)(OR$^{16}$)OR$^{16}$, —X$^9$OP(O)(OR$^{16}$)OR$^{16}$, —X$^9$SR$^{16}$, —X$^9$S(O)R$^{17}$, —X$^9$S(O)$_2$R$^{17}$ and —X$^9$NR$^7$S(O)$_2$R$^{17}$, wherein $X^9$ is a bond or (C$_{1-6}$) alkylene, R$^{16}$ at each occurrence independently is hydrogen, (C$_{1-6}$)alkyl, or halo-substituted (C$_{1-3}$)alkyl, and R$^{17}$ is (C$_{1-6}$)alkyl, or halo-substituted (C$_{1-3}$)alkyl. In a class phenyl optionally substituted with one, two, or three groups independently selected from the group consisting of methyl, ethyl, isopropyl, tert-butyl, cyano, chloro, fluoro, bromo, trifluoromethyl, —NH$_2$, —NHCH$_3$, —N(CH$_3$)$_2$, nitro, —NHCOCH$_3$, —CONH$_2$, —CONHCH$_3$, —CON(CH$_3$)$_2$, —OH, —OCH$_3$, —OCH$_2$CH$_3$, —COCH$_3$, —COOH, —COOCH$_3$, —OCOCH$_3$, —SCH$_3$, —SO$_2$NH$_2$, —SO$_2$NHCH$_3$, and —SO$_2$N(CH$_3$)$_2$. In a subclass, phenyl optionally substituted with one, two, or three groups independently selected from the group consisting of fluoro, bromo, chloro, methyl, —OCH$_3$, —NHCOCH$_3$, nitro, —N(CH$_3$)$_2$, tert-butyl, trifluoromethyl, —OH, and —SO$_2$CH$_3$; or (b) heteroaryl containing 5, 6 or 9 ring atoms where one, two or three heteroatoms are independently selected from the group consisting of NR (where R is hydrogen or methyl), S, or O and wherein said ring is optionally substituted with —(C$_{1-6}$)alkyl, cyano, halo, halo-substituted (C$_{1-4}$)alkyl, nitro, —X$^9$NR$^{16}$R$^{16}$, —X$^9$NR$^{16}$C(O)R$^{16}$, —X$^9$C(O)NR$^{16}$R$^{16}$, —X$^9$OR$^{16}$, —X$^9$C(O)R$^{16}$, —X$^9$S(O)$_2$NR$^{16}$R$^{16}$, —X$^9$SR$^{16}$, —X$^9$S(O)R$^{17}$, —X$^9$S(O)$_2$R$^{17}$ and —X$^9$NR$^7$S(O)$_2$R$^{17}$, wherein $X^9$ is a bond or (C$_{1-6}$)alkylene, R$^{16}$ at each occurrence independently is hydrogen, (C$_{1-6}$)alkyl, or halo-substituted (C$_{1-3}$)alkyl, and R$^{17}$ is (C$_{1-6}$)alkyl, or halo-substituted (C$_{1-3}$)alkyl. In a class the heteroaryl is imidazolyl, 1-methylimidazol-2-yl, benzoxazol-2-yl, benzthiazol-2-yl, pyrimidin-2-yl, thiazol-4-yl, thienyl, furanyl, oxadiazolyl, or pyridin-4-yl, and is optionally substituted with one, two, or three groups independently selected from the group consisting of methyl, ethyl, isopropyl, tert-butyl, cyano, chloro, fluoro, bromo, trifluoromethyl, —NH$_2$, —NHCH$_3$, —N(CH$_3$)$_2$, nitro, —NHCOCH$_3$, —CONH$_2$, —CONHCH$_3$, —CON(CH$_3$)$_2$, —OH, —OCH$_3$, —OCH$_2$CH$_3$, —COCH$_3$, —COOH, —COOCH$_3$, —OCOCH$_3$, —SCH$_3$, —SO$_2$NH$_2$, —SO$_2$NHCH$_3$, or —SO$_2$N(CH$_3$)$_2$; or (c) heterocycloalkyl of 5 to 6 ring atoms containing one or two heteroatoms independently selected from the group consisting of NR (where R is hydrogen or methyl), S, or O, and which is optionally substituted with —(C$_{1-6}$)alkyl, cyano, halo, halo-substituted (C$_{1-4}$)alkyl, nitro, —X$^9$NR$^{16}$NR$^{16}$, —X$^9$NR$^{16}$C(O)R$^{16}$, —X$^9$C(O)NR$^{16}$R$^{16}$, —X$^9$OR$^{16}$, —X$^9$C(O)R$^{16}$, —X$^9$S(O)$_2$NR$^{16}$R$^{16}$, —N$^9$SR$^{16}$, —X$^9$S(O)R$^{17}$, —X$^9$S(O)$_2$R$^{17}$ and —X$^9$NR$^7$S(O)$_2$R$^{17}$, wherein $X^9$ is a bond or (C$_{1-6}$)alkylene, R$^{16}$ at each occurrence independently is hydrogen, (C$_{1-6}$)alkyl, or halo-substituted (C$_{1-3}$)alkyl, and R$^{17}$ is (C$_{1-6}$)alkyl, or halo-substituted (C$_{1-3}$)alkyl. In a class, the heterocycloalkyl is morpholino, pyrrolidino, piperazino, piperidino, or thiomorpholino which is optionally substituted with one or two groups independently selected from the group consisting of methyl, ethyl, isopropyl, tert-butyl, or tert-butoxycarbonyl.

In a subclass, Ar$^2$—X$^4$—Ar$^1$— is 4-(morpholin-4-yl)phenyl, 4-(1-methylpyrrolidin-2-ylmethoxy)phenyl, 4-(1-methylpiperidin-4-yloxy)phenyl, 4-[2-(morpholin-4-yl-N-oxide)ethoxy]phenyl, 4-(4-thiolphenylsulfanyl)-phenyl, 4-(4-methylpiperazin-1-yl)phenyl, 4-[2-(morpholin-4-yl) ethoxy]phenyl, 4-(4-tert-butoxycarbonylpiperidin-4-yloxy) phenyl, 4-piperidin-4-yloxyphenyl, 4-thien-2-ylphenyl, 4-(3-aminophenyl)phenyl, 4-(pyridin-4-ylsulfanyl)phenyl, 4-(2-phenylethylsulfinyl)phenyl, 4-(4-methoxyphenylsulfanyl)phenyl, 4-[2-(phenyl)ethylsulfanyl]-phenyl, 4-(2-aminophenylsulfanyl)-phenyl, 4-(2-chlorophenylmethylsulfanyl)phenyl, 4-(2-methylphenylmethylsulfanyl)phenyl, 4-(pyridin-2-ylsulfanyl)phenyl, 4-(4-chlorophenylmethylsulfanyl)phenyl, 4-(3-aminophenyl-sulfanyl)-phenyl, 4-(pyridin-3-ylmethylaminocarbonylmethylsulfanyl)phenyl, 4-[2-(2-chloropyridin-3-ylcarbonylamino)ethylsulfanyl]phenyl, 4-(4-aminophenylsulfanyl)phenyl, 4-[2-(pyridin-4-yl-carbonylamino)-ethylsulfanyl]phenyl, 4-(4-dimethylaminophenylmethylamino-carbonylmethylsulfanyl)phenyl, 4-(thien-2-ylsulfanyl)phenyl, 4-(furan-2-ylmethylsulfanyl)-phenyl, 4-(pyridin-4-ylmethylaminocarbonylmethylsulfanyl)phenyl, 4-[2-(furan-2-yl)ethylaminocarbonylmethylsulfanyl)phenyl, 4-[2-(pyridin-4-yl)ethylaminocarbonylmethylsulfanyl]phenyl, 4-(1-methylpiperidin-4ylsulfanyl)phenyl, 4-(2-chlorophenylmethylaminocarbonylmethylsulfanyl)-phenyl, 4-(4-methoxyphenylmethylaminocarbonylmethylsulfanyl) phenyl, 4-(furan-2-ylmethylaminocarbonylmethylsulfanyl) phenyl, 4-(4-chlorophenylmethylaminocarbonyl-methylsulfanyl)phenyl, 3-fluoro-4-(1-methylimidazol-2-ylsulfanyl) phenyl, 4-(3-dimethylaminophenylmethylaminocarbonylmethylsulfanyl) phenyl, 3-fluoro-4-[2-(phenyl)ethylsulfanyl]phenyl, 3-fluoro-4-(pyrimidin-2-ylsulfanyl)phenyl, 4-[2-(pyridin-2-yl)ethylsulfanyl]phenyl, 4-(1-tert-butylpiperazin-1-ylcarbonylmethylsulfanyl)phenyl, 4-[2-(phenyl)ethylsulfonyl]phenyl, 3-fluoro-4-[2-(pyridin-2-yl)ethylsulfanyl]phenyl, 4-(4-tert-butylpiperazin-1-ylcarbonylmethoxy)phenyl, 4-(2-phenylethoxy)phenyl, 4-(thien-2-yl)ethylaminocarbonylmethylsulfonyl]phenyl, 4-[2-(pyridin-2-yl)ethylsulfonyl]phenyl, 3-fluoro-4-[2-(phenyl)ethylsulfonyl]phenyl, 4-[2-(pyridin-4-yl)ethylaminocarbonylmethyl-oxy]phenyl, 4-(3-methyl-[1,3,5]oxadiazol-4-ylmethylamino-carbonylmethylsulfanyl) phenyl, 4-[(2-morpholin-4-ylcarbonylamino)-ethylsulfanyl] phenyl, 4-[2-(pyridin-3-yloxy)ethylsulfanyl]-phenyl, 4-(piperidin-3-ylaminocarbonylmethylsulfanyl)phenyl, 4-[2-(morpholin-4-ylcarbonylamino)-ethyloxy]phenyl, 4-[2-(morpholin-4-yl)ethylaminocarbonyl-methylsulfanyl]-phenyl, 4-[2-(pyridin-2-yl)ethylsulfanyl]phenyl, 4-(4-isopropylpiperazin-4-ylcarbonylmethylsulfanyl)phenyl, 4-(furan-2-ylmethylaminocarbonylmethyl)phenyl, 4-[2-(furan-2-ylmethylaminocarbonyl)-ethyl]phenyl, 4-benzylsulfanylmethylphenyl, 4-(benzylsulfonylmethyl) phenyl, 4-[3-(furan-2-ylmethyl-aminocarbonyl)propyl]phenyl, 4-[2-(pyridin-2-yl)ethylsulfanylmethyl]phenyl, 4-[2-(pyridin-2-yl)ethylsulfonylmethyl]phenyl, 4-(thien-2-ylethylaminocarbonylmethylsulfonyl)-phenyl, or 4-(furan-2-ylmethylaminocarbonyl)phenyl. In a subclass, —Ar$^1$—X$^4$—Ar$^2$ is 4-[2-(pyridin-4-yl)ethylaminocarbonylmethylsulfanyl]phenyl, 4-[2-(morpholin-4-yl)ethylaminocarbonyl-methylsulfanyl] phenyl, 4-[2-(pyridin-2-yl)ethylsulfanyl]phenyl, 4-(2-phenylethylsulfanyl)phenyl, 4-(4-dimethylaminophenylmethylaminocarbonylmethyl-sulfanyl)phenyl, 4-[2-(pyridin-3-yloxy)ethylsulfanyl]phenyl, 4-(4-chlorophenylmethylaminocarbonylmethylsulfanyl)phenyl, 3-fluoro-4-(pyridin-2-ylethylsulfanyl)phenyl, 4-(piperidin-3-ylaminocarbonylmethylsulfanyl)-phenyl, 4-(2-chlorophenylmethylaminocarbonylmethylsulfanyl)phenyl, 4-(pyridin-3-ylmethylamino-carbonylmethylsulfanyl)phenyl, 4-[2-(thien-2-yl)ethylaminocarbonylmethyl-sulfanyl]phenyl, 4-(3-dimethylaminophenylmethylaminocarbonylmethylsulfanyl)phenyl, 4-[2-(pyridin-4-ylcarbonylamino)ethylsulfanyl]phenyl, 4-(4-methoxyphenylmethylaminocarbonylmethylsulfanyl)phenyl, 4-(4-isopropylpiperazin-1-ylcarbonylmethylsulfanyl)phenyl, or 4-(furan-2-ylmethylsulfanyl)phenyl.

(vii) Within the above classes and subclasses (A-D), another subclass of compounds is that wherein:

X$^1$ is —O—, S, or —SO$_2$—, in a class, —SO$_2$—; and

Ar is Ar$^3$—X$^5$—Ar$^2$—X$^4$—Ar$^1$—where Ar$^1$ is phenyl or heteroaryl, preferably phenyl, imidazolyl, 1-methylimidazol-2-yl, benzoxazol-2-yl, benzthiazol-2-yl, pyrimidin-2-yl, thiazol-4-yl, or pyridinyl, in a subclass phenyl;

X$^4$ is selected from the group consisting of a bond, —(C$_{1-6}$)alkylene, —X$^7$NR$^{15}$X$^8$—, —X$^7$NR$^{15}$C(O)X$^8$—, —X$^7$C(O)NR$^{15}$X$^8$—, —X$^7$NR$^{15}$C(O)OX$^8$—, —X$^7$OC(O)NR$^{15}$X$^8$, X$^7$NR$^{15}$C(O)NR$^{15}$X$^8$—, —X$^7$OX$^8$—, —X$^7$C(O)X$^8$, X$^7$C(O)OX$^8$—, —X$^7$OC(O)X$^8$—, —X$^7$S(O)$_2$NR$^{15}$X$^8$—, —X$^7$SX$^8$—, —X$^7$S(O)X$^8$—, —X$^7$S(O)$_2$X$^8$— and —X$^7$NR$^{15}$S(O)$_2$X$^8$—, wherein X$^7$ and X$^8$ independently are a bond or —(C$_{1-6}$)alkylene and R$^{15}$ is hydrogen or —(C$_{1-6}$)alkyl; preferably X$^4$ is a bond, methylene, ethylene, propylene, —CH$_2$NH—, —NHCH$_2$, —NHCO—, —NHCONH—, —CONH—, —NHC(O)O—, —OC(O)NH—, —SO$_2$NH—, —NHSO$_2$—, O, —CH$_2$O—, —OCH$_2$—, —S—, or —SO$_2$—, preferably a bond or —NHCOCH$_2$S—;

Ar$^2$ is either:

(a) phenyl optionally substituted with one, two, or three groups independently selected from the group consisting of —(C$_{1-6}$)alkyl, cyano, halo, halo-substituted (C$_{1-4}$)alkyl, nitro, —X$^9$NR$^{16}$R$^{16}$, —X$^9$NR$^{16}$C(O)R$^{16}$, —X$^9$C(O)NR$^{16}$R$^{16}$, —X$^9$NR$^{16}$C(O)OR$^{16}$, —X$^9$OC(O)NR$^{16}$R$^{16}$, —X$^9$NR$^{16}$C(O)NR$^{16}$R$^6$, —X$^9$NR$^{16}$C(NR$^{16}$)NR$^{16}$R$^6$, —X$^9$OR$^{16}$, —X$^9$C(O)R$^{16}$, —X$^9$C(O)OR$^{16}$, —X$^9$OC(O)R$^{16}$, —X$^9$S(O)$_2$NR$^{16}$R$^{16}$, —X$^9$P(O)(OR$^{16}$)OR$^{16}$, —X$^9$OP(O)(OR$^{16}$)OR$^{16}$, —X$^9$SR$^{16}$, —X$^9$S(O)R$^{17}$, —X$^9$S(O)$_2$R$^{17}$ and —X$^9$NR$^7$S(O)$_2$R$^{17}$, wherein X$^9$ is a bond or (C$_{1-6}$)alkylene, R$^{16}$ at each occurrence independently is hydrogen, (C$_{1-6}$)alkyl, or halo-substituted (C$_{1-3}$)alkyl, and R$^{17}$ is (C$_{1-6}$)alkyl, or halo-substituted (C$_{1-3}$)alkyl. Preferably optionally substituted with one, two, or three groups independently selected from the group consisting of methyl, ethyl, isopropyl, tert-butyl, cyano, chloro, fluoro, bromo, trifluoromethyl, —NH$_2$, —NHCH$_3$, —N(CH$_3$)$_2$, nitro, —NHCOCH$_3$, —CONH$_2$, —CONHCH$_3$, —CON(CH$_3$)$_2$, —OH, —OCH$_3$, —OCH$_2$CH$_3$, —COCH$_3$, —COOH, —COOCH$_3$, —OCOCH$_3$, —SCH$_3$, —SO$_2$NH$_2$, —SO$_2$NHCH$_3$, and —SO$_2$N(CH$_3$)$_2$. In a subclass, optionally substituted with one, two, or three groups independently selected from the group consisting of fluoro, bromo, methyl, —OCH$_3$, —NHCOCH$_3$, nitro, tert-butyl, trifluoromethyl, —OH, and —SO$_2$CH$_3$; or (b) heteroaryl of 5 or 9 ring atoms containing one or two heteroatoms independently selected from the group consisting of NR (where R is hydrogen or methyl), S, or O, preferably imidazolyl, 1-methylimidazol-2-yl, benzoxazol-2-yl, benzthiazol-2-yl, pyrimidin-2-yl, thiazol-4-yl, pyridin-4-yl, and optionally substituted with —(C$_{1-6}$)alkyl, cyano, halo, halo-substituted (C$_{1-4}$)alkyl, nitro, —X$^9$NR$^6$R$^6$, —X$^9$NR$^{16}$C(O)R$^{16}$, —X$^9$C(O)NR$^{16}$R$^{16}$, —X$^9$OR$^{16}$, —X$^9$C(O)R$^{16}$, —X$^9$S(O)$_2$NR$^{16}$R$^{16}$, —X$^9$SR$^{16}$, —X$^9$S(O)R$^{17}$, —X$^9$S(O)$_2$R$^{17}$ and —X$^9$NR$^7$S(O)$_2$R$^{17}$, wherein X$^9$ is a bond or (C$_{1-6}$)alkylene, R$^{16}$ at each occurrence independently is hydrogen, (C$_{1-6}$)alkyl, or halo-substituted (C$_{1-3}$)alkyl, and R$^{17}$ is (C$_{1-6}$)alkyl, or halo-substituted (C$_{1-3}$)alkyl. Preferably, the heteroaryl ring is optionally substituted with one, two, or three groups independently selected from the group consisting of methyl, ethyl, isopropyl, tert-butyl, cyano, chloro, fluoro, bromo, trifluoromethyl, —NH$_2$, —NHCH$_3$, —N(CH$_3$)$_2$, nitro, —NHCOCH$_3$, —CONH$_2$, —CONHCH$_3$, —CON(CH$_3$)$_2$, —OH, —OCH$_3$, —OCH$_2$CH$_3$, —COCH$_3$, —COOH, —COOCH$_3$, —OCOCH$_3$, —SCH$_3$, —SO$_2$NH$_2$, —SO$_2$NHCH$_3$, —SO$_2$N(CH$_3$)$_2$, —SO$_2$NHphenyl, —SO$_2$NHbenzyl, —SO$_2$phenyl, and —SO$_2$benzyl. In a subclass, the heteroaryl ring is optionally substituted with one, two, or three groups independently selected from the group consisting of fluoro, bromo, methyl, —OCH$_3$, —NHCOCH$_3$, nitro, tert-butyl, trifluoromethyl, —OH, and —SO$_2$CH$_3$; or (c) heterocycloalkyl of 5 to 6 ring atoms containing one or two heteroatoms independently selected from the group consisting of NR (where R is hydrogen or methyl), S, or O and is optionally substituted with —(C$_{1-6}$)alkyl, cyano, halo, halo-substituted (C$^{1-4}$)alkyl, nitro, —X$^9$NR$^{16}$R$^{16}$, —X$^9$NR$^{16}$C(O)R$^{16}$, —X$^9$C(O)NR$^{16}$R$^{16}$, —X$^9$OR$^{16}$, —X$^9$C(O)R$^{16}$, —X$^9$S(O)$_2$NR$^{16}$R$^{16}$, —X$^9$SR$^{16}$, —X$^9$S(O)R$^{17}$, —X$^9$S(O)$_2$R$^{17}$ and —X$^9$NR$^7$S(O)$_2$R$^{17}$, wherein X$^9$ is a bond or (C$_{1-6}$)alkylene, R$^{16}$ at each occurrence independently is hydrogen, (C$_{1-6}$)alkyl, or halo-substituted (C$_{1-3}$)alkyl, and R$^{17}$ is (C$_{1-6}$)alkyl, or halo-substituted (C$_{1-3}$)alkyl. Preferably, the heterocycloalkyl ring is pyrrolidino, piperazino, or piperidino and optionally substituted with one, two, or three groups independently selected from the group consisting of methyl, ethyl, isopropyl, tert-butyl, cyano, chloro, fluoro, bromo, trifluoromethyl, —NH$_2$, —NHCH$_3$, —N(C$_3$)$_2$, nitro, —NHCOCH$_3$, —CONH$_2$, —CONHCH$_3$, —CON(CH$_3$)$_2$, —OH, —OCH$_3$, —OCH$_2$CH$_3$, —COCH$_3$, —COOH, —COOCH$_3$, —OCOCH$_3$, —SCH$_3$, —SO$_2$NH$_2$, —SO$_2$NHCH$_3$, —SO$_2$N(CH$_3$)$_2$, —SO$_2$NHphenyl, —SO$_2$NHbenzyl, —SO$_2$phenyl, —SO$_2$benzyl;

X$^5$ is selected from the group consisting of a bond, —(C$_6$)alkylene, —X$^7$NR$^{15}$X$^8$—, —X$^7$NR$^{15}$C(O)X$^8$—, —X$^7$C(O)NR$^{15}$X$^8$—, —X$^7$NR$^{15}$C(O)OX$^8$—, —X$^7$OC(O)NR$^{15}$X$^8$—, —X$^7$NR$^{15}$C(O)NR$^{15}$X$^8$—, X$^7$OX$^8$—, —X$^7$C(O)X$^8$—, —X$^7$C(O)OX$^8$—, —X$^7$OC(O)X$^8$—, —X$^7$S(O)$_2$NR$^{15}$X$^8$—, —X$^7$SX$^8$—, —X$^7$S(O)X$^8$—, —X$^7$S(O)$_2$X$^8$— and —X$^7$NR$^{15}$S(O)$_2$X$^8$—, wherein X$^7$ and X$^8$ independently are a bond or —(C$_{1-6}$)alkylene and R$^{15}$ is hydrogen or —(C$_{1-6}$)alkyl; preferably X$^4$ is a bond, methylene, ethylene, propylene, —CH$_2$NH—, —NHCH$_2$, —NHCO—, —NHCONH—, —CONH—, —NHC(O)O—, —OC(O)NH—, —SO$_2$NH—, —NHSO$_2$—, —O—, —CH$_2$O—, —OCH$_2$—, —S—, or —SO$_2$—; preferably X$^5$ is a bond or —O—; and Ar$^3$ is either:

(a) phenyl optionally substituted with one, two or three groups independently selected from the group consisting of —(C$_{1-6}$)alkyl, cyano, halo, halo-substituted (C$_{1-4}$)alkyl, nitro, —X$^9$NR$^6$R$^{16}$, —X$^9$NR$^{16}$C(O)R$^{16}$, —X$^9$C(O)NR$^6$R$^6$, —X$^9$NR$^{16}$C(O)OR$^{16}$, —X$^9$OC(O)NR$^{16}$R$^{16}$, —X$^9$NR$^{16}$C(O)NR$^{16}$R$^{16}$, —X$^9$NR$^{16}$C(NR$^{16}$)NR$^{16}$R$^{16}$, —X$^9$OR$^{16}$, —X$^9$C(O)R$^{16}$, —X$^9$C(O)OR$^{16}$, —X$^9$OC(O)R$^{16}$, —X$^9$S(O)$_2$NR$^6$R$^6$, —X$^9$P(O)(OR$^{16}$)OR$^{16}$, —X$^9$OP(O)(OR$^{16}$)OR$^{16}$, —X$^9$SR$^{16}$, —X$^9$S(O)R$^{17}$, —X$^9$S(O)$_2$R$^{17}$ and —X$^9$NR$^7$S(O)$_2$R$^7$, wherein X$^9$ is a bond or (C$_{1-6}$)alkylene, R$^{16}$ at each occurrence independently is hydrogen, (C$_{1-6}$)alkyl, or halo-substituted (C$_{1-3}$)alkyl, and R$^{17}$ is (C$_{1-6}$)alkyl, or halo-substituted (C$_{1-3}$)alkyl. Preferably, optionally substituted with one, two, or three groups independently selected from the group consisting of methyl, ethyl, isopropyl, tert-butyl, cyano, chloro, fluoro, bromo, trifluoromethyl, —NH$_2$, —NHCH$_3$, —N(CH$_3$)$_2$, nitro, —NHCOCH$_3$, —CONH$_2$, —CONHCH$_3$, —CON(CH$_3$)$_2$, —OH, —OCH$_3$, —OCH$_2$CH$_3$, —COCH$_3$, —COOH, —COOCH$_3$, —OCOCH$_3$, —SCH$_3$, —SO$_2$NH$_2$, —SO$_2$NHCH$_3$, or —SO$_2$N(CH$_3$)$_2$. In a subclass, optionally substituted with one, two, or three groups independently selected from the group consisting of fluoro, bromo, methyl, —OCH$_3$, —NHCOCH$_3$, nitro, tert-butyl, trifluoromethyl, —OH, or —SO$_2$CH$_3$; or (b) heteroaryl of 5 or 9 ring atoms containing one or two heteroatoms independently selected from the group consisting of NR (where R is hydrogen or methyl), S, or O, preferably imidazolyl, 1-methylimidazol-2-yl, benzoxazol-2-yl, benzthiazol-2-yl, pyrimidin-2-yl, thiazol-4-yl, or pyridin-4-yl, and optionally substituted with —(C$_{1-6}$)alkyl, cyano, halo, halo-substituted (C$_{1-4}$)alkyl, nitro, —X$^9$NR$^{16}$R$^{16}$, —X$^9$NR$^{16}$C(O)R$^{16}$, —X$^9$C(O)NR$^{16}$R$^{16}$, —X$^9$OR$^{16}$, —X$^9$C(O)R$^{16}$, —X$^9$S(O)$_2$NR$^{16}$R$^{16}$, —X$^9$SR$^{16}$, —X$^9$S(O)R$^{17}$, —X$^9$S(O)$_2$R$^{17}$ and —X$^9$NR$^7$S(O)$_2$R$^{17}$, wherein X$^9$ is a bond or (C$_{1-6}$)alkylene, R$^{16}$ at each occurrence independently is hydrogen, (C$_{1-6}$)alkyl, or halo-substituted (C$_{1-3}$)alkyl, and R$^{17}$ is (C$_{1-6}$)alkyl, or halo-substituted (C$_{1-3}$)alkyl. Preferably, optionally substituted with one, two, or three groups independently selected from the group consisting of methyl, ethyl, isopropyl, tert-butyl, cyano, chloro, fluoro, bromo, trifluoromethyl, —NH$_2$, —NHCH$_3$, —N(CH$_3$)$_2$, nitro, —NHCOCH$_3$, —CONH$_2$, —CONHCH$_3$, —CON(CH$_3$)$_2$, —OH, —OCH$_3$, —OCH$_2$CH$_3$, —COCH$_3$, —COOH, —COOCH$_3$, —OCOCH$_3$, —SCH$_3$, —SO$_2$NH$_2$, —SO$_2$NHCH$_3$, —SO$_2$N(CH$_3$)$_2$, —SO$_2$NHphenyl, —SO$_2$NHbenzyl, —SO$_2$phenyl, and —SO$_2$benzyl. In a subclass, optionally substituted with one, two, or three groups independently selected from the group consisting of fluoro, bromo, methyl, —OCH$_3$, —NHCOCH$_3$, nitro, tert-butyl, trifluoromethyl, —OH, and —SO$_2$CH$_3$; or (c) heterocycloalkyl of 5 to 6 ring atoms containing one or two heteroatoms independently selected from the group consisting of NR (where R is hydrogen or methyl), S, or O, morpholino, pyrrolidino, piperazino, piperidino, thiomorpholino, and optionally substituted with —(C$_{1-1}$)alkyl, cyano, halo, halo-substituted (C$_{1-4}$)alkyl, nitro, —X$^9$NR$^{16}$R$^{16}$, —X$^9$NR$^{16}$C(O)R$^{16}$, —X$^9$C(O)NR$^{16}$R$^{16}$, —X$^9$OR$^{16}$, —X$^9$C(O)R$^{16}$, —X$^9$S(O)$_2$NR$^{16}$R$^{16}$, —X$^9$SR$^{16}$, —X$^9$S(O)R$^{17}$, —X$^9$S(O)$_2$R$^{17}$ and —X$^9$NR$^7$S(O)$_2$R$^{17}$, wherein X$^9$ is a bond or (C$_{1-6}$)alkylene, R$^{16}$ at each occurrence independently is hydrogen, (C$_{1-6}$)alkyl, or halo-substituted (C$_{1-3}$)alkyl, and R$^{17}$ is (C$_{1-1}$)alkyl, or halo-substituted (C$_{1-3}$)alkyl. Preferably, optionally substituted with one, two, or three groups independently selected from the group consisting of methyl, ethyl, isopropyl, tert-butyl, cyano, chloro, fluoro, bromo, trifluoromethyl, —NH$_2$, —NHCH₃, —N(CH₃)₂, nitro, —NHCOCH₃, —CONH₂, —CONHCH₃, —CON(CH₃)₂, —OH, —OCH₃, —OCH₂CH₃, —COCH₃, —COOH, —COOCH₃, —OCOCH₃, —SCH₃, —SO₂NH₂, —SO₂NHCH₃, —SO₂N(CH₃)₂, —SO₂NHphenyl, —SO₂NHbenzyl, —SO₂phenyl, and —SO₂benzyl. In a subclass, optionally substituted with one, two, or three groups independently selected from the group consisting of fluoro, bromo, methyl, —OCH₃, —NHCOCH₃, nitro, tert-butyl, trifluoromethyl, —OH, and —SO₂CH₃.

Most preferably, Ar³—X⁵—Ar²—X⁴—Ar¹— is 4-[2-(4-isopropylpiperazin-1-yl)thiazol-4-yl]phenyl, 4-[4-(tert-butoxycarbonylpiperazin-1-yl)phenyl]phenyl, 4-[4-(piperazin-1-yl)phenyl]phenyl, 4-[4-(morpholin-4-yl)piperidin-1-yl]phenyl, 4-[4-(piperidin-1-yloxy)phenyl]phenyl, 4-[4-(pyridin-4-yl)piperazin-1-ylcarbonylmethylsulfanyl]phenyl, 4-[4-(pyridin-2-yl)piperazin-1-ylcarbonylmethylsulfanyl]phenyl, 4-[4-(pyrimidin-2-yl)piperazin-1-ylcarbonylmethylsulfanyl]phenyl, 4-[4-(4-bromophenyl)piperazin-1-ylcarbonylmethylsulfanyl]-phenyl, or 4-[4-benzylpiperidin-4-ylaminocarbonylmethylsulfanyl]phenyl. Particularly preferably, Ar³—X⁵—Ar²—X⁴—Ar¹— is 4-[4-(piperazin-1-yl)phenyl]phenyl, 4-[4-(pyridin-4-yl)piperazin-1-ylcarbonylmethylsulfanyl]phenyl, 4-[4-(piperidin-1-yloxy)phenyl]phenyl, or 4-[4-benzylpiperidin-4-ylaminocarbonylmethylsulfanyl]phenyl.

(E) Another preferred group of compounds of Formula I is that wherein:

R¹, R², R³, R⁴ and R⁵ are hydrogen;

R⁶ and R⁶ᵃ together with the carbon atoms to which they are attached form (C₃₋₇)monocyclic cycloalkylene; (C₇₋₈) bridged polycyclic cycloalkylene; C₃₋₇) monocyclic cycloalkenylene; or (C₇₋₈) spirocycloalkylene where monocycloalkylene is optionally substituted with alkyl. Preferably R⁶ and R⁶ᵃ together with the carbon atoms to which they are attached form:

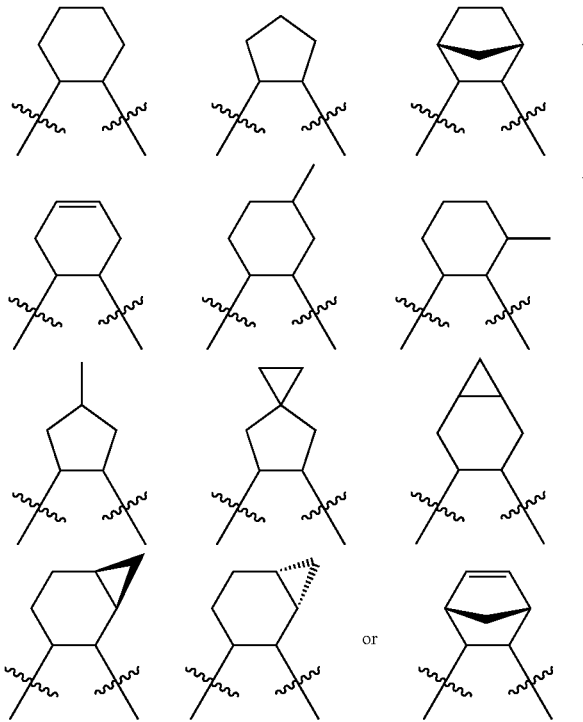

or

X¹ is —S—, or —SO₂—; and

Ar is:

(i) phenyl substituted with one or two substituents independently selected from (C₁₋₆)alkyl, cyano, halo, halo-substituted (C₁₋₄)alkyl, nitro, —X⁹NR¹⁶R⁶, —C(O)R¹⁶, —NR¹⁶C(O)R¹⁶, —X⁹OR¹⁶, —X⁹C(O)OR¹⁶, —SR¹⁶, —S(O)₂R¹⁷, —OS(O)₂R¹⁷ and —NR⁷S(O)₂R¹⁷ where X⁹ is a bond or (C₁₋₆)alkylene, R¹⁶ at each occurrence independently is hydrogen, (C₁₋₆)alkyl, or halo-substituted (C₁₋₃) alkyl, and R¹⁷ is (C₁₋₆)alkyl, or halo-substituted (C₁₋₃)alkyl; or (ii) phenyl substituted with heteroalkyl, preferably phenyl substituted with ethoxycarbonylmethylsulfanyl, 3-hydroxypropylsulfanyl, 2-aminoethylsulfanyl, 2-tert-butoxycarbonylaminoethylsulfanyl, 2-(2,2,2-trifluoroethylamino)ethylsulfanyl, 3-dimethylaminopropyloxy, methylaminocarbonylmethyl-sulfanyl, 2-(acetylamino)ethoxy, 2-aminoethylsulfanyl, 2-(acetylamino)ethylsulfanyl, 2-(ethylsulfonylamino)ethylsulfanyl, 2-(dimethylaminosulfonylamino)-ethylsulfanyl, 2-(methylsulfonyloxy)ethylsulfanyl, 2-hydroxyethylsulfanyl, methoxycarbonylmethoxy, 1-ethoxycarbonylethylsulfanyl, trifluoromethylsulfonyloxy, or 2-bromoethylsulfanyl. In a subclass phenyl substituted at the 4-position with 2-aminoethylsulfanyl, 2-(methylsulfonyloxy)ethylsulfanyl, 2-tert-butoxycarbonylaminoethyl-sulfanyl, or 2-bromoethylsulfanyl; or (iii) Ar²—X⁴—Ar¹— where Ar¹ is phenyl, X⁴ is selected from the group consisting of a bond, —X⁷NR¹⁵C(O)X⁸—, —X⁷OX⁸—, —X⁷SX⁸—, —X⁷S(O)X⁵—, and —X⁷S(O)₂X⁸— wherein X⁷ and X⁸ independently are a bond or —(C₁₋₆)alkylene and R¹⁵ is hydrogen or —(C₁₋₆)alkyl; preferably X⁴ is a bond, —CH₂NHCO—, —CH₂NHCO(CH₂)₃—, H₂NHCOCH₂—, —CH₂NHCO(CH₂)₂—, —O—, —CH₂O—, —(CH₂)₂O—, —S—, —(CH₂)₂S—, —CH₂S—, —(CH₂)₂SO—, —(CH₂)₂SO₂—, —CH₂SO₂CH₂—, —(CH₂)₂SO₂CH₂—, —(CH₂)₂SCH₂—, or —CH₂SCH₂—; preferably X⁴ is a bond, —CH₂S—, or —(CH₂)₂S—; or X⁴ is heteroalkylene, preferably —CH₂NHCOCH₂S—, —(CH₂)₂NHCOCH₂S—, —CONH(CH₂)₂S—, —NHCOCH₂S—, 4)(CH₂)₂S—, —(CH₂)₂NHCOCH₂SO₂—, —COCH₂S—, —COCH₂O—, —(CH₂)₂NHCOCH₂O—, —CONH(CH₂)₂S—, or —CONH(CH₂)₂O—. In a subclass X⁴ is —(CH₂)₂NHCOCH₂S—, —CH₂NHCOCH₂S—, —O(CH₂)₂S—, —NHCOCH₂S—, —COCH₂S—, or —CONH(CH₂)₂S—; and Ar² is phenyl optionally substituted with (C₁)alkyl, —OR¹⁶, halo, or —NR¹⁶R¹⁶; or heteroaryl containing five or six ring atoms wherein one, two or three rings atoms are heteroatoms selected from the group consisting of nitrogen, oxygen or sulfur and wherein the heteroaryl ring is optionally substituted with a group selected from halo; or heterocycloalkyl ring of six ring atoms wherein one or two ring atoms are independently selected from nitrogen or oxygen and wherein said heterocycloalkyl ring is optionally substituted with a substituent selected from (C₁₋₆)alkyl, or —OC(O)R¹⁶ where R¹⁶ at each occurrence independently is hydrogen, (C₁₋₆)alkyl, or halo-substituted (C₁₋₃)alkyl; or (iv) Ar³—X⁵—Ar²—X⁴—Ar¹— where Ar¹ is phenyl; X⁴ is bond or —COCH₂S—; Ar² is 5 or 6 membered heteroaryl ring containing one or two heteroatoms selected from nitrogen or sulfur or 6 membered heterocycloalkyl ring containing one or two nitrogen atoms; $X^5$ is bond, —O—, or alkylene; and $Ar^3$ is phenyl optionally substituted with halo; a 6 membered heterocycloalkyl ring containing one or two nitrogen atoms and optionally substituted with $(C_{1-6})$alkyl, or —OC(O)$R^{16}$ where $R^{16}$ at each occurrence independently is hydrogen, $(C_{1-6})$alkyl, or halo-substituted $(C_{1-3})$alkyl; or a 5 or 6 membered heteroaryl ring containing one or two heteroatoms selected from nitrogen or sulfur.

In a subclass, Ar is 4-fluorophenyl, 4-bromophenyl, 4-chlorophenyl, 4-methylphenyl, 4-methoxyphenyl, 4-(-NHCOCH$_3$)phenyl, 4-nitrophenyl, 4-trifluoromethylphenyl, 4-tert-butylphenyl, 4-trifluoromethylphenyl, 4-methylsulfanylphenyl, 4-methylsulfonylphenyl, 4-hydroxyphenyl, 4-aminophenyl, 2-chlorophenyl, 2,4-dichlorophenyl, 2,5-dichlorophenyl, 2-methylphenyl, 3,4-dichlorophenyl, 3,5-dichlorophenyl, 3-chlorophenyl, 4-dimethylaminophenyl, 3-methylphenyl, 4-trifluoromethoxyphenyl, 3-methoxyphenyl, 3,4-dimethoxyphenyl, 2,5-dimethoxyphenyl, 4-thiolphenyl, 4-isopropyloxyphenyl, 3-trifluoromethylphenyl, 3-(—NHCOCH$_3$)phenyl, 3-fluorophenyl, 3-aminophenyl, 3-carboxymethylphenyl, 4-carboxyphenyl, 3-hydroxyphenyl, 3-formylaminophenyl, 3-trifluoroacetylaminophenyl, 4-hydroxymethylphenyl, 4-trifluorosulfonyloxyphenyl, 3-carboxylphenyl, 4-ethylsulfanylphenyl, 3-methylsulfonylaminophenyl, 3,4-dimethylsulfanylphenyl, 3,4-difluorophenyl, 4-tert-butylsulfanylphenyl, 2,4-difluorophenyl, 3-fluoro-4-methylsulfanylphenyl, 4-(3-carboxypropyl)phenyl, 4-(2-carboxyethyl)phenyl, 4-carboxymethyl-phenyl, 4-iodophenyl, 4-(2,2,2-trifluoroethylsulfanyl)phenyl, 4-difluoromethoxyphenyl, 4-difluoromethylsulfanylphenyl, 4-ethoxycarbonylmethylsulfanylphenyl, 3-hydroxypropylsulfanylphenyl, 2-aminoethylsulfanylphenyl, 4-(2-tert-butoxycarbonylaminoethylsulfanyl)phenyl, 4-[2-(2,2,2-trifluoroethylamino)-ethylsulfanyl]phenyl, 4-methylaminocarbonylmethylsulfanylphenyl, 4-[2-(acetylamino)ethoxy]-phenyl, 4-[2-aminoethylsulfanyl]phenyl, 4-[2-(acetylamino)ethylsulfanyl]phenyl, 3-fluoro-4-[2-(ethylsulfonylamino)ethylsulfanyl]phenyl, 3-fluoro-4-[2-(dimethylaminosulfonylamino)-ethylsulfanyl]phenyl, 4-[2-(methylsulfonyloxy)ethylsulfanyl]phenyl, 4-[2-hydroxyethyl-sulfanyl]phenyl, 4-methoxycarbonylmethoxyphenyl, 4-[1-ethoxycarbonylethylsulfanyl]phenyl, 4-trifluoromethylsulfonyloxyphenyl, or 4-[2-bromoethylsulfanyl]phenyl, 4-(morpholin-4-yl)phenyl, 4-(1-methylpyrrolidin-2-ylmethoxy)phenyl, 4-(1-methylpiperidin-4-yloxy)phenyl, 4-[2-(morpholin-4-yl-N-oxide)ethoxy]phenyl, 4-(4-thiolphenylsulfanyl)-phenyl, 4-(4-methylpiperazin-1-yl)phenyl, 4-[2-(morpholin-4-yl)ethoxy]phenyl, 4-(4-tert-butoxycarbonylpiperidin-4-yloxy)phenyl, 4-piperidin-4-yloxyphenyl, 4-thien-2-ylphenyl, 4-(3-aminophenyl)phenyl, 4-(pyridin-4-ylsulfanyl)phenyl, 4-(2-phenylethylsulfinyl)phenyl, 4-(4-methoxyphenylsulfanyl)phenyl, 4-[2-(phenyl)ethylsulfanyl]-phenyl, 4-(2-aminophenylsulfanyl)-phenyl, 4-(2-chlorophenyl-methylsulfanyl)phenyl, 4-(2-methylphenylmethylsulfanyl)phenyl, 4-(pyridin-2-ylsulfanyl)phenyl, 4-(4-chlorophenylmethylsulfanyl)phenyl, 4-(3-aminophenyl-sulfanyl)-phenyl, 4-(pyridin-3-ylmethylaminocarbonylmethylsulfanyl)phenyl, 4-[2-(2-chloropyridin-3-ylcarbonylamino)ethyl-sulfanyl]phenyl, 4-(4-aminophenylsulfanyl)phenyl, 4-[2-(pyridin-4-ylcarbonylamino)-ethylsulfanyl]phenyl, 4-(4-dimethylaminophenylmethylaminocarbonylmethylsulfanyl)phenyl, 4-(thien-2-ylsulfanyl)phenyl, 4-(furan-2-ylmethylsulfanyl)-phenyl, 4-(pyridin-4-ylmethylaminocarbonylmethylsulfanyl) phenyl, 4-[2-(furan-2-yl)ethylaminocarbonylmethylsulfanyl)phenyl, 4-[2-(pyridin-4-yl)ethylaminocarbonylmethylsulfanyl]phenyl, 4-(1-methylpiperidinylsulfanyl)phenyl, 4-(2-chlorophenylmethylamino-carbonylmethylsulfanyl)-phenyl, 4-(4-methoxyphenylmethylaminocarbonylmethylsulfanyl)-phenyl, 4-(furan-2-ylmethylamino-carbonylmethylsulfanyl)phenyl, 4-(4-chlorophenylmethylaminocarbonyl-methylsulfanyl)phenyl, 3-fluoro-4-(1-methylimidazol-2-ylsulfanyl)phenyl, 4-(3-dimethylaminophenylmethylaminocarbonylmethylsulfanyl)phenyl, 3-fluoro-4-[2-(phenyl)ethylsulfanyl]phenyl, 3-fluoro-4-(pyrimidin-2-ylsulfanyl)phenyl, 4-[2-(pyridin-2-yl)ethylsulfanyl] phenyl, 4-(1-tert-butylpiperazin-1-ylcarbonylmethylsulfanyl)phenyl, 4-[2-(phenyl)ethylsulfonyl]phenyl, 3-fluoro-4-[2-(pyridin-2-yl)ethylsulfanyl]phenyl, 4-(4-tert-butylpiperazin-1-ylcarbonylmethoxy)phenyl, 4-(2-phenylethoxy) phenyl, 4-[2-(thien-2-yl)ethylaminocarbonylmethylsulfonyl]phenyl, 4-[2-(pyridin-2-yl)ethylsulfonyl]phenyl, 3-fluoro-4-[2-(phenyl)ethylsulfonyl]phenyl, 4-[2-(pyridin-4-yl)ethylaminocarbonylmethyl-oxy]phenyl, 4-(3-methyl-[1,3,5]oxadiazol-4-ylmethylamino-carbonylmethylsulfanyl)phenyl, 4-[(2-morpholin-4-ylcarbonylamino)-ethylsulfanyl]phenyl, 4-[2-(pyridin-3-yloxy)ethylsulfanyl]-phenyl, 4-(piperidin-3-ylaminocarbonylmethylsulfanyl)phenyl, 4-[2-(morpholin-4-ylcarbonylamino)-ethyloxy]phenyl, 4-[2-(morpholin-4-yl)ethylaminocarbonyl-methylsulfanyl]-phenyl, 4-[2-(pyridin-2-yl)ethylsulfanyl]phenyl, 4-(4-isopropylpiperazin-4-ylcarbonylmethylsulfanyl) phenyl, 4-(furan-2-ylmethylaminocarbonylmethyl) phenyl, 4-[2-(furan-2-ylmethylaminocarbonyl)-ethyl] phenyl, 4-benzylsulfanylmethylphenyl, 4-(benzylsulfonyl-methyl)phenyl, 4-[3-(furan-2-ylmethylaminocarbonyl)propyl]phenyl, 4-[2-(pyridin-2-yl) ethylsulfanylmethyl]phenyl, 4-[2-(pyridin-2-yl)ethylsulfonylmethyl]phenyl, 4-(thien-2-ylethylaminocarbonylmethylsulfonyl)-phenyl, or 4-(furan-2-ylmethylaminocarbonyl)phenyl, 4-[2-(4-isopropylpiperazin-1-yl)thiazol-4-yl]phenyl, 4-[4-(tert-butoxycarbonylpiperazin-1-yl)-phenyl]phenyl, 4-[4-(piperazin-1-yl)phenyl]phenyl, 4-[4-(morpholin-4-yl)piperidin-1-yl]phenyl, 4-[4-(piperidin-1-yloxy)phenyl] phenyl, 4-[4-(pyridin-4-yl)piperazin-1-ylcarbonylmethylsulfanyl]phenyl, 4-(pyridin-2-yl)piperazin-1-ylcarbonylmethylsulfanyl]phenyl, 4-[4-(pyrimidin-2-yl)piperazin-1-ylcarbonylmethylsulfanyl]phenyl, 4-[4-(4-bromophenyl)piperazin-1-ylcarbonylmethylsulfanyl]-phenyl, or 4-[4-benzylpiperidin-4-ylaminocarbonyl-methylsulfanyl]phenyl. In a subclass, Ar is 4-[2-(pyridin-4yl)ethylamino-carbonylmethylsulfanyl] phenyl, 4-[2-(morpholin-4-yl)ethylaminocarbonyl-methylsulfanyl]phenyl, 4-[2-(pyridin-2-yl) ethylsulfanyl]phenyl, 4-(2-phenylethylsulfanyl)phenyl, 4-dimethylaminophenylmethylaminocarbonylmethyl-sulfanyl)phenyl, 4-[2-(pyridin-3-yloxy)ethylsulfanyl]phenyl, 4-(4-chlorophenylmethylaminocarbonylmethylsulfanyl)phenyl, 3-fluoro-4-(pyridin-2-ylethylsulfanyl)phenyl, 4-(piperidin-3-ylaminocarbonylmethylsulfanyl)-phenyl, 4-(2-chlorophenylmethylamino-carbonylmethylsulfanyl) phenyl, 4-(pyridin-3-ylmethylamino-carbonylmethyl-sulfanyl) phenyl, 4-[2-(thien-2-yl)ethylaminocarbonyl-methyl-sulfanyl]phenyl, 4-(3-dimethylaminophenyl-methylaminocarbonylmethylsulfanyl)phenyl, 4-[2-(pyridin-4-ylcarbonylamino)ethylsulfanyl]phenyl, 4-(4-methoxyphenylmethylaminocarbonylmethylsulfanyl) phenyl, 4-(4-isopropylpiperazin-1-ylcarbonylmethylsulfanyl)phenyl, 4-(furan-2-ylmethylsulfanyl)phenyl, 4-hydroxyphenyl, 4-methylsulfanylphenyl, 4-[2-aminoethyl-sulfanyl] phenyl, 4-[2-(methylsulfonyloxy)ethylsulfanyl]-phenyl, 4-[2-tert-butoxycarbonyl-aminoethylsulfanyl]phenyl, or 4-[2-bromoethylsulfanyl]phenyl, 4-[4-(piperazin-1-yl)phenyl]-phenyl, 4-[4-(pyridin-4-yl) piperazin-1-ylcarbonylmethylsulfanyl]-phenyl, 4-[4-(piperidin-1-yloxy)phenyl]phenyl, or 4-[4-benzylpiperidin-4-ylaminocarbonyl-methylsulfanyl] phenyl.

Reference to the preferred embodiments set forth above is meant to include all combinations of particular and preferred groups.

Nonlimiting examples of e compounds of Formula I are listed below.
1. trans-N-cyanomethyl-2-(4-fluorophenylsulfanylmethyl) cyclohexanecarboxamide MS [ESI, (M−1)⁻] m/z=305.2;
2. trans-N-cyanomethyl-2-[4-(4-piperazin-1-yl)phenyl)phenylsulfanylmethyl)-cyclohexanecarboxamide;
3. trans-N-cyanomethyl-2-(4-bromophenylsulfanylmethyl)-cyclohexanecarboxamide;
4. trans-N-cyanomethyl-2-(4-bromophenylsulfinylmethyl) cyclohexanecarboxamide;
5. trans-N-cyanomethyl-2-(4-bromobenzenesulfonylmethyl)cyclohexanecarboxamide;
6. trans-N-cyanomethyl-2-(phenylsulfanylmethyl)cyclohexanecarboxamide;
7. trans-N-cyanomethyl-2-(4-chlorophenylsulfanylmethyl) cyclohexanecarboxamide;
8. trans N-cyanomethyl-2-(3,4-dichlorophenylsulfanylmethyl)cyclohexanecarboxamide;
9. trans-N-cyanomethyl-2-(4-methylphenylsulfanylmethyl) cyclohexanecarboxamide;
10. trans-N-cyanomethyl-2-(4-methoxyphenylsulfanylmethyl)cyclohexanecarboxamide;
11. trans-N-cyanomethyl-2-[4-(morpholin-4-yl)phenylsulfanylmethyl]-cyclohexanecarboxamide;
12. trans-N-cyanomethyl-2-[4-(morpholin-4-yl)benzenesulfonylmethyl]-cyclohexane-carboxamide;
13. trans-N-cyanomethyl-2-(4-methylcarbonylaminophenylsulfanylmethyl)-cyclohexane-carboxamide;
14. trans-N-cyanomethyl-2-(benzenesulfonylmethyl)cyclohexanecarboxamide;
15. trans-N-cyanomethyl-2-(4-chlorobenzenesulfonylmethyl)cyclohexanecarboxamide;
16. trans-N-cyanomethyl-2-(3,4-dichlorobenzenesulfonylmethyl)cyclohexanecarboxamide;
17. trans-N-cyanomethyl-2-(4-methylbenzenesulfonylmethyl)cyclohexanecarboxamide;
18. trans-N-cyanomethyl-2-(4-methoxybenzenesulfonylmethyl)cyclohexanecarboxamide;
19. trans-N-cyanomethyl-2-(4-nitrophenylsulfanyl)cyclohexanecarboxamide;
20. trans-N-cyanomethyl-2-(4-tert-butylphenylsulfanylmethyl)cyclohexanecarboxamide.
21. trans-N-cyanomethyl-2-(4-trifluoromethylphenylsulfanylmethyl)-cyclohexane-carboxamide;
22. trans-N-cyanomethyl-2-(4-methylsulfanylphenylsulfanylmethyl)-cyclohexane-carboxamide;
23. trans-N-cyanomethyl-2-(4-fluorobenzenesulfonylmethyl)cyclohexanecarboxamide [APCI, (M−1)⁻] m/z 337.1;
24. trans-N-cyanomethyl-2-(4-methylcarbonylaminobenzenesulfonylmethyl)-cyclohexane-carboxamide;
25. trans-N-cyanomethyl-2-(4-nitrobenzenesulfonylmethyl) cyclohexanecarboxamide;
26. trans-N-cyanomethyl-2-(4-tert-butylbenzenesulfonylmethyl)cyclohexanecarboxamide;
27. trans-N-cyanomethyl-2-(4-methylsulfonylbenzenesulfonylmethyl)-cyclohexanecarboxamide;
28. trans-N-cyanomethyl-2-(4-hydroxyphenylsulfanylmethyl)cyclohexanecarboxamide;
29. trans-N-cyanomethyl-2-(1-methylimidazol-2-ylsulfanylmethyl)cyclohexanecarboxamide;
30. trans-N-cyanomethyl-2-(4-aminobenzenesulfonylmethyl)cyclohexanecarboxamide;
31. trans-N-cyanomethyl-2-(benzothiazol-2-ylsulfanylmethyl)cyclohexanecarboxamide;
32. trans-N-cyanomethyl-2-(benzoxazol-2-ylsulfanylmethyl)cyclohexanecarboxamide;
33. trans-N-cyanomethyl-2-(4,5-dihydrothiazol-2-ylsulfanylmethyl)-cyclohexanecarboxamide;
34. trans-N-cyanomethyl-2-(4-trifluoromethylbenzenesulfonylmethyl)-cyclohexane-carboxamide;
35. trans-N-cyanomethyl-2-(pyrimidin-2-ylsulfanylmethyl) cyclohexanecarboxamide;
36. trans-N-cyanomethyl-2-(4-hydroxybenzenesulfonylmethyl)cyclohexanecarboxamide;
37. trans-N-cyanomethyl-2-(1-methylimidazol-2-ylsulfonylmethyl)cyclohexanecarboxamide;
38. trans-N-cyanomethyl-2-{4-[2-(4-isopropylpiperazin-1-yl]thiazol-4-yl]benzene-sulfonylmethyl}cyclohexanecarboxamide;
39. trans-N-cyanomethyl-2-(pyridin-4-ylsulfanylmethyl)-cyclohexanecarboxamide;
40. trans-N-cyanomethyl-2-(6-chlorobenzoxazol-2-ylsulfanylmethyl)-cyclohexane-carboxamide;
41. trans-N-cyanomethyl-2-(5-methoxybenzothiazol-2-ylsulfanylmethyl)-cyclohexane-carboxamide;
42. trans-N-cyanomethyl-2-(4-methoxybenzylsulfanylmethyl)-cyclohexanecarboxamide;
43. trans-N-cyanomethyl-2-[4-(4-thiolphenylsulfanyl)phenylsulfanylmethyl)-cyclohexanecarboxamide;
44. trans-N-cyanomethyl-2-{4-[4-(4-tert-butoxycarbonylpiperazin-1-yl)phenyl]-phenylsulfanylmethyl}cyclohexanecarboxamide
45. trans-N-cyanomethyl-2-(2-pyridin-4-yl-1,3,4-oxadiazol-5-ylsulfanylmethyl)-cyclohexanecarboxamide;
46. trans-N-cyanomethyl-2-(4-pyridin-4-ylsulfonylmethyl) cyclohexanecarboxamide;
47. trans-N-cyanomethyl-2-(2,4-dichlorobenzylsulfanylmethyl)cyclohexanecarboxamide;
48. trans-N-cyanomethyl-2-(2,4-dichlorophenylsulfanylmethyl)cyclohexanecarboxamide;
49. trans-N-cyanomethyl-2-[4-(1-methylpyrrolidin-2-ylmethyloxy)phenylsulfanylmethyl]-cyclohexanecarboxamide; ¹HNMR (dmso-d₆): δ 8.65 (1H, m), 7.23 (2H, d, J:8.0 Hz), 6.98 (2H, d, J:8.0 Hz), 4.10 (2H, m), 3.80 (2H, m), 3.4 (6H, m), 2.86 (1H, m), 2.45 (1H, m), 2.05 (3H, m), 1.65 (3H, m), 1.10 (8H, m). LC/MS, M+1: 401.9;
50. trans-N-cyanomethyl-2-(4-dimethylaminophenylsulfanylmethyl)cyclohexanecarboxamide;

51. trans-N-cyanomethyl-2-(4-dimethylaminobenzenesulfonylmethyl)-cyclohexane-carboxamide;
52. trans-N-cyanomethyl-2-(4-trifluoromethoxyphenylsulfanylmethyl)-cyclohexane-carboxamide;
53. trans-N-cyanomethyl-2-(3,4-dimethoxyphenylsulfanylmethyl)-cyclohexanecarboxamide;
54. trans-N-cyanomethyl-2-[4-(1-methylpiperidin-4-yloxy)phenylsulfanylmethyl]-cyclohexanecarboxamide;
55. trans-N-cyanomethyl-2-[4-(3-dimethylaminopropyloxy)phenylsulfanylmethyl]-cyclohexanecarboxamide;
56. trans-N-cyanomethyl-2-[4-(2-morpholin-4-ylethyloxy)benzenesulfonylmethyl]-cyclohexanecarboxamide N-oxide;
57. trans-N-cyanomethyl-2-[4-(1-methylpiperazin-4-yl)benzenesulfonylmethyl]-cyclohexanecarboxamide;
58. trans-N-cyanomethyl-2-[4-(4-morpholin-4-ylpiperidin-1-yl)benzenesulfonylmethyl]-cyclohexanecarboxamide;
59. trans-N-cyanomethyl-2-(4-methoxyphenylsulfanylmethyl)-cyclopentanecarboxamide MS [ESI, (M−H)$^-$] m/z=303.2;
60. trans-N-cyanomethyl-2-[4-(4-tert-butoxypiperidin-4-yloxy)phenylsulfanylmethyl]-cyclohexanecarboxamide;
61. trans-N-cyanomethyl-2-[4-(4-tert-butoxypiperidin-4-yloxy)benzenesulfonylmethyl]-cyclohexanecarboxamide;
62. trans-N-cyanomethyl-6-(4-fluorobenzenesulfonylmethyl)cyclohex-3-enecarboxamide MS [ESI, (M−H)$^-$] m/z=335.0;
63. trans-N-cyanomethyl-2-(cyclohexylsulfanylmethyl)-cyclohexanecarboxamide;
64. trans-N-cyanomethyl-6-(4-methylsulfanylbenzenesulfonylmethyl)cyclohex-3-ene-carboxamide MS [APCI, (M−H)$^-$] m/z=362.9;
65. trans-N-cyanomethyl-2-(3-carboxymethylphenylsulfanylmethyl)-cyclohexanecarboxamide MS [APCI, (M−H)$^-$] m/z=345.1;
66. trans-N-cyanomethyl-2-(4-thien-3-ylbenzenesulfonylmethyl)cyclohexanecarboxamide;
67. trans-N-cyanomethyl-2-(3-trifluoroacetylaminophenylsulfanylmethyl)-cyclohexanecarboxamide MS [ESI, (M−H)$^-$] m/z=398.1;
68. trans-N-cyanomethyl-2-(3-methylsulfonylaminophenylsulfanylmethyl)-cyclohexanecarboxamide MS [ESI, (M−H)$^-$] m/z=380.1;
69. trans-N-cyanomethyl-2-(4-ethoxycarbonylmethylsulfanylbenzenesulfonylmethyl)-cyclohexanecarboxamide;
70. (1S/R,3R/S,4S/R,6R/S)-4-(4-methylsulfanylphenylsulfanylmethyl)bicyclo[4.1.0]heptane-3-carboxylic acid cyanomethylamide MS [ESI, (M−H)$^-$] m/z=345.2;
71. trans-N-cyanomethyl-2-[4-(4-piperidin-4-yloxyphenyl)benzenesulfonylmethyl]-cyclohexanecarboxamide $^1$HNMR (dmso-d$_6$): δ 8.50 (1H, m), 7.70 (4H, m), 7.63 (2H, m), 7.00 (2H, m), 4.34 (1H, m), 3.99 (2H, m), 3.26 (5H, m), 3.18 (1H, m), 2.93 (1H, m), 2.22 (3H, s), 2.00 (7H, m), 1.60 (3H, m), 1.10 (4H, m). LC/MS, M+1: 496.4;
72. trans-N-cyanomethyl-2-[4-(3-aminophenyl)benzenesulfonylmethyl]-cyclohexanecarboxamide;
73. trans-N-cyanomethyl-2-[4-(pyridin-4-ylsulfanyl)benzenesulfonylmethyl]-cyclohexanecarboxamide;
74. trans-N-cyanomethyl-2-[4-(2-phenylethylsulfinyl)benzenesulfonylmethyl]-cyclohexanecarboxamide;
75. trans-N-cyanomethyl-2-[4-(2-phenylethylsulfanyl)benzenesulfonylmethyl]-cyclohexanecarboxamide;
76. trans-N-cyanomethyl-2-[4-(2-aminoethylsulfanyl)benzenesulfonylmethyl]-cyclohexanecarboxamide;
77. trans-N-cyanomethyl-2-[4-(2-chlorophenylmethylsulfanyl)benzenesulfonylmethyl]-cyclohexanecarboxamide;
78. trans-N-cyanomethyl-2-[4-(2-tert-butoxycarbonylaminoethylsulfanyl)benzenesulfonylmethyl]cyclohexanecarboxamide;
79. trans-N-cyanomethyl-2-[4-(2-(2,2,2-trifluoroethylamino)ethylsulfanyl)benzenesulfonyl-methyl]-cyclohexanecarboxamide;
80. trans-N-cyanomethyl-2-[4-(pyridin-3-ylmethylaminocarbonylmethylsulfanyl)benzene-sulfonylmethyl]-cyclohexanecarboxamide;
81. trans-N-cyanomethyl-2-[4-(2-(2-chloropyridin-3-ylcarbonylamino)ethylsulfanyl)-benzenesulfonylmethyl]-cyclohexanecarboxamide;
82. trans-N-cyanomethyl-2-[4-(2-pyridin-4-ylcarbonylaminoethylsulfanyl)benzenesulfonylmethyl]cyclohexanecarboxamide;
83. trans-N-cyanomethyl-2-[4-(2-acetylaminoethyloxy)benzenesulfonylmethyl]-cyclohexanecarboxamide;
84. trans-N-cyanomethyl-2-[4-(4-dimethylaminophenylmethylaminocarbonylmethylsulfanyl)benzenesulfonylmethyl]-cyclohexanecarboxamide trifluoroacetate salt LC/MS: M+1: 543.3;
85. trans-N-cyanomethyl-2-[3-fluoro-4-(2-aminoethylsulfanyl)benzenesulfonylmethyl]-cyclohexanecarboxamide;
86. trans-N-cyanomethyl-2-[4-(pyridin-4-ylmethylaminocarbonylmethylsulfanyl)benzene-sulfonylmethyl]-cyclohexanecarboxamide;
87. trans-N-cyanomethyl-2-[4-(2-thien-2-ylethylaminocarbonylmethylsulfanyl)-benzenesulfonylmethyl]-cyclohexanecarboxamide;
88. trans-N-cyanomethyl-2-[4-(2-pyridin-4-ylethylaminocarbonylmethylsulfanyl)benzenesulfonylmethyl]-cyclohexanecarboxamide trifluoroacetate salt LC/MS: M+1: 515.1;
89. trans-N-cyanomethyl-2-[3-fluoro-4-(2-ethylsulfonylaminoethylsulfanyl)-benzenesulfonylmethyl]-cyclohexanecarboxamide;
90. trans-N-cyanomethyl-2-[4-(2-chlorophenylmethylaminocarbonylmethylsulfanyl)-benzenesulfonylmethyl]-cyclohexanecarboxamide;
91. trans-N-cyanomethyl-2-[4-(4-methoxybenzylaminocarbonylmethylsulfanyl)-benzenesulfonylmethyl]-cyclohexanecarboxamide;
92. trans-N-cyanomethyl-2-[4-(furan-2-ylmethylaminocarbonylmethylsulfanyl)-benzenesulfonylmethyl]-cyclohexanecarboxamide;
93. trans-N-cyanomethyl-2-[4-(4-chlorophenylmethylaminocarbonylmethylsulfanyl)-benzenesulfonylmethyl]-cyclohexanecarboxamide;
94. trans-N-cyanomethyl-2-[3-fluoro-4-(2-dimethylsulfonylaminoethylsulfanyl)-benzenesulfonylmethyl]-cyclohexanecarboxamide;
95. trans-N-cyanomethyl-2-[4-(2-methylsulfonyloxyethylsulfanyl)-benzenesulfonylmethyl]-cyclohexanecarboxamide $^1$HNMR (dmso-d$_6$): δ 8.55 (1H, m), 7.69 (2H, m), 7.57 (2H, m), 4.05 (2H, d, J: 5.2 Hz), 3.46 (2H, t, J:6.4 Hz), 3.41 (3H, s), 3.20 (3H, m), 2.93 (1H, d, J: 14 Hz), 2.05 (3H, m), 1.67 (3H, m), 1.30 (1H, m), 1.14 (3H, m). LC/MS: M-1: 473.1;
96. trans-N-cyanomethyl-2-[4-(3-dimethylaminobenzylaminocarbonylmethyl-sulfanyl)benzenesulfonylmethyl]cyclohexanecarboxamide;
97. trans-N-cyanomethyl-2-[4-(4-pyridin-4-ylpiperazin-1-ylcarbonylmethylsulfanyl)-benzenesulfonylmethyl]cyclohexanecarboxamide;
98. trans-N-cyanomethyl-2-(4-methoxycarbonylmethyloxybenzenesulfonylmethyl)-cyclohexanecarboxamide;

99. trans-N-cyanomethyl-2-[4-(1-ethyloxycarbonylethylsulfanyl)-benzenesulfonylmethyl]-cyclohexanecarboxamide;
100. trans-N-cyanomethyl-2-[4-(1-tert-butylpiperazin-4-ylcarbonylmethylsulfanyl)-benzenesulfonylmethyl]-cyclohexanecarboxamide;
101. trans-N-cyanomethyl-2-[4-(1-pyridin-2-ylpiperazin-4-ylcarbonylmethylsulfanyl)-benzenesulfonylmethyl]-cyclohexanecarboxamide;
102. trans-N-cyanomethyl-2-[4-(1-tert-butylpiperazin-4-ylcarbonylmethyloxy)-benzenesulfonylmethyl]-cyclohexanecarboxamide ¹HNMR (dmso-d₆): δ 8.56 (1H, t, J:5.6 Hz), 7.71 (2H, m), 7.12 (2H, m), 5.05 (2H, m), 4.04 (2H, d, J: 4.8 Hz), 3.42 (8H, m), 3.12 (1H, m), 2.94 (1H, m), 2.15 (1H, m), 2.00 (2H, m), 1.67 (3H, m), 1.33 (10H, m), 1.14 (3H, m). LC/MS, M+1: 519.2;
103. trans-N-cyanomethyl-2-[4-(1-pyrimidin-2-ylpiperazin-4ylcarbonylmethylsulfanyl)-benzenesulfonylmethyl]-cyclohexanecarboxamide;
104. trans-N-cyanomethyl-2-[4-(2-thien-2-ylethylaminocarbonylmethylsulfonyl)-benzenesulfonylmethyl]-cyclohexanecarboxamide;
105. trans-N-cyanomethyl-2-{4-[1-(4-bromophenyl)piperazin-4-ylcarbonylmethylsulfanyl]-benzenesulfonylmethyl}-cyclohexanecarboxamide;
106. trans-N-cyanomethyl-2-[4-(2-pyridin-4-ylethylaminocarbonylmethyloxy)-benzene-sulfonylmethyl]-cyclohexanecarboxamide;
107. 2-(4-fluorophenylsulfanylmethyl)cyclohexane carboxylic acid (1-cyanocyclopropyl amide.
108. trans-N-cyanomethyl-2-[4-(3-methyl-1,2,5-oxadiazol-4-ylmethylaminocarbonylmethyl-sulfanyl)-benzenesulfonylmethyl]-cyclohexanecarboxamide;
109. trans-N-cyanomethyl-2-[4-(2-morpholin-4-ylcarbonylaminoethylsulfanyl)-benzenesulfonylmethyl]-cyclohexanecarboxamide;
110. trans-N-cyanomethyl-2-[4-(pyridin-3-yloxyethylsulfanyl)-benzenesulfonylmethyl]-cyclohexanecarboxamide trifluoroacetate salt. ¹HNMR (dmso-d₆): δ 8.56 (1H, t, J:6.0 Hz), 8.38 (1H, m), 8.26 (1H, d, J:4.8 Hz), 7.70 (2H, dd, J:8.8 and 1.6 Hz), 7.62 (1H, m), 7.56 (2H, dd, J:8.8 and 1.6 Hz), 7.50 (1H, m), 4.35 (2H, m), 4.04 (2H, d, J:5.6 Hz), 3.55 (2H, m), 3.15 (1H, m), 2.93 (1H, d, J:14.4 Hz), 2.15 (1H, m), 2.00 (2H, m), 1.65 (3H, m), 1.30 (1H, m), 1.13 (3H, m). MS [ESI, (M+H)⁺] m/z=474.1 amu;
111. trans-N-cyanomethyl-2-[4-(2-morpholin-4-ylcarbonylaminoethyloxy)-benzenesulfonyl-methyl]-cyclohexanecarboxamide;
112. trans-N-cyanomethyl-2-[4-(1-benzylpiperidin-4-ylaminocarbonylmethylsulfanyl)-benzenesulfonylmethyl]-cyclohexanecarboxamide;
113. trans-N-cyanomethyl-2-[4-(furan-2-ylmethylaminocarbonylmethyl)-benzenesulfonyl-methyl]-cyclohexanecarboxamide;
114. trans-N-cyanomethyl-2-[4-(2-furan-2-ylmethylaminocarbonylethyl)-benzenesulfonyl-methyl]-cyclohexanecarboxamide;
115. trans-N-cyanomethyl-2-[4-(2-furan-2-ylmethylaminocarbonylethyl)-phenylsulfanyl-methyl]-cyclohexanecarboxamide;
116. trans-N-cyanomethyl-2-[4-(benzylsulfanylmethyl)-benzenesulfonylmethyl]-cyclohexanecarboxamide;
117. trans-N-cyanomethyl-2-[4-(2-bromoethylsulfanyl)-benzenesulfonylmethyl]-cyclohexanecarboxamide LC/MS: M-1: 459.3;
118. trans-6-(4-fluorophenylsulfanylmethyl)spiro[2.4]heptane-5-carboxylic acid cyanomethylamide MS [APCI, (M–H)⁻] m/z=317.0;
119. trans-6-(4-fluorobenzenesulfonylmethyl)spiro[2.4]heptane-5-carboxylic acid cyanomethylamide MS [APCI, (M–H)⁻] m/z=349.0;
120. trans-2-(4-fluorophenylsulfanylmethyl)-4-methylcyclopentanecarboxylic acid cyanomethylamide MS [APCI, (M–H)⁻] m/z=305.1;
121. trans-3-(4-methylsulfanylbenzenesulfonylmethyl)bicyclo-[4.1.0]heptane-2-carboxylic acid cyanomethylamide MS [ESI, (M+H)⁻] m/z=406.4 amu 379.1;
122. trans-N-cyanomethyl-2-(4-fluorophenylsulfanylmethyl)-5-methylcyclohexane-carboxamide MS [ESI, (M–H)⁻] m/z=319.2⁻;
123. cis-N-cyanomethyl-2-(4-methylsulfanylbenzenesulfonylmethyl)-cyclohexane-carboxamide;
124. trans-N-cyanomethyl-2-[1-(4-methylsulfanylbenzenesulfonyl)ethyl]-cyclohexanecarboxamide;
125. trans-N-cyanomethyl-2-{4-[3-(2-morpholin-4-ylethylaminocarbonyl)propyl]-phenylsulfanylmethyl}cyclohexanecarboxamide;
126. (R,R)-N-cyanomethyl-2-(4-methylsulfanylbenzenesulfonylmethyl)cyclohexane-carboxamide;
127. trans-N-cyanomethyl-2-[4-(2-morpholin-4-ylethylaminocarbonylmethylsulfanyl)-benzenesulfonylmethyl]cyclohexanecarboxamide;
128. trans-N-cyanomethyl-2-[4-(2-pyridin-2-ylethylsulfanyl)benzenesulfonylmethyl]-cyclohexanecarboxamide;
129. (1R/S,2R/S,5R/S)trans-N-cyanomethyl-2-(4-methylsulfanylbenzenesulfonylmethyl)-5-methylcyclohexane-carboxamide MS [ESI, (M–H)⁻] m/z=379.2;
130. trans-N-cyanomethyl-2-(4-methylsulfanylbenzenesulfonylmethyl)-cyclohexanecarboxamide MS [ESI, (M–1)⁻] m/z=365.0;
131. trans-N-cyanomethyl-2-[3-fluoro-4-(2-pyridin-2-ylethylsulfanyl)benzenesulfonyl-methyl]cyclohexanecarboxamide;
132. trans-N-cyanomethyl-2-[4-(piperidin-3-ylaminocarbonylmethylsulfanyl)benzenesulfonylmethyl]cyclohexanecarboxamide;
133. trans-2-[4-(pyridin-2-ylethylsulfanyl)benzenesulfonylmethyl]cyclohexanecarboxylic acid (1-cyanocyclopropyl)amide;
134. trans-N-cyanomethyl-2-[4-(4-isopropylpiperazin-1-ylcarbonylmethylsulfanyl)benzene-sulfonylmethyl]cyclohexanecarboxamide;
135. trans-N-cyanomethyl-2-[4-(furan-2-ylmethylsulfanyl)benzenesulfonylmethyl]-cyclohexanecarboxamide;
136. trans-N-cyanomethyl-2-(3-hydroxypropylsulfanylbenzenesulfonylmethyl)-cyclohexanecarboxamide;
137. trans-N-cyanomethyl-2-[4-(4-thiolphenylsulfanyl)phenylsulfanylmethyl)-cyclohexanecarboxamide;
138. trans-2-{[(4-chlorophenyl)sulfanyl]methyl}-N-(cyanomethyl)cyclopentanecarboxamide MS [ESI, (M–H)⁻] m/z=307.2;
139. trans-N-(cyanomethyl)-2-{[(4-fluorophenyl)sulfanyl]methyl}cyclopentanecarboxamide MS [ESI, (M–H)⁻] m/z=291.2;
140. trans-2-{[(3-bromophenyl)sulfanyl]methyl}-N-(cyanomethyl)cyclohexanecarboxamide MS [ESI, (M–H)⁻] m/z=366.6;
141. trans-N-(cyanomethyl)-2-{[(3-fluorophenyl)sulfanyl]methyl}cyclohexanecarboxamide MS [ESI, (M–H)⁻] m/z=305.1;

142. trans-2-{[(3-aminophenyl)sulfanyl]methyl}-N-(cyanomethyl)cyclohexanecarboxamide MS [ESI, (M−H)⁻] m/z=302.1;

143. trans-N-(cyanomethyl)-2-({[3-(trifluoromethyl)phenyl]sulfanyl}methyl)-cyclohexanecarboxamide MS [ESI, (M−H)⁻] m/z=355.1;

144. 3-{[(trans-2-{[(cyanomethyl)amino]carbonyl}cyclohexyl)methyl]sulfanyl}benzoic acid MS [APCI, (M−H)⁻] m/z=331.0;

145. 4-{[(trans-2-{[(cyanomethyl)amino]carbonyl}cyclohexyl)methyl]sulfanyl}benzoic acid MS [APCI, (M−H)⁻] m/z=331.0

146. trans-N-(cyanomethyl)-2-{[(3-hydroxyphenyl)sulfanyl]methyl}cyclohexanecarboxamide MS [ESI, (M−H)⁻] m/z=303.0;

147. trans-N-(cyanomethyl)-2-({[3-(formylamino)phenyl]sulfanyl}methyl)-cyclohexanecarboxamide MS [ESI, (M−H)⁻] m/z=330.2;

148. trans-2-({[3-(acetylamino)phenyl]sulfanyl}methyl)-N-(cyanomethyl)cyclohexane-carboxamide MS [ESI, (M−H)⁻] m/z=344.0;

149. trans-2-[({3-[bis(methylsulfonyl)amino]phenyl}sulfanyl)methyl]-N-(cyanomethyl)-cyclohexanecarboxamide MS [ESI, (M−H)⁻] m/z=458.1;

150. trans-N-(cyanomethyl)-2-{[(4 iodophenyl)sulfanyl]methyl}cyclopentanecarboxamide MS [ESI, (M−H)⁻] m/z=398.9;

151. trans-N-(cyanomethyl)-2-{[4-iodobenzenesulfonyl]methyl}cyclopentanecarboxamide MS [ESI, (M−H)⁻] m/z=431.1;

152. (1S/R,2R/S,3R/S,4R/S)-N-(cyanomethyl)-3-{[(4-fluorophenyl)sulfanyl]methyl}-bicyclo[2.2.1]hept-5-ene-2-carboxamide MS [APCI, (M+H)⁺] m/z=316.9;

153. (1R/S,2R/S,3R/S,4S/R)-N-(cyanomethyl)-3-{4-fluorobenzenesulfonylmethyl}bicyclo-[2.2.1]hept-5-ene-2-carboxamide MS [ESI, (M−H)⁻] m/z=347.1;

154. (1R/S,2R/S,3R/S,4S/R)-N-(cyanomethyl)-3-({[4-methylsulfanylbenzenesulfonyl}-methyl)-bicyclo[2.2.1]hept-5-ene-2-carboxamide MS [APCI, (M−H)⁻] m/z=375.0;

155. (1S/R,2R/S,3R/S,4R/S)-N-(cyanomethyl)-3-{4-fluorobenzenesulfonylmethyl}-bicyclo[2.2.1]heptane-2-carboxamide MS [APCI, (M−H)⁻] m/z=349.0;

156. (1S/R,2R/S,3R/S,4R/S)-N-(cyanomethyl)-3-(4-methylsulfanylbenzenesulfonyl-methyl)bicyclo[2.2.1]heptane-2-carboxamide MS [APCI, (M−H)⁻] m/z=377.1;

157. trans-N-(cyanomethyl)-6-({[4-(methylsulfanyl)benzene]sulfonyl}methyl)-spiro[2.4]heptane-5-carboxamide MS [APCI, (M−H)⁻] m/z=377.1;

158. trans-N-(cyanomethyl)-2-{4-fluorobenzenesulfonylmethyl}cyclopentanecarboxamide MS [APCI, (M−H)⁻] m/z=323.0;

159. trans-N-(cyanomethyl)-2-({4-methylsulfanylbenzenesulfonyl}methyl)-cyclopentanecarboxamide MS [APCI, (M−H)⁻] m/z=351.0;

160. (1R/S,2R/S,3R/S,4S/R)-N-(cyanomethyl)-3-{[(4-hydroxyphenyl)sulfanyl]methyl}-bicyclo[2.2.1]hept-5-ene-2-carboxamide MS [ESI, (M−H)⁻] m/z=313.3;

161. (1R/S,2R/S,3R/S,4S/R)-N-(cyanomethyl)-3-f{4-hydroxybenzenesulfonylmethyl}-bicyclo[2.2.1]hept-5-ene-2-carboxamide MS [ESI, (M−H)⁻] m/z=345.2;

162. trans-N-(cyanomethyl)-6-{[(4-fluorophenyl)sulfanyl]methyl}cyclohex-3-ene-1-carboxamide 303.1;

163. N-(cyanomethyl)-7-{4-fluorobenzenesulfonylmethyl}-3-oxatricyclo[3.2.1.0²,⁴]octane-6-carboxamide MS [APCI, (M−H)⁻] m/z=361.0;

164. trans-N-(cyanomethyl)-2-{[(4-iodophenyl)sulfanyl]methyl}cyclohexanecarboxamide MS [APCI, (M−H)⁻] m/z=412.9;

165. trans-N-(cyanomethyl)-2-{4-iodobenzenesulfonylmethyl}cyclohexanecarboxamide MS [APCI, (M−H)⁻] m/z=444.9;

166. trans-N-(cyanomethyl)-2-[({4-[(2,2,2-trifluoroethyl)sulfanyl]benzene}sulfonyl)methyl]-cyclohexanecarboxamide MS [ESI, (M−H)⁻] m/z=433.1;

167. trans-N-(cyanomethyl)-2-[({4-[(difluoromethyl)sulfanyl]phenyl}sulfanyl)methyl]-cyclohexanecarboxamide MS [ESI, (M−H)⁻] m/z=369.3;

168. trans-N-(cyanomethyl)-2-[({4-[(difluoromethyl)sulfanyl]benzene}sulfonyl)methyl]-cyclohexanecarboxamide MS [ESI, (M−H)⁻] m/z=401.3;

169. N-(cyanomethyl)-2-{4-fluorobenzenesulfonylmethyl}-4-methylcyclopentane-carboxamide MS [ESI, (M−H)⁻] m/z=337.2;

170. N-(cyanomethyl)-4-methyl-2-({4-methylsulfanylbenzenesulfonyl}methyl)-cyclopentane-carboxamide MS [ESI, (M−H)⁻] m/z=365.1;

171. N-(cyanomethyl)-2-{4-fluorobenzenesulfonylmethyl}-5-methylcyclohexane-carboxamide MS [ESI, (M−H)⁻] m/z=351.1;

172. trans-N-(cyanomethyl)-2-({4-difluoromethoxybenzenesulfonyl}methyl)cyclohexane-carboxamide MS [ESI, (M−H)⁻] m/z=385.1;

173. (1R/S,2R/S,3R/S,6S/R)-N-(cyanomethyl)-3-{[(4-fluorophenyl)sulfanyl]methyl}-bicyclo[4.1.0]-heptane-2-carboxamide MS [ESI, (M−H)⁻] m/z=317.0;

174. (1R/S,2R/S,3R/S,6S/R)-N-(cyanomethyl)-3-{4-fluorobenzenesulfonylmethyl}-bicyclo[4.1.0]-heptane-2-carboxamide MS [ESI, (M+H)⁺] m/z=351.0 amu;

175. trans-N-(cyanomethyl)-2-{[4-(methylsulfanyl)phenoxy]methyl}cyclohexanecarboxamide MS [ESI, (M+H)⁺] m/z=317.0;

176. trans-N-(cyanomethyl)-2-(1-{4-methylsulfanylbenzenesulfonyl}ethyl)cyclohexane-carboxamide MS [ESI, (M+H)⁺] m/z=381.2;

177. trans-2-(4-methoxybenzylsulfonylmethyl)-cyclohexanecarboxylic acid cyanomethyl-amide;

178. trans-N-cyanomethyl-2-(4-carboxymethylsulfanylbenzenesulfonylmethyl)cyclohexane-carboxamide;

179. trans-N-(cyanomethyl)-2-({[4-(methylsulfanyl)phenyl]sulfanyl}-methyl)cyclopentane-carboxamide;

180. (1S/R,3R/S,4R/S,6R/S)-N-(cyanomethyl)-4-({[4-(methylsulfanyl)phenyl]sulfanyl}-methyl)bicyclo[4.1.0]heptane-3-carboxamide;

181. trans-N-(cyanomethyl)-6-{[(4-fluorophenylsulfanyl]methyl}spiro[2.4]heptane-5-carboxamide;

182. trans-N-(cyanomethyl)-6-{[(4-fluorobenzene)sulfonyl]methyl}spiro[2.4]heptane-5-carboxamide;

183. (1R/S,6R/S)-N-(cyanomethyl)-6-({[4-(methylsulfanyl)phenylsulfanyl]-methyl)cyclohex-3-ene-1-carboxamide;

184. (1R,2R)-N-(cyanomethyl)-2-({[4-(methylsulfanyl)benzene]sulfonyl}methyl)-cyclohexanecarboxamide;

185. (1R/S,2R/S,3R/S,6S/R)-N-(cyanomethyl)-3-({[4-(methylsulfanyl)benzene]sulfonyl}-methyl)bicyclo[4.1.0]heptane-2-carboxamide;

186. trans-N-cyanomethyl-2-(4-hydroxymethylbenzenesulfonylmethyl)-cyclohexanecarboxamide;

187. trans-N-cyanomethyl-2-(4-benzylsulfonylmethylbenzenesulfonylmethyl)-cyclohexanecarboxamide;

188. trans-N-cyanomethyl-2-[4-(2-morpholin-4-ylethyloxy)phenylsulfanylmethyl]-cyclohexanecarboxamide;

¹HNMR (dmso-d₆): δ 8.62 (1H, m), 7.27 (2H, d, J:5.7 Hz, 6.94 (2H, d, J:5.7 Hz), 4.30 (2H, m), 4.10 (2H, m), 3.95 (4H, m), 3.69 (2H, m), 3.50 (4H, m), 2.90 (1H, m), 2.45 (1H, m), 2.07 (3H, m), 1.70 (3H, m), 1.30 (1H, m), 1.14 (3H, m). LC/MS, M+1: 419.2;

189. trans-N-(cyanomethyl)-6-{[(4-methylsulfanylphenyl)sulfanyl]methyl}cyclohex-3-ene-1-carboxamide;
190. (1S/R,3S/R,4S/R,6R/S)-N-(cyanomethyl)-4-({[4-(methylsulfanyl)phenyl]sulfanyl}-methyl)bicyclo[4.1.0]heptane-3-carboxamide;
191. (1R/S,2R/S,3R/S,4S/R)-N-(cyanomethyl)-3-{4-fluorophenylsulfanylmethyl}bicyclo-[2.2.1]hept-5-ene-2-carboxamide;
192. (1S/R,2R/S,3R/S,4R/S)-N-(cyanomethyl)-3-{4-fluorophenylsulfanylmethyl}bicyclo-[2.2.1]heptane-2-carboxamide;
193. (1R/S,2S/R,3S/R,6S/R)-N-(cyanomethyl)-3-{[(4-fluorophenyl)sulfanyl]methyl}-bicyclo[4.1.0]-heptane-2-carboxamide;
194. (1R/S,2S/R,3S/R,6S/R)-N-(cyanomethyl)-3-{[(4-methylsulfanylbenzene)sulfonyl]-methyl}-bicyclo[4.1.0]-heptane-2-carboxamide; and
195. (1R/S,2S/R,3S/R,6S/R)-N-(cyanomethyl)-3-{[(4-fluorobenzene)sulfonyl]-methyl}-bicyclo[4.1.0]-heptane-2-carboxamide; or a pharmaceutically acceptable salt thereof.

As used above the term "trans" includes a mixture of both the diasteromers. However, the present invention also include within its scope individual diasteromers of above compounds i.e., the stereochemistry around the cyclohexyl ring is (1R, 2R), (1S, 2S), (1S, 2R) or (1R, 2S).

General Synthetic Scheme

Compounds of this invention can be made by the methods discussed below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., in a subclass from about 0° C. to about 125° C. and most preferably at about room (or ambient) temperature, e.g., about 20° C.

Scheme A

A compound of Formula I where $R^4$ and $R^5$ are hydrogen can be prepared as illustrated and described below.

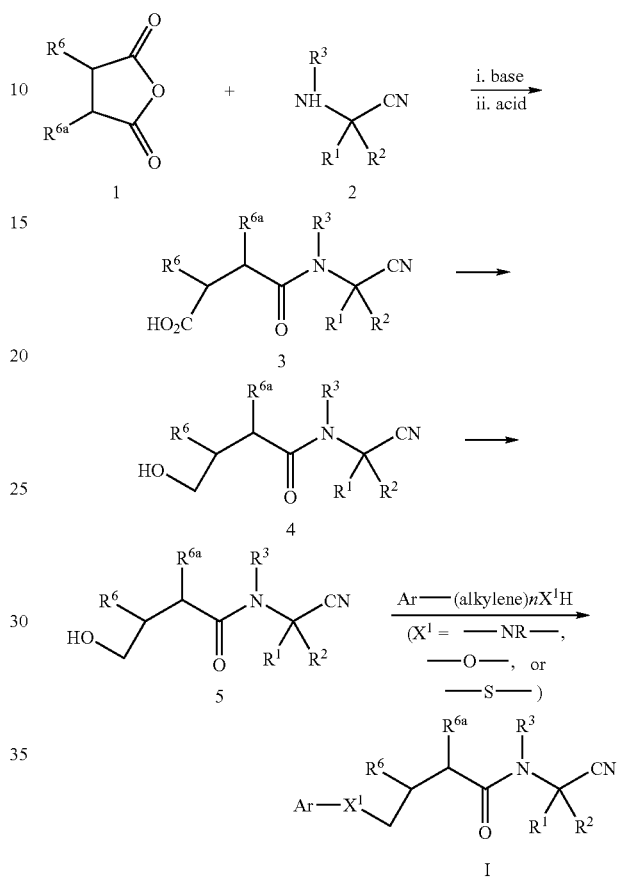

Reaction of an anhydride of formula 1 with an aminoacetonitrile of formula 2 (where $R^1$-$R^3$, $R^6$ and $R^{6a}$ are as defined in the Summary of the Invention) in the presence of an organic base such as diisopropylethylamine, triethylamine, pyridine, and the like, followed by acidification of the reaction mixture with an acid such as hydrochloric acid provides N-cyanomethylamino-carbonyl compound of formula 3. The reaction is typically carried out between 0° C. and ambient temperature and in an aprotic organic solvent such as tetrahydrofuran, and the like. Compounds of formula 1 and 2 are commercially available or they can be prepared by methods well known in the art. For example, anhydrides of formula 1 such as cis and trans1,2-cyclohexanedicarboxylic acid anhydride, phthalic anhydride, 2,3- or 2,4-pyridinedicarboxylic anhydride, 2,3-pyrazinedicarboxylic anhydride, 3,4,5,6-tetrahydrophthalic anhydride, 3-, 4-methylphthalic anhydride, 3,6-dimethylphthalic anhydride, exo-3,6-epoxy-1,2,3,6-tetrahydrophthalic anhydride, and (2,6-dimethyl)-3,4,5,6-tetrahydrophthalic anhydride are commercially available. Others compound of formula 1 can be prepared from commercially available diacids such as 2,3-furandicarboxylic acid, 4,5-imidazoledicarboxylic acid, 4,5-(1,2,3-triazole)dicarboxylic acid, 1,2-cyclopentanedicarboxylic acid, 2,3-pyridinedicarboxylic acid, 2,3-pyrazinedicarboxy acid, 2,3-thiophenedicarboxylic acid, and 3,4-pyrroledicarboxylic acid by methods well known in the art.

A compound of formula 2 such as aminoacetonitrile is commercially available. Other compounds of formula 2 can be prepared by methods disclosed in PCT Applications Publication Nos. WO 01/09110, WO 01/19816, WO 00/49008, and WO 00/49007, the disclosures of which are incorporated herein by reference in their entirety.

Compound 3 is converted to hydroxymethyl derivative of formula 4 by reacting it with isobutyl chloroformate and then reducing the resulting anhydride with a suitable reducing agent such as aqueous sodium borohydride. The reaction is carried out in water miscible ethereal solvent such as methoxyethyl ether, tetrahydrofuran, and the like.

Compound 4 is then converted to a compound of formula 5 where LG is a suitable leaving group such as halo, preferably bromo, tosylate, mesylate, triflate, and the like under reaction conditions well known in the art. For example, a compound of formula 5 when LG is bromo can be prepared by reacting 4 with a suitable brominating agent such as N-bromosuccinimide or carbon tetrabromide in the presence of triphenylphosphine. Compound 5 where LG is mesylate, tosylate, or triflate can be prepared by reacting 4 with mesyl chloride, tosyl chloride, or triflic anhydride respectively.

Compound 5 is converted to a compound of Formula I where $X^1$ is —NR—, —O— or —S— by reacting it with a compound of formula Ar-(alkylene)$_n$$X^1$H where $X^1$ is —NR—, —O—, or —S— and n is 0 or 1. The reaction is carried out in the presence of a base such as cesium carbonate, and the like and in a suitable solvent such as acetonitrile, acetone, dimethylformamide, and the like.

Compounds of formula 5 such as 2-mercaptoimidazole, 5-mercapto-1,2,3-triazole, 2-mercapto-1,3,4-triazole, 4-mercaptopyridine, 2-mercaptopyrimidine, 2-methyl-3-mercaptofuran, 4-aminothiophenol, 3-, 4-fluorobenzenethiol, 4-methyl-2-mercaptothiazole, 2,3,4-trichlorobenzenethiol, 2-mercaptobenzoxazole, phenol, aniline, 2,3,4-chloroaniline, 2-amino-4-chlorophenol, 2,3,4-fluoroaniline, 2,3,4-iodoaniline, 2,3,4-nitroaniline, 2-amino-3-nitrophenol, 2-hydroxy-4-methyl-3-nitropyridine, and 2-methoxy-5-nitropyridine are commercially available. Other available starting material may be searched using Available Chemicals Directory.

Other compounds of formula 5 can be prepared by methods well known in the art. Some such methods are described below:
1. A compound of formula 5 where Ar is —Ar$^1$—X$^4$—Ar$^2$ where $X^4$ is a bond can be prepared under Suzuki reaction conditions as follows:

The reaction is carried out in a suitable solvent (e.g., N,N-dimethylformamide (DMF), 2-propanol, or the like) in the presence of sodium bicarbonate and palladium(II)chloride under nitrogen at 800 to 85° C. and requires 1 to 5 h to complete the reaction.
2. A compound of formula 5 where Ar is —Ar$^1$—X$^4$—Ar$^2$ where $X^4$ is —NR$^{15}$X$^8$, —NR$^{15}$C(O)X$^8$—, —C(O)NR$^{15}$X$^8$—, —NR$^{15}$C(O)OX$^8$—, —OC(O)NR$^{15}$X$^8$—, —NR$^{15}$C(O)NR$^{15}$X$^8$—, —NR$^{15}$C(NR$^{15}$)NR$^{15}$X$^8$—, —C(O)X$^8$—, —C(O)OX$^8$—, —OC(O)X$^8$—, and —NR$^{15}$S(O)$_2$X$^8$—, where $X^8$ independently are a bond or —(C$_{1-6}$)alkylene and R$^{15}$ is hydrogen or C$_{1-6}$)alkyl can be by methods disclosed in U.S. Pat. No. 6,136,844 the disclosure of which is incorporated herein by reference in its entirety. Other methods to prepare such compounds are disclosed in PCT Application Publication No. WO 00/55126, the disclosure of which is incorporated herein by reference in its entirety. It will be appreciated by a person skilled in the art that the above procedures can also be used to prepared compounds of Formula I where Ar is —Ar$^1$—X$^4$—Ar$^2$—X$^5$—Ar$^3$.

Scheme B

Alternatively, a compound of Formula I where R$^4$ and R$^5$ are hydrogen can be prepared as illustrated and described below.

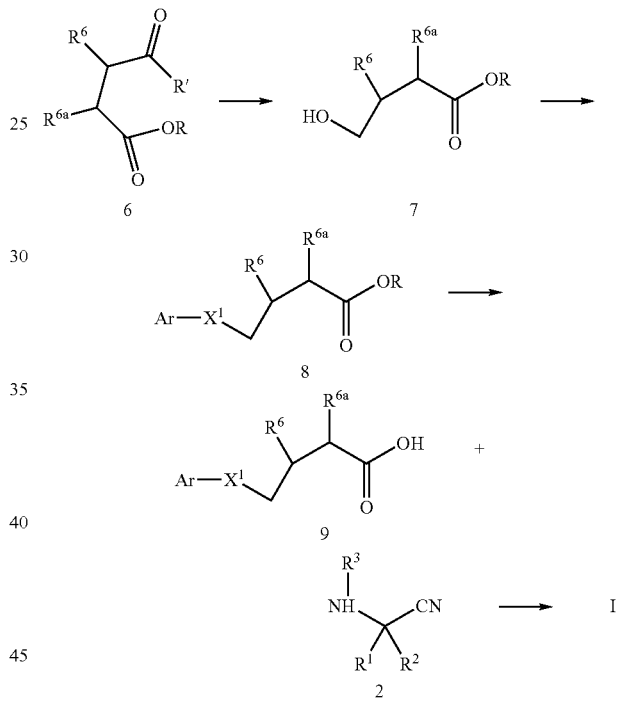

Reduction of the acid (R' is hydroxy) or formyl (R' is hydrogen) group in a compound of formula 6 where R is alkyl, with a suitable reducing agent such as sodium borohydride provides a compound of formula 7 which is then converted to a compound of formula 8 as described in Scheme A above. Hydrolysis of the ester group in 8 under standard hydrolysis conditions followed by reaction of the resulting acid 9 with aminoacetonitrile of formula 2 under the reaction conditions described in Scheme A above then provides a compound of Formula I. Compounds of formula 6 are either commercially available or they can be prepared by methods well known in the art. For example, cyclopentane-1,2-dicarboxylic acid monomethyl ester can be prepared from commercially available cyclopentane-1,2-dicarboxylic acid by first converting it to a diester and then selectively hydrolyzing one of the ester groups. A compound of formula 6 where R' is hydrogen and R$^6$ and R$^{6a}$ together with the carbon atoms to which they are attached form cycloalkenylene can be prepared under Diels-Alder reaction conditions by reacting ethyl 13-formylacrylate (see M. Schmitt, J. J. Bourguignon, C. G. Wermuth, *Tetrahedron Lett.*, 31 (15), p. 2145-2148 (1990)) and acrolein in the presence of hydroquinone as described in working examples below.

Detailed descriptions of syntheses of compounds of Formula I by the above procedures are provided in Examples 1-37 below.

Additional Processes for Preparing Compounds of Formula I:

Compounds of Formula I can also be prepared by modification of a group present on a corresponding compound of Formula I. For example, a compound of Formula I where $Ar_1$ is substitued with —OH, —O-halo substituted alkyl, —OCONR$^{16}$R$^{16}$, or —OC(O)R$^{16}$ where R$^{16}$ is alkyl or halo substituted alkyl may be prepared by de-alkylation of an alkoxy substituent e.g., methoxy, on the corresponding compound of Formula I, followed by treatment with an appropriate alkylating or acylating agents. The transformation can be carried out by methods well known in the field of organic chemistry.

Compounds of Formula I where Ar$^1$ is substituted with alkyl, cyano, halo, —COOR$^{16}$, —CONR$^{16}$R$^{16}$ can be prepared from the corresponding compounds of Formula I where Ar$^1$ is substitued with hydroxy by following literature procedures described in Ortar. G., *Tett. Lett.*, 27, 5541 (1986); Stille, J. K., *J. Org. Chem.*, 52, 422, (1987); and Capri, W., *J. Org. Chem.*, 55, 350, (1990).

Compounds of Formula I where X$^1$ is —S— can be converted to a corresponding compound of Formula I where X$^1$ is —S(O) or —S(O)$_2$ by oxidising it with a suitable oxidizing agent such as sodium periodate or Oxone respectively.

The conversion of compounds of Compounds of Formula I where X$^1$ is —S— can be converted to a corresponding compound of Formula I where X$^1$ is —S(O) or —S(O)$_2$ are described in Examples 4 and 5 respectively.

It will be recognized by one skilled in the art that these transformation are not limited to the Ar$^1$ group but may be carried out at other positions in the compound of Formula I.

A compound of Formula I can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula I can be prepared by reacting the free acid form of the compound with a pharmaceutically acceptable inorganic or organic base. Inorganic and organic acids and bases suitable for the preparation of the pharmaceutically acceptable salts of compounds of Formula I are set forth in the definitions section of this application. Alternatively, the salt forms of the compounds of Formula I can be prepared using salts of the starting materials or intermediates.

The free acid or free base forms of the compounds of Formula I can be prepared from the corresponding base addition salt or acid addition salt form. For example, a compound of Formula I in an acid addition salt form can be converted to the corresponding free base by treating with a suitable base (e.g., ammonium hydroxide solution, sodium hydroxide, etc.). A compound of Formula I in a base addition salt form can be converted to the corresponding free acid by treating with a suitable acid (e.g., hydrochloric acid, etc).

The N-oxides of compounds of Formula I can be prepared by methods known to those of ordinary skill in the art. For example, N-oxides can be prepared by treating an unoxidized form of the compound of Formula I with an oxidizing agent (e.g., trifluoroperacetic acid, permaleic acid, perbenzoic acid, peracetic acid, meta-chloroperoxybenzoic acid, etc.) in a suitable inert organic solvent (e.g., a halogenated hydrocarbon such as methylene chloride) at approximately 0 C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g., sulfur, sulfur dioxide, triphenyl phosphine, lithium borohydride, sodium borohydride, phosphorus trichloride, tribromide, etc.) in an suitable inert organic solvent (e.g., acetonitrile, ethanol, aqueous dioxane, etc.) at 0 to 80 C.

Prodrugs of the compounds of Formula I can be prepared by methods known to those of ordinary skill in the art (e.g., for further details see Saulnier et al. (1994), *Bioorganic and Medicinal Chemistry Letters.* 4:1985). For example, appropriate prodrugs can be prepared by reacting a non-derivatized compound of Formula I with a suitable carbamylating agent (e.g., 1,1-acyloxyalkylcarbonochloridate, para-nitrophenyl carbonate, etc.).

Protected derivatives of the compounds of Formula I can be made by means known to those of ordinary skill in the art. A detailed description of the techniques applicable to the creation of protective groups and their removal can be found in T. W. Greene, *Protective Groups in Organic Synthesis*, John Wiley & Sons, Inc. 1981.

Compounds of Formula I can be prepared as their individual stereoisomers by reacting a racemic mixture of the compound with an optically active resolving agent to form a pair of diastereoisomeric comounds, separating the diastereomers and recovering the optically pure enantiomer. While resolution of enantiomers can be carried out using covalent diasteromeric derivatives of compounds of Formula I, dissociable complexes are preferred (e.g., crystalline diastereoisomeric salts). Diastereomers have distinct physical properties (e.g., melting points, boiling points, solubilities, reactivity, etc.) and can be readily separated by taking advantage of these disimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, Honh Wiley & Sons, Inc. (1981).

Pharmacology and Utility

The compounds of this invention are cysteine protease inhibitors, in particular cathepsin K protease inhibitors, and are useful for treating diseases in which cathepsin K activity contributes to the pathology and/or symptomatology bone resorption disorders, e.g., osteoporosis.

The compounds of Formula I also inhibit cathepsins S, B, and L protease and hence are useful in treating such as cancer, rheumatoid arthritis, osteoarthritis, *pneumocystis carinii*, acute pancreatitis, inflammatory airway disease and bone and joint disorders, Alzheimer's disease and certain autoimmune disorders, including, but not limited to juvenile onset diabetes, multiple sclerosis, pemphigus vulgaris, Graves' disease, myasthenia gravis, systemic lupus erythemotasus, and Hashimoto's thyroiditis; allergic disorders, including, but not limited to asthma; and allogeneic immune responses, including, but not limited to, rejection of organ transplants or tissue grafts.

The cysteine protease inhibitory activities of the compounds of the invention can be determined by methods known to those of ordinary skill in the art. Suitable i: vitro assays for measuring protease activity and the inhibition thereof by test compounds are known. Typically, the assay measures protease induced hydrolysis of a peptide based substrate. Details of assays for measuring protease inhibitory activity are set forth in Biological Examples 1, 2, 3, and 4, infra.

Administration and Pharmaceutical Compositions

In general, compounds of Formula I will be administered in therapeutically effective amounts via any of the usual and acceptable modes known in the art, either singly or in combination with another therapeutic agent. A therapeutically effective amount may vary widely depending on the severity of the disease, the age and relative health of the subject, the potency of the compound used and other factors. For example, therapeutically effective amounts of a compound of Formula I for anticoagulant therapy may range from 10 micrograms per kilogram body weight (jig/kg) per day to about 20 milligram per kilogram body weight (mg/kg) per day, typically from about 100 μg/kg/day to about 10 mg/kg/day. Therefore, a therapeutically effective amount for an 80 kg human patient may range from about 1 mg/day to about 1.6 g/day, typically from about 1 mg/day to about 100 mg/day. In general, one of ordinary skill in the art, acting in reliance upon personal knowledge and the disclosure of this Application, will be able to ascertain a therapeutically effective amount of a compound of Formula I for treating a given disease.

The compounds of Formula I can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

The amount of a compound of Formula I in the composition may vary widely depending upon the type of formulation, size of a unit dosage, kind of excipients and other factors known to those of skill in the art of pharmaceutical sciences. In general, a composition of a compound of Formula I for treating a given disease will comprise from 0.01% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula I are described in Formulation Examples 1-3 below.

The compounds of Formula I can be administered alone or in combination with other compounds of Formula I or in combination with one or more other active ingredient(s). For example, the compounds of Formula I can be administered in combination with a therapeutically active amount of a bisphosphonic acid or acid ester derivative or any pharmaceutically acceptable salt thereof. Suitable bisphosphonic acids and acid ester derivatives include compounds corresponding to the following formula:

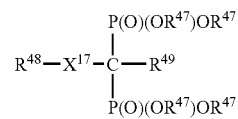

wherein $X^{17}$ is a bond or $(C_{1-7})$alkylene, each $R^{47}$ independently is hydrogen or $(C_{1-30})$alkyl, $R^{48}$ and $R^{49}$ are selected independently from a group consisting of hydrogen, halo, optionally substituted $(C_{1-30})$alkyl, $(C_{3-30})$cycloalkyl, $(C_{5-30})$heterocycloalkyl, optionally substituted $(C_{6-10})$aryl, hetero$(C_{6-10})$aryl, $NR^{40}R^{40}$, $OR^{40}$, $SR^{40}$, wherein each $R^{40}$ independently is hydrogen, $(C_{1-10})$alkyl, $(C_{3-10})$cycloalkyl, optionally substituted $(C_{6-10})$aryl, provided that both Re and $R^{49}$ are not selected from hydrogen or hydroxy when $X^{17}$ is a bond; or $R^{48}$ and $R^{49}$ taken together form $(C_{2-9})$alkylene; wherein $(C_{3-10})$cycloalkyl includes adamantyl and the like, $(C_{5-10})$heterocycloalkyl includes pyrrolidinyl and the like, $(C_{6-10})$aryl includes phenyl and naphthyl, and $(C_{6-10})$heteroaryl includes quinolyl, isoquinolyl, pyridyl, furyl, imidazolyl, imidazopyridyl and the like.

Instances wherein $R^{48}$ and/or $R^{49}$ are substituted $(C_{1-30})$ alkyl may include, but are not limited to, $(C_{1-30})$alkyl substituted by $(C_{5-10})$heterocycloalkyl, $(C_{6-10})$aryl, $(C_{6-10})$ heteroaryl, $NR^{41}R^{41}$, $OR^{41}$ and $SR^{41}$, wherein each $R^{41}$ is independently hydrogen or $(C_{1-10})$alkyl; wherein $(C_{5-10})$ heterocycloalkyl includes pyrrolidinyl and the like, $(C_{6-10})$ aryl includes phenyl and naphthyl, and $(C_{6-10})$heteroaryl includes quinolyl, isoquinolyl, pyridyl, furyl, imidazolyl, imidazopyridyl and the like. Suitable optionally substituted aryl groups include, but are not limited to, halo-substituted phenyl.

A non-limiting class of bisphosphonic acids and acid ester derivatives thereof suitable for administration in combination with compounds of Formula I include those in which $R^{48}$ is selected from the group consisting of hydrogen, hydroxy or halo, and $R^{49}$ is selected from the group consisting of optionally substituted $(C_{1-30})$alkyl, halo and $SR^{40}$, wherein $R^{40}$ is $(C_{1-10})$alkyl or phenyl.

A non-limiting subclass of bisphosphonic acids and acid ester derivatives thereof suitable for administration in combination with compounds of Formula I include those in which $R^{48}$ is selected from the group consisting of hydrogen, hydroxy and chloro and $R^{49}$ is selected from the group consisting of optionally substituted $(C_{1-30})$alkyl, chloro and chlorophenylsulfanyl.

A non-limiting example of a bisphosphonic acid suitable for administration in combination with compounds of Formula I include that in which $X^{17}$ is a bond, each $R^{47}$ is hydrogen, $R^{48}$ is hydroxy and $R^{49}$ is 3-aminopropyl, namely 4-amino-1-hydroxybutylidene-1,1-bisphosphonic acid (aka alendronic acid), or the monosodium trihydrate salt thereof, namely 4-amino-1-hydroxybutylidene-1,1-bisphosphonate monosodium trihydrate (aka alendronate monosodium trihydrate), described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which patents are incorporated by reference herein in their entirety.

Further non-limiting examples of bisphosphonic acids suitable for administration in combination with compounds of Formula I include the following:

cycloheptylaminomethylene-1,1bisphosphonic acid (aka cimadronic acid), described in U.S. Pat. No. 4,970,335, to Isomura et al., issued Nov. 13, 1990;

1,1-dichloromethylene-1,1-diphosphonic acid (aka clodronic acid) and the disodium salt thereof, namely clodronate disodium, described in Belgium Patent 672,205 (1966) and *J. Org. Chem* 32, 4111 (1967);

1-hydroxy-3-pyrrolidin-1-ylpropylidene-1,1-bisphosphonic acid (aka EB-1053);

1-hydroxyethylidene-1,1-diphosphonic acid (aka etidronic acid);

1-hydroxy-3-(N-methyl-N-pentylamino)propylidene-1,1-bisphosphonic acid (aka ibandronic acid), described in U.S. Pat. No. 4,927,814, issued May 22, 1990;

6-amino-1-hydroxyhexylidene-1,1-bisphosphonic acid (aka neridronic acid);

3-(dimethylamino)-1-hydroxypropylidene-1,1-bisphosphonic acid (aka olpadronic acid);

3-amino-1-hydroxypropylidene-1,1-bisphosphonic acid (aka pamidronic acid);

2-pyrid-2-ylethylidene-1,1-bisphosphonic acid (aka piridronic acid), described in U.S. Pat. No. 4,761,406;

1-hydroxy-2-pyrid-3-ylethylidene-1,1-bisphosphonic acid (aka risedronic acid);

4-chlorophenylsulfanylmethylenebisphosphonic acid (aka tiludronic acid), described in U.S. Pat. No. 4,876,248, to Breliere et al., Oct. 24, 1989; and 1-hydroxy-2-(1H-imidazol-1-yl)ethylidene-1,1-bisphosphonic acid (aka zoledronic acid); all of which patents and other documents referred to above are incorporated by reference herein in their entirety.

A non-limiting subclass of bisphosphonic acids suitable for administration in combination with compounds of Formula I include those selected from the group consisting of alendronic acid, cimadronic acid, clodronic acid, tiludronic acid, etidronic acid, ibandronic acid, risedronic acid, piridronic acid, pamidronic acid, zolendronic acid, pharmaceutically acceptable salts thereof, and mixtures thereof. A further example of a bisphosphonic acid suitable for administration in combination with compounds of Formula I is alendronic acid or a pharmaceutically acceptable salt thereof, and mixtures thereof. A further non-limiting example is alendronate monosodium trihydrate.

Compounds of Formula I can be administered in combination with a therapeutically active amount of an estrogen receptor modulator. Non-limiting examples of estrogen receptor modulators suitable for administration in combination with the compounds of Formula I include naturally occurring estrogens such as estradiol, estrone and estriol, or synthetic estrogen receptor modulators such as [6-hydroxy-2-(4-hydroxyphenyl)benzo[b]thien-3-yl]-[4-(2-piperidin-1-yl-ethoxy)phenyl]-methanone (aka raloxifene) and {2-[4-(1,2-diphenylbut-1-enyl) phenoxy]ethyl]dimethylamine (aka tamoxifen). A non-limiting subclass of estrogen receptor modulators suitable for administration in combination with the compounds of Formula I include estrogen receptor partial agonists (i.e., estrogen receptor modulators with mixed agonist/antagonist properties), sometimes referred to as estrogen receptor modulators. Estrogen receptor partial agonists can exert tissue-selective estrogen agonist effects. Tamoxifen, for example, selectively exerts an estrogen agonist effect on the bone, in humans. Additional suitable estrogen receptor partial agonists are described in Tissue-Selective Actions Of Estrogen Analogs, Bone Vol. 17, No. 4, October 1995, 181S-190S. Certain 3-[4-(2-phenylindol-1-ylmethyl)phenyl]acrylamides, described in U.S. Pat. No. 5,985,910 to Miller et al., Nov. 16, 1999; benzothiphene compounds, described in U.S. Pat. No. 5,985,897 to Meuhl et al., Nov. 16, 1999; naphthyl compounds, described in U.S. Pat. No. 5,952,350 to Cullinan et al., Sep. 14, 1999; substituted benzothiophene compounds, described in U.S. Pat. No. 5,962,475 to Schmid et al., Oct. 4, 1999, are suitable estrogen receptor partial agonists for administration with the compounds of Formula I; all of which patents and other documents referred to above are incorporated by reference herein in their entirety.

In a subclass of the invention, a pharmaceutical composition of this invention may comprise a therapeutically effect amount of a compound of Formula I in combination with one or more active ingredient(s) selected from the group consisting of (i) a therapeutically effect amount of a bisphosphonic acid or acid ester thereof or a pharmaceutically acceptable salt thereof and (ii) a therapeutically effect amount of an estrogen receptor modulator or a pharmaceutically acceptable salt thereof; and one or more pharmaceutically acceptable excipient(s). Non-limiting examples of such bisphosphonic acids include 4-amino-1-hydroxybutylidene-1,1-bisphosphonic acid, 1,1-dichloromethylene-1,1-diphosphonic acid, 1-hydroxy-3-pyrrolidin-1-ylpropylidene-1,1-bisphosphonic acid, 1-hydroxyethylidene-1,1-diphosphonic acid, 1-hydroxy-3-(N-methyl-N-pentylamino) propylidene-1,1-bisphosphonic acid, 6-amino-1-hydroxyhexylidene-1,1-bisphosphonic acid, 3-(dimethylamino)-1-hydroxypropylidene-1,1-bisphosphonic acid, 3-amino-1-hydroxypropylidene-1,1-bisphosphonic acid, 2-pyrid-2-ylethylidene-1,1-bisphosphonic acid, 1-hydroxy-2-pyrid-3-ylethylidene-1,1-bisphosphonic acid, 4-chlorophenylthiomethylenebisphosphonic acid and 1-hydroxy-2-(1H-imidazol-1-yl)ethylidene-1,1-bisphosphonic acid or acid ester thereof or a pharmaceutically acceptable salt thereof; particularly 4-amino-1-hydroxybutylidene-1,1-bisphosphonic acid, or a pharmaceutically acceptable salt thereof and preferably 4-amino-1-hydroxybutylidene-1,1-bisphosphonic acid, monosodium trihydrate.

EXAMPLES

The following preparations and examples are given to enable those skilled in the art to more clearly understand and to practice the present invention. They should not be considered as limiting the scope of the invention, but merely as being illustrative and representative thereof.

Example 1

Synthesis of trans-N-cyanomethyl-2-(4-fluorophenylsulfanylmethyl)-cyclohexanecarboxamide

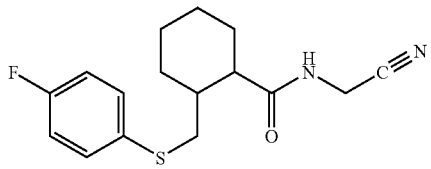

Step 1 trans-1,2-Cyclohexanedicarboxylic anhydride (19.64 g, 127 mmol) and aminoacetonitrile hydrochloride (12.05 g, 130 mmol) were weighed into a dry 500 mL flask fitted with a stir bar and nitrogen inlet. After adding anhydrous dichloromethane (200 mL), triethylamine (39.1 mL, 281 mmol) was added at a moderate rate, allowing the reaction to warm the solution to near boiling point. The reaction mixture was allowed to cool to room temperature over 1 h, after which it was cooled to −10° C. and isobutyl chloroformate (18.2 mL, 140 mmol) was added dropwise, keeping the reaction temperature below 0° C. After the addition was complete, the reaction was allowed to warm to room temperature. After 1 h, the reaction mixture was diluted with anhydrous tetrahydrofuran (200 mL) and stired at 0° C. for 1 h. The precipitate were filtered and washed with cold anhydrous tetrahydrofuran (100 mL). The filtrate was taken in a 1000 mL flask and fitted with a stir bar and a 50 mL addition funnel. The solution was cooled to −25° C. and a solution of sodium borohydride (6.90 g, 182 mmol) in water (30 mL) was added at a slow dropping rate, keeping the reaction temperature below −15° C. After the addition was complete, the reaction mixture was stirred for 1 h between −20° C. and −10° C. After warming the reaction mixture to warm to room temperature and stirring for an additional 1 h, anhydrous magnesium sulfate was added and stirring was continured for additional 30 min, filtered and the filtrate was concentrated on a rotary evaporator. Product was purified from the residue by chromatography using 9:1 dichloromethane:methanol eluent. The product fractions were concentrated on a rotary evaporator and dried under high vacuum to give trans-N-cyanomethyl-2-hydroxymethyl-cyclohexanecarboxamide as a white solid.

Step 2 trans-N-Cyanomethyl-2-hydroxymethyl-cyclohexanecarboxamide (12.4 g, 63.2 mmol) and triphenylphosphine (19.9 g, 75.8 mmol) were weighed into a 1000 mL round bottom flask fitted with a stir bar, addition port and nitrogen inlet. A nitrogen atmosphere was established and maintained and then anhydrous tetrahydrofuran (300 mL) was added. The reaction mixture was stirred for 30 minutes at room temperature and N-bromosuccinimide (13.5 g, 75.8 mmol) was added to the flask. The reaction slowly cleared to an orange-red solution. The reaction mixture was stirred at room temperature for 18 h and then concentrated on a rotary evaporator. Product was purified from the residue by chromatography on 2360 cm$^3$ of silica gel in a 10×30 cm column with ethyl acetate eluent. The product fractions were concentrated on a rotary evaporator and the residue dried under high vacuum to give trans-2-bromomethyl-N-cyanomethyl-cyclo-hexanecarboxamide as a white solid with a slight yellow tint.

Step 3 trans-2-Bromomethyl-N-cyanomethylcyclohexanecarboxamide (262 mg, 1 mmol) and cesium carbonate (331 mg, 1.02 mmol) were weighed into a 15 mL test tube fitted with a stir bar and vented cap and then acetone (3 mL) and 4-fluorobenzenethiol (106 μL, 1.01 mmol) were added sequentially to the test tube. The reaction mixture was stirred at 50° C. overnight and then diluted with hot acetone (7 mL). The reaction mixture was filtered through Celite™ and the filter funnel and Celite™ were washed with hot acetone (25 mL). The combined filtrate and wash were concentrated on a rotary evaporator and product was purified from the residue by chromatography on 40 cm$^3$ of silica gel in a 2×13 cm column with 9:1 dichloromethane:ethyl acetate eluent. The product fractions were concentrated on a rotary evaporator and the residue dried under high vacuum to give trans-N-cyanomethyl-2-(4-fluorophenylsulfanylmethyl)-cyclohexanecarboxamide as a waxy white solid. $^1$H NMR (DMSO-d6): δ 8.64 (1H, t), 7.33 (2H, m), 7.14 (2H, m), 4.13 (2H, d), 2.96 (1H, dd), 2.57 (1H, dd), 2.05 (2H, m), 1.70 (4H, m), 1.15 (4H, m). MS [ESI, (M−H)$^-$] m/z=305.0 amu.

Proceeding as in Example 1 provided the following compounds of Formula I:

trans-N-cyanomethyl-2-(4-bromophenylsulfanylmethyl) cyclohexanecarboxamide; $^1$H NMR (DMSO-d6): δ 8.66 (1H, t), 7.46 (2H, d), 7.23 (2H, d), 4.14 (2H, d), 2.98 (1H, dd), 2.61 (1H, dd), 2.03 (2H, m), 1.70 (4H, m), 1.15 (4H, m); MS [ESI, (M+H)$^+$] m/z=368.6 amu;

trans-N-cyanomethyl-2-(phenylsulfanylmethyl)cyclohexanecarboxamide; $^1$H NMR (CDCl$_3$): δ 7.28 (5H, m), 5.76 (1H, s), 4.03 (2H, dq), 3.04 (1H, dd), 2.81 (1H, dd), 1.9 (6H, m), 1.50 (1H, m), 1.25 (3H, m); MS [ESI, (M−H)] m/z=287.0 amu;

trans-N-cyanomethyl-2-(4-chlorophenylsulfanylmethyl) cyclohexanecarboxamide; $^1$H NMR (CDCl$_3$): δ 7.25 (4H, s), 5.82 (1H, t), 4.11 (2H, d), 3.01 (1H, dd), 2.74 (1H, dd), 2.0 (3H, m), 1.80 (3H, m), 1.52 (1H, m), 1.22 (3H, m);

trans-N-cyanomethyl-2-(3,4-dichlorophenylsulfanylmethyl)cyclohexanecarboxamide; $^1$H NMR (CDCl$_3$): δ 7.35 (2H, m), 7.13 (1H, dd), 5.89 (1H, t), 4.16 (2H, d), 3.02 (1H, dd), 2.71 (1H, dd), 2.02 (3H, m), 1.81 (3H, m), 1.54 (1H, m), 1.22 (3H, m); MS [ESI, (M−H)$^-$] m/z=355.0 amu;

trans-N-cyanomethyl-2-(4-methylphenylsulfanylmethyl) cyclohexanecarboxamide; $^1$H NMR (CDCl$_3$): δ7.26 (2H, d), 7.10 (1H, d), 5.68 (1H, t), 4.02 (2H, dq), 3.00 (1H, dd), 2.78 (1H, dd), 2.31 (3H, s), 2.12 (1H, dt), 1.8 (5H, m), 1.50 (1H, m), 1.24 (3H, m); MS [ESI, (M−H)$^-$] m/z=301.2 amu;

trans-N-cyanomethyl-2-(4-methoxyphenylsulfanylmethyl)cyclohexanecarboxamide; $^1$H NMR (CDCl$_3$): δ 7.32 (2H, d), 6.84 (1H, d), 5.78 (1H, t), 4.04 (2H, dd), 3.78 (3H, t), 2.93 (1H, dd), 2.73 (1H, dd), 2.11 (1H, dt), 1.8 (5H, m), 1.50 (1H, m), 1.24 (3H, m); MS [ESI, (M−H)$^-$] m/z=317.2 amu;

trans-N-cyanomethyl-2-[4-(morpholin-4-yl)phenylsulfanylmethyl]-cyclohexanecarboxamide; $^1$H NMR (DMSO-d6): δ 8.58 (1H, t), 7.18 (2H, d), 6.85 (2H, d), 4.09 (2H, d), 3.69 (4H, m), 3.06 (4H, m), 2.86 (1H, dd), 2.46 (1H, d), 2.01 (2H, m), 1.65 (4H, m), 1.15 (4H, m);

trans-N-cyanomethyl-2-(4-methylcarbonylaminophenylsulfanylmethyl)-cyclohexanecarboxamide; $^1$H NMR (DMSO-d6): δ 9.93 (1H, s), 8.63 (1H, t), 7.50 (2H, d), 7.22

(2H, d), 4.13 (2H, d), 2.94 (1H, dd), 2.53 (1H, dd), 2.05 (5H, m), 1.68 (4H, m), 1.15 (4H, m); MS [ESI, (M+H)+] m/z=346.0 amu;

trans-N-cyanomethyl-2-(4-nitrophenylsulfanylmethyl) cyclohexanecarboxamide; $^1$H NMR (DMSO-d6): δ 8.72 (1H, t), 8.11 (2H, d), 7.50 (2H, d), 4.16 (2H, d), 3.11 (1H, dd), 2.76 (1H, dd), 2.08 (2H, m), 1.78 (5H, m), 1.18 (3H, m); MS [ESI, (M–H)] m/z=332.0 amu;

trans-N-cyanomethyl-2-(4-tert-butylphenylsulfanylmethyl)cyclohexanecarboxamide; $^1$H NMR (DMSO-d6): δ 8.65 (1H, t), 7.30 (2H, d), 7.20 (2H, d), 4.14 (2H, d), 2.99 (1H, dd), 2.55 (1H, dd), 2.05 (2H, m), 1.73 (4H, m), 1.25 (12H, m), 0.96 (1H, m); MS [ESI, (M–H)$^-$] m/z=343.0 amu;

trans-N-cyanomethyl-2-(4-trifluoromethylphenylsulfanylmethyl)-cyclohexanecarboxamide; $^1$H NMR (DMSO-d6): δ 8.70 (1H, t), 7.61 (2H, d), 7.46 (2H, d), 4.16 (2H, d), 3.07 (1H, dd), 2.69 (1H, dd), 2.07 (2H, m), 1.77 (4H, m), 1.17 (4H, m); MS [ESI, (M-M) m/z=354.8 amu;

trans-N-cyanomethyl-2-(1-methylimidazol-2-ylsulfanylmethyl)-cyclohexanecarboxamide;

trans-N-cyanomethyl-2-(benzothiazol-2-ylsulfanylmethyl)cyclohexanecarboxamide;

trans-N-cyanomethyl-2-(benzoxazol-2-ylsulfanylmethyl) cyclohexanecarboxamide;

trans-N-cyanomethyl-2-(4,5-dihydrothiazol-2-ylsulfanyl-methyl)-cyclohexanecarboxamide;

trans-N-cyanomethyl-2-(pyrimidin-2-ylsulfanylmethyl) cyclohexanecarboxamide;

trans-N-cyanomethyl-2-(pyridin-4-ylsulfanylmethyl)cyclohexanecarboxamide;

trans-N-cyanomethyl-2-(6-chlorobenzoxazol-2-ylsulfanylmethyl)-cyclohexanecarboxamide;

trans-N-cyanomethyl-2-(5-methoxybenzthiazol-2-ylsulfanylmethyl)-cyclohexanecarboxamide; and trans-2-(4-methoxy-benzylsulfanylmethyl)-cyclohexanecarboxylic acid cyanomethyl-amide.

Example 2

Synthesis of trans-N-cyanomethyl-2-{4-[4-(4-tert-butoxycarbonylpiperazin-1-yl)phenyl] phenylsulfanylmethyl}cyclohexanecarboxamide a 250 mL pressure flask fitted with a stir bar and rubber septum. The flask was purged with nitrogen and then anhydrous dimethylformamide (200 mL) was added. The reaction mixture was sparged with nitrogen for one hour. Dichloro[1,1'-bis(diphenylphosphino)ferrocene]palladium (II) complex with dichloromethane (0.94 g, 1.3 mmol) was added and the flask was sealed with a Teflon™ screw cap. The reaction mixture was vigorously stirred at 85° C. for 2.5 h and then another portion of dichloro[1,1'-bis(diphenylphosphino)ferrocene]palladium(II) complex with dichloromethane (0.95 g, 1.3 mmol) was added. The reaction mixture was stirred at 85° C. for an additional 2.5 h, cooled to room temperature and let stand overnight. The reaction mixture was diluted with diethyl ether (q.s. 800 mL) and filtered through Celite™. The filtrate was concentrated on a rotary evaporator and product was purified from the residue by chromatography on 1300 cm$^3$ of silica gel in a 10×16.5 cm column with 1:1 hexane:ethyl acetate eluent. The product fractions were concentrated on a rotary evaporator and the residue dried under high vacuum to give 4-[4-(4,4,5,5-tetramethyl-[1,3,2]dioxaborolan-2-yl)-phenyl]piperazine-1-carboxylic acid tert-butyl ester as a cream colored solid.

Step 2

4-[4-(4,4,5,5-Tetramethyl-[1,3,2]dioxaborolan-2-yl)-phenyl]piperazine-11 carboxylic acid tert-butyl ester (396 mg, 1.02 mmol) and trans-N-cyanomethyl-2-(4-fluorophenylsulfanyl-methyl)-cyclohexanecarboxamide (631 mg, 1.72 mmol), prepared as in Example 1, were weighed into a 40 mL pressure tube fitted with a stir bar and rubber septum and then dimethylformamide (30 mL) was added forming a clear amber solution. The reaction mixture was stirred and a 2.0M aqueous solution of sodium carbonate (5.0 mL) was added dropwise. The reaction mixture was sparged with nitrogen for 20 minutes and then dichloro[1,1'-bis(diphenylphosphino)ferrocene]-palladium(II) complex with dichloromethane (51 mg, 0.070 mmol) was added. The tube was sealed with a Teflon™ screw cap and the reaction mixture was stirred vigorously at 100° C. overnight. The reaction mixture was diluted with ethyl acetate (50 mL) and filtered through a short plug of silica gel. The plug was washed with ethyl acetate (50 mL) and the combined filtrate and wash

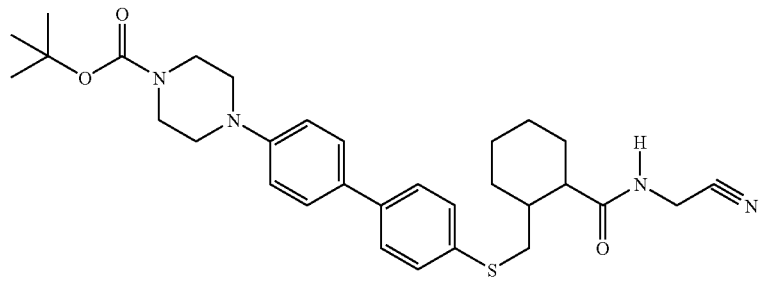

tep 1

1-tert-Butoxycarbonyl-4-(4-bromophenyl)piperazine (15.2 g, 44.5 mmol), pinacol diborane (13.6 g, 53.6 mmol) and potassium acetate (13.2 g, 134 mmol) were weighed into were concentrated on a rotary evaporator. The residue was recrystallized from 12 mL 1:1 methanol:acetonitrile to give trans-N-cyanomethyl-2-{4-[4-(4-tert-butoxycarbonylpiperazin-1-yl)phenyl]phenylsulfanylmethyl}-cyclohexanecarboxamide as a light tan solid.

Example 3

Synthesis of trans-N-cyanomethyl-2-[4-(4-piperazin-1-lphenyl)phenylsulfanylmethyl)-cyclohexanecarboxamide

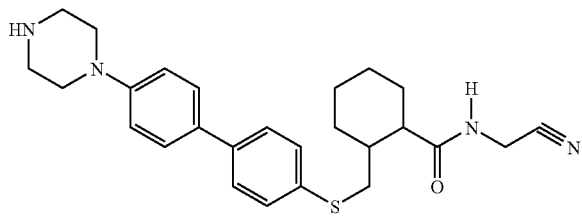

trans-N-Cyanomethyl-2-{4-[4-(4-tert-butoxycarbonylpiperazin-1-yl)phenyl]-phenylsulfanylmethyl}cyclohexanecarboxamide (152 mg, 0.277 mmol), prepared as in Example 2, was weighed into a 20 mL vial fitted with a cap. The vial was purged with nitrogen and then anhydrous dioxane (5 mL) was added. The reaction mixture was warmed at 50° C. until all the solids dissolved and then let stand at room temperature overnight. The precipitate was removed by filtration through a 0.45 μm Teflon™ syringe filter into a 20 mL vial fitted with a stir bar and cap. The reaction mixture was cooled in an ice/water bath and then stirred rapidly while methanesulfonic acid add (115 μL, 1.69 mmol) was added dropwise. The vial was purged with nitrogen and sealed with cap. The reaction mixture was stirred at room temperature for 5 h. The reaction was quenched with diisopropylethylamine (350 μL) and the reaction mixture was concentrated on a rotary evaporator. Product was purified from the residue by chromatography on C-18 reverse phase HPLC. Product fractions were pooled by absorbance at 214 nm, freeze and lyophilize to give trans-N-cyanomethyl-2-[4-(4-piperazin-1-ylphenyl)phenylsulfanylmethyl)-cyclohexanecarboxamide as a white solid. $^1$H NMR (DMSO-d6): δ 8.80 (1H, br s), 8.68 (1H, t), 7.56 (4H, t), 7.33 (2H, d), 7.06 (2H, d), 4.15 (2H, d), 3.39 (4H, d), 3.25 (4H, s), 3.04 (1H, dd), 2.61 (1H, dd), 2.08 (2H, m), 1.70 (4H, m), 1.17 (4H, m). MS [ESI, (M+H)$^+$] m/z=449.4 amu.

Example 4

Synthesis of trans-N-cyanomethyl-2-(4-fluorobenzenesulfonylmethyl)-cyclohexanecarboxamide

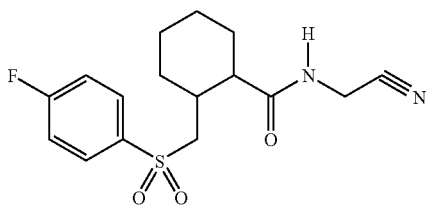

trans-N-cyanomethyl-2-(4-fluorophenylsulfanylmethyl) cyclohexanecarboxamide (239 mg, 0.780 mmol), prepared as in Example 1, was weighed into a 100 mL round bottom flask fitted with a stir bar and vented cap and the methanol (30 mL) was added to the flask. The reaction mixture was stirred at 50° C. until a clear colorless solution formed and then a 0.3M aqueous solution of Oxone™ (3.15 mL, 0.945 mmol) was added. A white precipitate formed. The reaction mixture was stirred at 50° C. overnight and then concentrated on a rotary evaporator. The residue was partitioned water (20 mL) and dichloromethane (20 mL). The aqueous phase was separated and extracted with dichloromethane. The combined organic phase was washed with water (10 mL) and brine (15 mL), dried over magnesium sulfate and concentrated on a rotary evaporator to give trans-N-cyanomethyl-2-(4-fluorobenzenesulfonylmethyl)cyclohexanecarboxamide as a white solid. $^1$H NMR (DMSO-d6): δ 8.57 (1H, t), 7.91 (2H, m), 7.48 (2H, m), 4.06 (2H, d), 3.22 (1H, dd), 2.96 (1H, dd), 2.08 (3H, m), 1.67 (3H, m), 1.32 (1H, m), 1.14 (3H, m). MS [ESI, (M–H)$^-$] m/z=337.2 amu.

Proceeding as in Examples 3 and 4 and utilizing appropriate starting materials provided the following compounds of Formula I:

trans-N-cyanomethyl-2-(4-bromobenzenesulfonylmethyl)cyclohexanecarboxamide; $^1$H NMR (DMSO-d6): δ 8.57 (1H, t), 7.86 (2H, d), 7.76 (2H, d), 4.05 (2H, d), 3.23 (1H, dd), 2.97 (1H, dd), 2.05 (3H, m), 1.65 (3H, m), 1.20 (4H, m); MS [ESI, (M–H)$^-$] m/z=396.8 amu;

trans-N-cyanomethyl-2-[4-(morpholin-4-yl)benzenesulfonylmethyl]-cyclohexanecarboxamide; $^1$H NMR (DMSO-d6): δ=8.55 (1H,??t), 7.58 (2H, d), 7.05 (2H, d), 4.04 (2H, m), 3.72 (4H, m), 3.31 (2H, m), 3.15 (4H, m), 2.10 (2H, m), 1.64 (4H, m), 1.15 (4H, m); MS [ESI, (M+H)$^+$] m/z=406.4 amu;

trans-N-cyanomethyl-2-(benzenesulfonylmethyl)cyclohexanecarboxamide; $^1$H NMR DMSO-d6): δ 8.58 (1H, t), 7.75 (5H, m), 4.06 (2H, d), 3.19 (1H, dd), 2.96 (1H, dd), 2.05 (3H, m), 1.65 (3H, m), 1.32 (1H, m), 1.1 (3H, m); MS [ESI, (M–H)$^-$] m/z=319.2 amu;

trans-N-cyanomethyl-2-(4-chlorobenzenesulfonylmethyl)cyclohexanecarboxamide; $^1$H NMR (DMSO-d6): δ 8.58 (1H, t), 7.85 (2H, d), 7.72 (2H, d), 4.06 (2H, d), 3.24 (1H, dd), 2.97 (1H, dd), 2.05 (3H, m), 1.66 (3H, m), 1.31 (1H, m), 1.14 (3H, m); MS [ESI, (M–H)$^-$] m/z=353.2 amu;

trans-N-cyanomethyl-2-(3,4-dichlorobenzenesulfonylmethyl)cyclohexanecarboxamide; $^1$H NMR (DMSO-d6): δ 8.59 (1H, t), 8.07 (1H, d), 7.93 (1H, d), 7.81 (1H, dd), 4.06 (2H, d), 3.33 (1H, dd), 3.02 (1H, d), 2.05 (3H, m), 1.67 (3H, m), 1.32 (1H, m), 1.16 (3H, m); MS [ESI, (M–H)$^-$] m/z=387.0 amu;

trans-N-cyanomethyl-2-(4-methylbenzenesulfonylmethyl)cyclohexanecarboxamide; $^1$H NMR (DMSO-d6): δ 8.57 (1H, t), 7.85 (2H, d), 7.44 (2H, d), 4.06 (2H, d), 3.14 (1H, dd), 2.93 (1H, dd), 2.41 (3H, s), 2.07 (3H, m), 1.66 (3H, m), 1.32 (1H, m), 1.12 (3H, m); MS [ESI, (M–H)$^-$] m/z=333.2 amu;

trans-N-cyanomethyl-2-(4-methoxybenzenesulfonylmethyl)cyclohexanecarboxamide; $^1$H NMR (DMSO-d6): δ 8.56 (1H, t), 7.75 (2H, d), 7.14 (2H, d), 4.06 (2H, d), 3.86 (3H, s), 3.11 (1H, dd), 2.92 (1H, d), 2.07 (3H, m), 1.66 (3H, m), 1.32 (1H, m), 1.14 (3H, m); MS [ESI, (M–H)$^-$] m/z=349.0 amu;

trans-N-cyanomethyl-2-(4-methylcarbonylaminobenzenesulfonylmethyl)-cyclohexanecarboxamide;

trans-N-cyanomethyl-2-(4-nitrobenzenesulfonylmethyl) cyclohexanecarboxamide;

trans-N-cyanomethyl-2-(4-tert-butylbenzenesulfonylmethyl)cyclohexanecarboxamide;

trans-N-cyanomethyl-2-(4-methylsulfonylbenzenesulfonylmethyl)-cyclohexanecarboxamide;

trans-N-cyanomethyl-2-(4-aminobenzenesulfonylmethyl) cyclohexanecarboxamide;

trans-N-cyanomethyl-2-(4-trifluoromethylbenzenesulfonylmethyl)-cyclohexanecarboxamide;

trans-2-(4-methoxybenzylsulfonylmethyl)-cyclohexanecarboxylic acid cyanomethyl-amide;

trans-N-cyanomethyl-2-(4-hydroxybenzenesulfonylmethyl)cyclohexanecarboxamide;

trans-N-cyanomethyl-2-(1-methylimidazol-2-ylsulfonylmethyl)-cyclohexanecarboxamide; and trans-N-cyanomethyl-2-14-[2-(4-isopropylpiperazin-1-yl)thiazol-4-yl]
phenylsulfonylmethyl}cyclohexanecarboxamide.

Example 5

Synthesis of trans-N-cyanomethyl-2-(4-bromophenylsulfinylmethyl)-cyclohexanecarboxamide

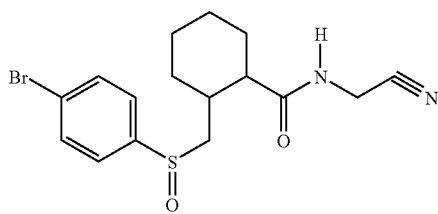

trans-N-Cyanomethyl-2-(4-bromophenylsulfanylmethyl)cyclohexanecarboxamide (197 mg, 0.536 mmol), prepared as in Example 1 but substituting 4-fluorothiophenol with 4-bromothiophenol, was weighed into a 50 mL round bottom flask fitted with a stirrer and vented cap. Methanol (20 mL) was added to the flask and the reaction mixture was warmed to 50° C. until a clear colorless solution formed. Added sodium periodate (128 mg, 0.599 mmol) solution in water (2.0 mL). A white precipitate slowly formed. The reaction mixture was stirred at 50° C. for 8 h and then concentrated on a rotary evaporator. The residue was triturated in hot water (20 mL) and the reaction mixture was cooled to room temperature. Solids were isolated by filtration, washed thoroughly with water and dried under high vacuum to give trans-N-cyanomethyl-2-(4-bromophenylsulfinylmethyl)cyclohexanecarboxamide as a white solid.

$^1$H NMR (DMSO-d6): 68.60 (1H, t), 7.76 (2H, d), 7.23 (2H, d), 4.09 (2H, d), 2.62 (2H, m), 2.05 (3H, m), 1.71 (3H, m), 1.28 (4H, m). MS [ESI, (M+H)$^+$] m/z=384.8 amu.

Example 6

Synthesis of trans-N-cyanomethyl-2-(4-ethoxycarbonylmethylsulfanylbenzenesulfonyl-methyl)cyclohexanecarboxamide

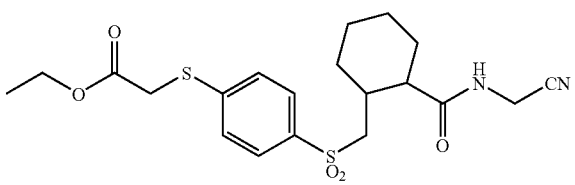

trans-N-Cyanomethyl-2-(4-fluorobenzenesulfonylmethyl)cyclohexanecarboxamide (3.384 g, 10 mmol) and potassium carbonate (2.34 g, 17 mmol) were weighed into a 100 mL round bottom flask fitted with a stir bar and a cap. Ethyl 2-mercaptoacetate (1.86 mL) was added, followed by the addition of dimethylformamide (30 mL). The reaction vessel was flushed with nitrogen and then sealed with a cap. After stirring the reaction mixture at 100° C. for 2 h, the reaction mixture was allowed to stir overnight at room temperature. The reaction mixture was diluted with ethyl acetate (300 mL), filtered, and washed with brine. The organic layer was dried over magnesium sulfate, filtered and evaporated on a rotavap. The residue was chromatographed on 500 cm$^3$ of silica gel in a 5×25 cm column with 50:50 dichloromethane:ethyl acetate eluent to give the title compound as a white solid. $^1$H NMR (DMSO-d6): =8.59 (1H, t), 7.69 (2H,dd), 7.49 (2H,dd), 4.44-4.04 (6H, m), 3.37 (1H, q), 2.95 (1H, dd), 2.2-1.8(3H, m), 1.62 (3H, m), 1.30 (1H, m), 1.16 (6H, m) MS [ESI, (M−H)$^-$] m/z=437.2 amu Example 7

Synthesis of trans-N-cyanomethyl-2-(4-carboxymethylsulfanylbenzenesulfonylmethyl)cyclohexanecarboxamide

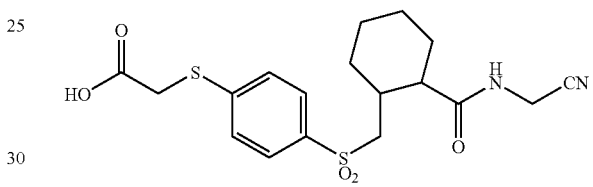

trans-N-Cyanomethyl-2-(4-ethoxycarbonylsulfanylmethylbenzenesulfonylmethyl)cyclohexane-carboxamide (3 g, 6.8 mmol) was dissolved in methanol (100 mL) in a 250 mL round bottom flask filled with a stir bar and a cap. A solution of lithium hydroxide monohydrate (0.3779 g, 9 mmol) in water (30 mL) was added and the reaction mixture was stirred at room temperature for 1 h. The solvents were removed and the aqueous residue was neutralized with 1N HCl. The product was extracted with ethyl acetate, dried and concentrated to give the title compound as a white solid. $^1$H NMR (DMSO-d6): δ=10.85 (1H, s), 8.59 (1H, t), 7.69 (2H,dd), 7.49 (2H,dd), 4.04 (2H, d), 3.80 (2H, s), 3.37 (1H, q), 2.95 (1H, dd), 2.15 (3H, m), 1.62 (3H, m), 1.30 (1H, m), 1.16 (3H, m). MS [ESI, (M−H)$^-$] m/z=409.3 amu.

Amide Synthesis-General Procedure trans-N-Cyanomethyl-2-(4-carboxymethylsulfanylbenzenesulfonylmethyl)cyclohexane-carboxamide (100 mg, 0.24 mmol) was weighed in 10 mL vial fitted with a stir bar and a cap. HATU (109 mg, 0.288 mmol) and the desired amine (0.48 mmol) were added and the reaction mixture was dissolved in dry dimethylformamide (1 mL). The reaction mixture was flushed with nitrogen and the reaction vessel was sealed with a cap. After stirring the reaction mixture for a few minutes at room temperature, diisopropylethylamine (125 μl, 0.72 mmol) was added and stirring was continued overnight. The reaction mixture was diluted with ethyl acetate (10 mL), washed with saturated solution of sodium bicarbonate (3 mL). The organic layer was dried over magnesium sulfate, filtered and concentrated. Chromatography of the residue on C-18 reverse phase HPLC followed by lyophilization provided the desired amide. Following this general procedure and using commercially available amines, the following compounds of Formula I were synthesized.

trans-N-Cyanomethyl-2-(4-pyridin-4-ylmethylaminocarbonylmethylsulfanylbenzenesulfonylmethyl)cyclohexanecarboxamide. ¹H NMR (DMSO-d6): δ=9.01 (1H, t), 8.73 (2H, d), 8.59 (1H, t), 7.69 (4H, d), 7.52 (2H,d), 4.51 (2H, d), 4.04 (2H, d), 3.97 (2H, s), 3.16 (1H, q), 2.94 (1H, dd), 2.04 (3H, m), 1.67 (3H, m), 1.29 (1H, m), 1.46 (3H, m). MS [ESI, (M+H)⁺] m/z=501.2 amu.

trans-N-Cyanomethyl-2-[4-(2-thien-2-ylethylaminocarbonylmethylsulfanyl)benzenesulfonylmethyl]cyclohexanecarboxamide. ¹H NMR (DMSO-d6): o=8.55 (1H, t), 8.36 (1H, t), 7.68 (2H, dd), 7.47 (2H, dd), 7.30 (1H, d), 6.90 (1H, t), 6.82 (1H, d), 4.04 (2H, d), 3.79 (2H, s), 3.29 (2H, m), 3.15 (1H, q), 2.91 (3H, m), 2.01 (3H, m), 1.61 (3H, m), 1.30 (1H, m), 1.13 (3H, m). MS [ESI, (M+H)+] m/z=520.2 amu.

trans-N-Cyanomethyl-2-[4-(2-chlorobenzylaminocarbonylmethylsulfanyl)benzenesulfonylmethyl]cyclohexanecarboxamide. ¹H NMR (DMSO-d6): δ=8.73 (1H, t), 8.56 (1H, t), 7.69 (2H, dd), 7.53 (2H, dd), 7.40 (1H, d), 7.23 (3H, m), 4.33 (2H, d), 4.04 (2H, d), 3.90 (2H, s), 3.15 (1H, q), 2.93 (1H, dd), 2.05 (3H, m), 1.66 (3H, m), 1.30 (1H, m), 1.12 (3H, m). LC/MS m/z=534.3 amu.

trans-N-Cyanomethyl-2-[4-(4-methoxybenzylaminocarbonylmethylsulfanyl)benzenesulfonylmethyl]cyclohexanecarboxamide. ¹H NMR (DMSO-d6): δ=8.62 (1H, t), 2.55 (1H, t), 7.67 (2H, dd), 7.49 (2H, dd), 7.08 (2H, dd), 6.82 (2H, dd), 4.19 92H, d), 4.04 (2H, d), 3.83 (2H, s), 3.70 (3H, s), 3.15 (1H, q), 2.95 (1H, dd), 2.01 (3H, m), 1.62 (3H, m), 1.15 (1H, m), 1.13 (3H, m). MS [ESI, (M+H)+] m/z=530.1 amu.

trans-N-Cyanomethyl-2-[4-(4-chlorobenzylaminocarbonylmethylsulfanyl)benzenesulfonylmethyl]cyclohexanecarboxamide. ¹H NMR (DMSO-d6): δ=8.74 (1H, t), 8.56 (1H, t), 7.68 (2H, dd), 7.50 (2H, dd), 7.32 (2H, dd), 7.17 (2H, dd), 4.25 (2H, d), 4.04 (2H, d), 3.86 (2H, s), 3.16 (1H, q), 2.93 (1H, dd), 2.04 (3H, m), 1.64 (3H, m), 1.29 (1H, m), 1.12 (3H, m). LC/MS m/z=534.2 amu.

trans-N-Cyanomethyl-2-[4-(3-dimethylaminobenzylaminocarbonylmethylsulfanyl)-benzenesulfonylmethyl]cyclohexanecarboxamide. ¹H NMR ¹H-¹H NMR (DMSO-d6): δ=8.68 (1H, t), 8.56 (1H, t), 7.66 (2H, dd), 7.50 (2H, dd), 7.15 (1H, t), 6.75 (2H, s), 6.62 (1H, d), 4.23 (2H, d), 4.04 (2H, d), 3.85 (2H, s), 3.15 (1H, q), 2.95 (1H, dd), 2.91 (6H, s), 2.0 (3H, m), 1.61 3H, m), 1.30 (1H, m), 1.13 (3H, m). MS [ESI, (M+H)⁺] m/z=543.1 amu.

trans-N-Cyanomethyl-2-[4-(4-pyridin-4-ylpiperazin-1-ylcarbonylmethylsulfanyl)-benzene-sulfonylmethyl]cyclohexanecarboxamide. ¹H NMR (DMSO-d6): δ=8.58 (1H, t), 8.26 (2H, d), 7.69 (2H, dd), 7.53 (2H, d), 7.18 (2H, d), 4.28 (2H, s), 4.04 (2H, d), 3.68 (8H, m), 3.15 (1H, q), 2.93 (1H, dd), 2.04 (3H, m), 1.61 (3H, m), 1.30 (1H, m), 1.13 (3H, m). MS [ESI, (M+H)⁺] m/z=556.3 amu.

trans-N-Cyanomethyl-2-[4-(1-benzylpiperidin-4-ylaminocarbonylmethylsulfanyl)-benzenesulfonylmethyl]cyclohexanecarboxamide. ¹H NMR (DMSO-d6): δ 8.58 (1H, t), 8.41 (1H, d), 7.67 (2H, d), 7.48 (7H, dd), 4.30 (5H, m), 4.03 (2H, d), 3.77 (3H, m), 3.58 (1H, s) 3.13 (5H, m), 1.92 (4H, m), 1.61 (4H, m), 1.10 (4H, m). MS [ESI, (M+H)⁺] m/z=583.0 amu Thioether Synthesis—General Procedure trans-2-Bromomethylcyclohexanecarboxylic acid cyanomethylamide (1 mmol) and cesium carbonate (1 mmol) were weighed into a vial (15 mL) fitted with a stir bar and vented cap. Acetone (3 mL) and the desired thiol were added and the reaction mixture was stirred at 50° C. overnight. The reaction mixture was diluted with hot acetone (7 mL) and the hot solution was filtered through Celite™. The Celite™ was washed with hot acetone (25 mL). The combined filtrate and wash were concentrated and the crude product was purified by chromatography.

Example 8

Synthesis of trans-N-cyanomethyl-2-(4-methylsulfanylbenzenesulfonylmethyl)cyclohexanecarboxamide

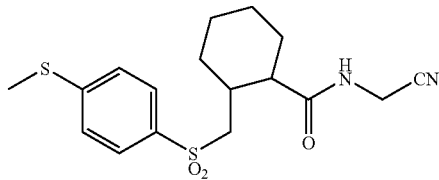

trans-N-Cyanomethyl-2-(4-fluorobenzenesulfonylmethyl)-cyclohexanecarboxamide (102 mg) was weighed into a 2.5 mL vial fitted with a stir vane and nitrogen inlet. Anhydrous toluene (1.5 mL) was added, followed by addition of sodium thiomethoxide (22 mg). The reaction mixture was heated to 70° C. and stirred overnight. After cooling to room temperature, the reaction mixture was stirred for two days. The reaction mixture was diluted with ethyl acetate (15 mL), washed with water and brine. The organic layer was removed, dried over magnesium sulfate and concentrated on a rotary evaporator. Chromatography of the crude product on C-18 reverse-phase HPLC provided the title compound as a white solid.

¹H NMR (DMSO-d6): δ=8.56 (1H, t), 7.68 (2H, d), 7.43 (2H, d), 4.05 (2H, d), 3.14 (1H, dd), 2.92 (1H, d), 2.54 (3H, s), 2.1 (1H, d), 2.0 (2H, m), 1.7 (3H, m), 1.3 (1H, m), 1.1 (3H, m) MS [ESI, (M–H)⁻] m/z=365.2 amu Example 9

Synthesis of trans-N-cyanomethyl-2-[4-(3-hydroxypropylsulfanyl)benzenesulfonylmethyl]cyclohexanecarboxamide

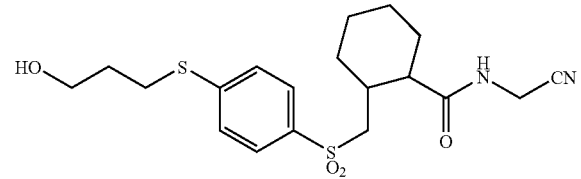

trans-N-Cyanomethyl-2-(4-fluorobenzenesulfonylmethyl)-cyclohexanecarboxamide (101 mg) and potassium carbonate (73 mg) were weighed into a 5 mL vial fitted with a stir bar and cap. Dimethylformamide (1 mL) and 3-mercapto-1-propanol (45 µL) were added. The vial was flushed with nitrogen and sealed with a cap. After stirring the reaction mixture at 100° C. for 6 h, the reaction mixture was allowed to cool to room temperature and stirred overnight. The reaction mixture was diluted with acetonitrile (4 mL) and filtered to remove solids. Concentration of the filtrate followed by chromatography of the crude residue on C-18 reverse-phase HPLC provided the desired product as a white solid. ¹H NMR (DMSO-d₆): δ=8.56 (1H, t), 7.68 (2H, m), 7.46 (2H, m), 4.05 (2H, d), 3.49 (2H, t), 3.14 (3H, m), 2.92 (1H, d), 2.2 (1H, m), 2.0 (2H, m), 1.8 (2H, m), 1.7 (3H, m), 1.3 (1H, m), 1.13 (3H, m). MS [ESI, (M−H)⁻] m/z=409.3 amu Example 10

Synthesis of trans-N-cyanomethyl-2-(4-methylsulfanylphenylsulfanylmethyl)-Cyclohexanecarboxamide

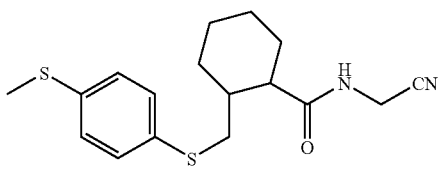

trans-2-Bromomethyl-cyclohexanecarboxylic acid cyanomethyl-amide (258 mg) and cesium carbonate (329 mg) were weighed into a 15 mL vial fitted with a stir bar and a vent cap. Acetone (3 mL) and 4-(methylsulfanyl)thiophenol (162 mg) were added. The reaction mixture was stirred at 50° C. overnight and then diluted with hot acetone (7 mL) and filtered through Celite™. The Celite™ was washed with hot acetone. The filtrate and wash were combined and the solvent was removed on a rotary evaporator. Chromatography of the crude product on a silica gel (using 9:1 dichloromethane: acetone as the eluent) provided the title compound as a white solid. ¹H NMR (DMSO-d6): δ=8.63 (1H, t), 7.24 (2H, d), 7.18 (2H, d), 4.13 (2H, d), 2.97 (1H, dd), 2.58 (1H, m), 2.96 (3H, s), 2.1 (2H, m), 1.7 (4H, m), 1.2 (4H, m) MS [ESI, (M−H)⁻] m/z=332.8 amu Example 11

Synthesis of trans-N-cyanomethyl-2-(4-hydroxyphenylsulfanylmethyl)-cyclohexanecarboxamide

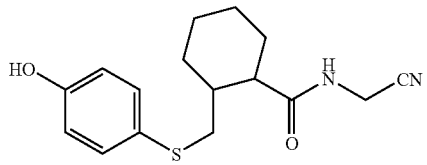

trans-2-Bromomethyl-cyclohexanecarboxylic acid cyanomethylamide (261 mg) and cesium carbonate (327 mg) were weighed into a 15 mL vial fitted with a stir bar and a vent cap. Acetone (3 mL) and 4-mercaptophenol (139 mg) were added. The reaction mixture was stirred at 50° C. overnight and then diluted with hot acetone (7 mL) and filtered through Celite™. The Celite™ was washed with hot acetone. The filtrate and wash were combined and the solvent was removed on a rotary evaporator. Chromatography of the crude product on a silica gel (using 3:1 dichloromethane:acetone as the eluent) provided the title compound as a beige solid.

¹H NMR (DMSO-d6): δ=9.48 (1H, s), 8.59 (1H, t), 7.15 (2H, d), 6.70 (2H, d), 4.11 (2H, d), 2.85 (1H, dd), 2.5 (1H, m), 2.0 (2H, m), 1.7 (4H, m), 1.2 (4H, m). MS [ESI, (M−H)⁻] m/z=303.2 amu Example 12

Synthesis of trans-N-cyanomethyl-2-[4-(4-sulfanylphenylsulfanyl)-phenylsulfanylmethyl)-cyclohexanecarboxamide

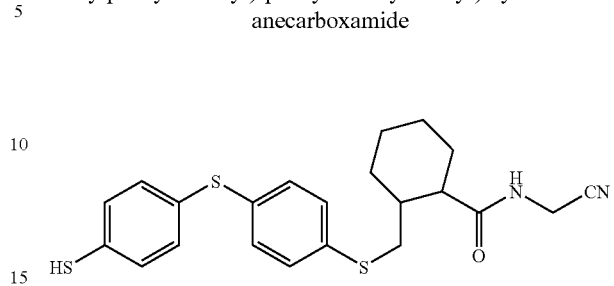

trans-2-Bromomethyl-cyclohexanecarboxylic acid cyanomethylamide (259 mg) and cesium carbonate (340 mg) were weighed into a 15 mL vial fitted with a stir bar and a vent cap. Acetone (3 mL) and 4-mercaptothiophenol (256 mg) were added. The reaction mixture was stirred at 50° C. overnight and then diluted with hot acetone (7 mL) and filtered through Celite™. The Celite™ was washed with hot acetone (25 mL). The filtrate and wash were combined and the solvent was removed on a rotary evaporator. Chromatography of the crude product on C-18 reverse-phase HPLC provided the title compound as a cream solid. ¹H NMR (DMSO-d6): δ=8.65 (1H, t), 7.46 (2H, dd), 7.27 (4H, d), 7.21 (2H, dd), 4.12 (2H, d), 3.50 (1H, br m), 2.98 (1H, d), 2.6 (1H, m), 2.1 (2H, m), 1.7 (4H, m), 1.1 (4H, m).

Example 13

Synthesis of trans-N-cyanomethyl-2-(4-furan-2-ylmethylsulfanyl)(benzenesulfonylmethyl)-cyclohexanecarboxamide

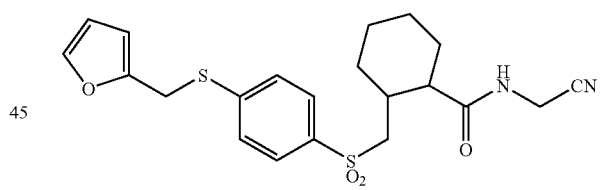

trans-N-Cyanomethyl-2-(4-fluorobenzenesulfonylmethyl)-cyclohexanecarboxamide (101 mg) (101 mg) and cesium carbonate (196 mg) were weighed into a 5 mL glass vial fitted with a stir bar and cap. Dimethylformamide (2 mL) and furfuryl mercaptan (60 μL) were added. The vial was flushed with nitrogen and sealed with a cap. The reaction mixture was stirred at 100° C. for 2 days and monitored by TLC and LC-MS. The reaction mixture was diluted with acetonitrile (10 mL) and filtered through a 1 g C-18 prep cartridge, using acetonitrile (10 mL) wash. The filtrate was concentrated and the residue was chromatographed on C-18 reverse-phase HPLC to give the title compound as a beige solid. ¹H NMR (DMSO-d₆): δ=8.49 (1H, t), 7.62 (2H, d), 7.48 (3H, m), 6.28 (2H, s), 4.37 (2H, s), 3.98 (2H, d), 3.10 (1H, dd), 2.86 (1H, d), 2.0 (3H, m), 1.6 (3H, m), 1.3 (1H, m), 1.1 (3H, m). MS [ESI, (M−H)⁻] m/z=430.9 amu.

Example 14

Synthesis of trans-N-cyanomethyl-2-[4-(2-morpholin-4-ylethylaminocarbonylmethylsulfanyl)-benzenesulfonylmethyl]-cyclohexanecarboxamide trifluoroacetate salt

trifluoroacetate salt trans-N-Cyanomethyl-2-(4-carboxymethylbenzenesulfonylmethyl)cyclohexane-carboxamide (150 mg) was weighed in 5 mL vial fitted with a stir bar and a cap. O-(7-Azabenzotriazol-1-yl)-1,1,3,3-tetramethyluronium hexafluorophosphate (109 mg) was added, followed by addition of a solution of 4-(2-aminoethyl)morpholine (96 μL) and diisopropylethylamine (200 μL) in dimethylformamide (2.0 mL). The vial was purged with nitrogen and sealed with the cap. After stirring the reaction mixture at room temperature overnight, it was diluted with methanol (5 mL) and filtered through a 1 g C-18 prep cartridge and the cartridge was washed with methanol (20 mL). The solvent was removed and the residue was chromatographed on C-18 reverse-phase HPLC to give the title compound as a white solid. $^1$H NMR (DMSO-d6): δ=9.76 (1H, br m), 8.56 (1H, t), 8.52 (1H, t), 7.70 (2H, d), 7.49 (2H, d), 4.05 (2H, d), 3.96 (2H, m), 3.85 (2H, s), 3.64 (2H, m), 3.44 (4H, m), 3.2-3.0 (5H, m), 2.94 (1H, d), 2.2 (1H, d), 2.0 (2H, m), 1.7 (3H, m), 1.3 (1H, m), 1.1 (3H, m). MS [ESI, (M–H)$^-$] m/z=523.1 amu

Example 15

Synthesis of trans-N-cyanomethyl-2-[4-(pyridin-3-ylaminocarbonylmethylsulfanyl)-benzene-sulfonylmethyl]cyclohexanecarboxamide trifluoroacetate salt

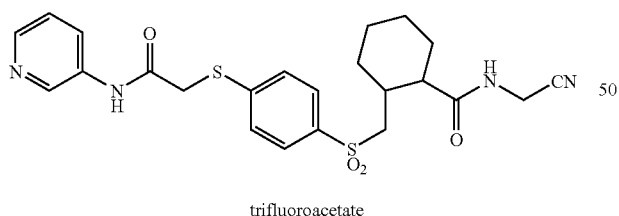

trifluoroacetate trans-N-Cyanomethyl-2-(4-carboxymethylbenzenesulfonylmethyl)cyclohexane-carboxamide (148 mg) was weighed in 5 mL vial fitted with a stir bar and a cap. O-(7-Azabenzotriazol-1-yl)-1,1,3,3-tetramethyluronium hexafluorophosphate (179 mg) was added. 3-Aminopiperidine dihydrochloride (127 mg) and potassium carbonate (103 mg) were mixed in dimethylformamide (2.0 mL) and the reaction mixture was warmed to 60° C. and stirred for 30 rin. The reaction mixture was cooled to room temperature and diisopropylethylamine (400 μL) was added. The solution was decanted away from the solids into the reaction mixture containing the cyclohexanecarboxamide. The vial was purged with nitrogen, sealed with the cap and stirred at room temperature overnight. The reaction mixture was diluted with 5 mL methanol and filtered through a 1 g C-18 prep cartridge, using 20 mL methanol wash. The solvent was removed on a rotary evaporator and the residue was chromatographed on C-18 reverse-phase HPLC to provide the title compound as a white solid. MS [ESI, (M–H)$^-$] m/z=491.3 amu

Example 16

Synthesis of trans-N-cyanomethyl-2-[4-(4-isopropylpiperazin-1-ylcarbonylmethylsulfanyl)-benzenesulfonylmethyl]cyclohexanecarboxamide trifluoroacetate salt

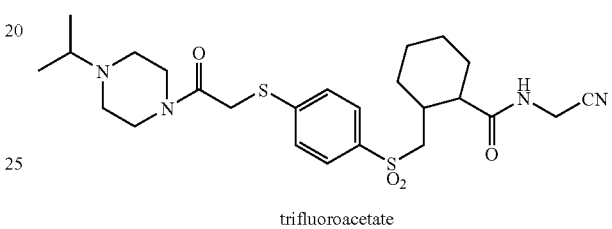

trifluoroacetate trans-N-Cyanomethyl-2-(4-carboxymethylbenzenesulfonylmethyl)cyclohexane-carboxamide (149 mg) was weighed in 5 mL vial fitted with a stir bar and a cap. O-(7-Azabenzotriazol-1-yl)-1,1,3,3-tetramethyluronium hexafluorophosphate (187 mg), 1-isopropylpiperazine (95 mg) and diisopropylethylamine (200 μL) in dimethylformamide (2 mL) were added. The vial was purged with nitrogen, sealed with the cap and stirred at room temperature overnight. The reaction mixture was diluted with 5 mL methanol and filter through a 1 g C-18 prep cartridge, using 20 mL methanol wash. The solvent was removed on a rotary evaporator and the residue was chromatographed on C-18 reverse-phase HPLC to provide the title compound as a white solid. $^1$H NMR (DMSO-d6): δ=9.64 (1H, br m), 8.59 (1H, t), 7.68 (2H, d), 7.52 (2H, d), 4.47 (1H, m), 4.28 (2H, s), 4.25 (1H, m), 4.04 (2H, d), 3.49 (5H, m), 3.13 (2H, m), 2.95 (3H, m), 2.2 (1H, m), 2.0 (2H, m), 1.7 (3H, m), 1.3 (1H, m), 1.25 (6H, d), 1.1 (3H, m). MS [ESI, (M–H)$^-$] m/z=519.3 amu

Example 17

Synthesis of trans-N-(cyanomethyl)-2-({[4-(methylsulfanyl)phenyl]sulfanyl}-methyl)cyclopentanecarboxamide

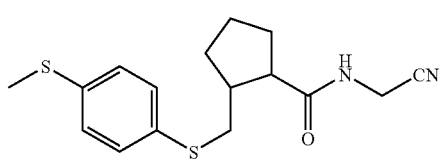

Step 1

A mixture of cyclopentane-1,2-dicarboxylic acid (2.12 g, 13.4 mmol) in methanol (150 mL) and concentrated hydrochloric acid (0.75 mL) was heated at reflux for 16 h. The reaction mixture was concentrated by rotary evaporation under reduced pressure and the residue was partitioned between ether (150 mL) and saturated sodium bicarbonate aqueous solution (150 mL). The organic layer was separated and dried over anhydrous magnesium sulfate. The organics were removed to give cyclopentane-1,2-dicarboxylic acid dimethyl ester as a colorless liquid.

Step 2

Cyclopentane-1,2-dicarboxylic acid dimethyl ester (2.50 g, 13.4 mmol) was dissolved in methanol (2.5 mL) and a solution of potassium hydroxide (85% purity) (920 mg, 13.9 mmol) in methanol (4.0 mL) and water (0.5 mL) in a 25 mL round bottom flask. The reaction mixture was heated at 75° C. for 4 h. The reaction mixture was cooled to 0° C. and acidified to pH 2 with 2M HCl in water. The reaction mixture was diluted with water (100 mL) and extracted with ether. The organic layer was dried over anhydrous magnesium sulfate and concentrated on a rotary evaporator to give cyclopentane-1,2-dicarboxylic acid monomethyl ester as a faint-yellow liquid.

Step 3

Cyclopentane-1,2-dicarboxylic acid monomethyl ester (2.21 g, 12.8 mmol), 2-aminoacetonitrile hydrochloride (1.48 g, 16.0 mmol) and benzotriazol-1-yloxy)tripyrrolidinophosphonium hexafluorophosphate (PyBOP) (7.34 g, 14.1 mmol) were dissolved in dimethylformamide (26 mL) and the reaction mixture was cooled to 0° C. Triethylamine (4.9 mL, 35 mmol) was added and the reaction mixture was stirred at ambient temperature for 3 h. The reaction mixture was partitioned between water (150 mL) and ethyl acetate (100 mL). The product was extracted into ethyl acetate, washed with saturated sodium chloride aqueous solution, dried over anhydrous sodium sulfate and concentrated. The residue was chromatographed on silica gel with 3:2 ethyl acetate:hexanes eluent to give methyl trans-2-{[(cyanomethyl)amino]carbonyl}cyclopentanecarboxylate as a colorless solid.

Step 4

Methyl trans-2-{[(cyanomethyl)amino]carbonyl}cyclopentanecarboxylate (1.08 g, 5.16 mmol) in ethylene glycol dimethyl ether (6.5 mL) was cooled to 0° C. 2.00 M aqueous sodium hydroxide (2.65 mL) was added and the reaction mixture was stirred at 0° C. for 3.5 h. The pH was adjusted to 5 with 2 M aqueous hydrochloric acid and the reaction mixture was diluted with water. The product was extracted into ethyl acetate, washed with saturated sodium chloride aqueous solution, dried over anhydrous sodium sulfate and concentrated to give trans-2-{[(cyanomethyl)amino]carbonyl}cyclopentanecarboxylic acid as a colorless solid.

Step 5 trans-2-{[(Cyanomethyl)amino]carbonyl}cyclopentanecarboxylic acid (860 mg, 4.38 mmol) was placed in a 50 mL round bottom flask. The flask was fitted with a rubber septum and then flushed with nitrogen. Tetrahydrofuran (9 mL) was added and the reaction mixture was cooled to −78° C. 4-Methylmorpholine (0.53 mL, 4.8 mmol) was added, followed by addition of isobutyl chloroformate (0.61 mL, 4.7 mmol). The reaction mixture was warmed to ambient temperature over 1.5 h and then recooled to −78° C. Sodium borohydride (0.28 g, 7.4 mmol) was added and then methanol (3.0 mL). The reaction mixture was stirred at −78° C. for 2 h and then quenched with saturated aqueous ammonium chloride (10 mL). The reaction mixture was warmed to ambient temperature and then poured into 100 mL saturated aqueous sodium chloride solution. The product was extracted into ethyl acetate. The combined organics were dried over anhydrous sodium sulfate and then concentrated on a rotary evaporator. Toluene (5 mL) was added to the residue and the reaction mixture was stirred for 30 min. The solution was removed by decantation and the residue was dried under high vacuum to give trans-N-(cyanomethyl)-2-(hydroxymethyl)-cyclopentanecarboxamide as a colorless solid.

Step 6 trans-N-(Cyanomethyl)-2-(hydroxymethyl)cyclopentane carboxamide (11 mg, 63 mmol) and triphenylphosphine (19 mg, 72 mmol) were placed in a 1 mL vial and dimethylformamide (0.15 mL) was added. The reaction mixture was cooled to 0° C. and diisopropyl azodicarboxylate (14 μL, 69 μmol) was added. After stirring for 10 min., 4-(methylsulfanyl)thiophenol (11 μL, 72 μmol) was added and the reaction mixture was stirred at ambient temperature for 1 h. The reaction mixture was partitioned between ethyl acetate (10 mL) and 1:1 water:saturated aqueous sodium chloride (10 mL). The product was extracted into ethyl acetate. The combined organic phase was dried with anhydrous sodium sulfate and then concentrated on a rotary evaporator. Chromatography of the residue on silica gel eluting with 2:3 ethyl acetate:hexanes provided the title compound as a colorless solid. $^1$H NMR (500 MHz, acetone-d6): δ=7.75 (1H, br s), 7.29 (2H, d), 7.21 (2H, d), 4.21 (2H, d), 3.10 (1H, dd), 2.89 (1H, dd), 2.51 (1H, q), 2.46 (3H, s), 2.43 (1H, m), 1.99-1.90 (2H, m), 1.75 (1H, m), 1.70-1.61 (2H, m), 1.40 (1H, m). MS [ESI, (M−H)$^-$] m/z=319.2 amu Example 18

Synthesis of (1S/R,3R/S,4R/S,6R/S)-N-(cyanomethyl)-4-({[4-(methylsulfanyl)phenyl]sulfanyl}-methyl)bicyclo[4.1.0]heptane-3-carboxamide

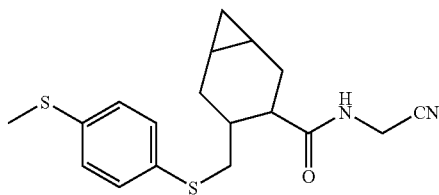

Step 1

A 25 mL round bottom flask was fitted with a rubber septum and flushed several times with nitrogen gas. 1,2-Dichloroethane (2 mL) and diethylzinc (0.23 mL, 2.3 mmol) were added. The reaction mixture was cooled down to 0° C. and then chloroiodomethane (0.34 mL, 4.7 mmol) was added in a dropwise manner. After stirring for 10 min., a solution of methyl trans-6-(bromomethyl)cyclohex-3-ene-1-carboxylate (500 mg, 2.2 mmol) (see Christol, H.; Donche, A.; Plenat, M. F. *Bull. Chim. Soc. Fr.* 1966, 1315-24) in 2.2 mL of 1,2-dichloroethane was added in a dropwise fashion. After stirring the reaction mixture at 0° C. for 1 h, then at ambient temperature for 1 h, the reaction mixture was poured in saturated ammonium chloride aqueous solution (75 mL). The organics were extracted in ether, the extracts were dried over anhydrous magnesium sulfate and then concentrated on a rotary evaporator to give methyl(1S/R, 3R/S,4R/S,6R/S)-4-(bromomethyl)bicyclo[4.1.0]heptane-3-carboxylate.

Step 2

Methyl(1S/R,3R/S,4R/S,6R/S)(bromomethyl)bicyclo [4.1.0]heptane-3-carboxylate was dissolved in dimethylformamide (4.0 mL) and potassium carbonate (920 mg, 6.7 mmol) was added. After adding 4-(methylsulfanyl)thiophenol (390 mg, 2.5 mmol), the reaction mixture was stirred at ambient temperature for 20 h. The reaction mixture was partitioned between ether (75 mL) and water (75 mL). The product was extracted into ether and the combined ethereal layers were dried with anhydrous sodium sulfate. After removing the organics, the residue was chromatographed on silica gel using a mixture of ethyl acetate and hexanes (gradient elution from 5:95 to 10:90) to give methyl(1S/R, 3R/S,4R/S,6R/S)-4-({[4-(methylsulfanyl)phenyl]-sulfanyl}-methyl)bicyclo[4.1.0]heptane-3-carboxylate.

Step 3

Methyl(1S/R,3R/S,4R/S,6R/S)-4-({[4-(methylsulfanyl) phenyl]-sulfanyl}-methyl)bicyclo[4.1.0]heptane-3-carboxylate was dissolved in ethylene glycol dimethyl ether (3.0 mL) and methanol (1 mL) in a 25 mL round bottom flask. Aqueous solution of lithium hydroxide (3.0 mL, 6.0 mmol, 2 M) was added and the reaction mixture was stirred at ambient temperature for 36 h. After acidification with 2 M aqueous hydrochloric acid to pH 3, the product was extracted into ether. The combined ether extracts were washed with saturated aqueous sodium chloride solution, dried over anhydrous sodium sulfate, and concentrated by rotary evaporation to give (1S/R,3R/S,4R/S,6R/S)-4-({[4-(methylsulfanyl)phenyl]sulfanyl}-methyl)bicyclo[4.1.0] heptane-3-carboxylic acid.

Step 4

To a mixture of aminoacetonitrile hydrochloride (153 mg, 1.65 mmol) and benzotriazol-1-yloxy)tripyrrolidinophosphonium hexafluorophosphate (PyBOP) (800 mg, 1.54 mmol) was added 1S/R,3R/S,4R/S,6R/S)-4-({[4-(methylsulfanyl)phenyl]sulfanyl}methyl)bicyclo[4.1.0]-heptane-3-carboxylic acid and dimethylformamide (4 mL). After adding triethylamine (0.52 mL, 3.7 mmol) the reaction mixture was stirred at ambient temperature for 4 h. The reaction mixture was partitioned between water and ethyl acetate. The product was extracted into ethyl acetate and the combined organic phases were washed with saturated sodium chloride aqueous solution and dried over anhydrous sodium sulfate. The solvents were removed and the residue was chromatographed on a silica gel with methanol:dichloromethane (1.5:98.5) as eluent to give crude product which was purified in 1.4 mg portions by preparative RP HPLC (Waters, RCM, C18, μBondapak, 1×24 mm) by gradient elution with acetonitrile:water (containing 25 mM ammonium acetate)/30:70 to 50:50, 6.0 mL/min flowrate, UV detector set at 300 nM to give the title compound as a colorless solid. $^1$H NMR (500 MHz, acetone-d6): δ=7.83 (1H, br s), 7.28 (2H, d), 7.19 (2H, d), 4.20 (2H, m), 3.12 (1H, dd), 2.62 (1H, dd), 2.46 (3H, s), 2.26 (1H, m), 2.21 (1H, m), 2.10 (1H, m), 1.67 (1H, m), 1.58 (1H, m), 1.52 (1H, m), 0.99 (1H, m), 0.90 (1H, m), 0.57 (1H, m), −0.06 (1H, m). MS [ESI, (M−H)] m/z=345.2 amu.

Example 19

Synthesis of (1R/S,2R/S,3R/S,4S/R)-N-(cyanomethyl)-3-{[(4-fluorobenzenesulfonyl]methyl}-bicyclo[2.2.1]hept-5-ene-2-carboxamide

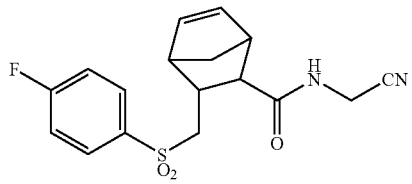

Step 1

To 5-norbornene-2-endo-3-exo-dicarboxylic acid (4.07 g, 22.3 mmol) in a 500 mL round bottom flask was added 100 mL water. Sodium bicarbonate was added (4.40 g, 110 mmol) in portions. Potassium iodide (4.81 g, 29.0 mmol) and iodine (7.40 g, 29.2 mmol) were added and the reaction mixture was stirred at ambient temperature for 4 h. 2 M aqueous NaHSO₃ was added until the iodine color disappeared and then 6 M aqueous hydrochloric acid was added carefully till the pH of the solution was 2. The product was extracted into dichloromethane. The combined extracts were washed with water, dried over sodium sulfate and concentrate to give (3R/S,3aR/S,5S/R,6S/R,6aS/R,7S/R)-6-iodo-2-oxohexahydro-2H-3,5-methanocyclopenta[b]-furan-7-carboxylic acid as a colorless powder.

Step 2

To (3R/S,3aR/S,5S/R,6S/R,6aS/R,7S/R)-6-iodo-2-oxohexahydro-2H-3,5-methano-cyclopenta[b]furan-7-carboxylic acid (1.51 g, 4.90 mmol) was added aminoacetonitrile hydrochloride (502 mg, 5.43 mmol) and) benzotriazol-1-yloxy)tripyrrolidinophosphonium hexafluorophosphate (2.56 g, 4.91 mmol. After adding dimethylformamide (10 mL), the reaction mixture was cooled to 0° C. and triethylamine (1.7 mL, 12 mmol) was added. After stirring the reaction mixture at ambient temperature for 4.5 h, the product was extracted into ethyl acetate. The combined organic phases were washed with saturated sodium chloride aqueous solution, dried over anhydrous sodium sulfate, and concentrated. Chromatography of the residue on silica gel with 1:1 ethyl acetate:hexanes eluent gave (3R/S,3aR/S,5S/ R,6S/R,6aS/R,7S/R)-N-(cyanomethyl)-6-iodo-2-oxo-hexahydro-2H-3,5-methanocyclopenta[b]furan-7-carboxamide as a colorless syrup.

Step 3

To (3R/S,3aR/S,5S/R,6S/R,6aS/R,7S/R)-N-(cyanomethyl)-6-iodo-2-oxohexahydro-2H-3,5-methanocyclopenta [b]furan-7-carboxamide (1.45 g, 4.18 mmol) was added tetrahydrofuran (10 mL) and zinc dust (11.0 g, 170 mmol). 1 M aqueous KH₂PO₄ (21 mL, 21 mmol) was added and the reaction mixture was stirred at ambient temperature for 1 h. The reaction mixture was diluted with water and ethyl acetate and filtered through Celite™ and the Celite™ was washed well with water and ethyl acetate. The product was extracted into ethyl acetate and the combined extracts were washed with saturated aqueous sodium chloride solution. The organics were dried with anhydrous sodium sulfate and then concentrated on a rotary evaporator to give (1S,2R,3R, 4R)-3-{[(cyanomethyl)amino]carbonyl}bicyclo[2.2.1]hept-5-ene-2-carboxylic acid as a faint-yellow solid.

Step 4

(1S,2R,3R,4R)-3-{[(Cyanomethyl)amino]carbonyl}bicyclo[2.2.1]hept-5-ene-2-carboxylic acid (840 mg, 3.81 mmol) was placed in a 25 mL round bottom flask and the flask was fitted with a rubber septum. After flushing the flask with nitrogen, tetrahydrofuran (8.0 mL) was added and the solution was cooled to −78° C. 4-Methylmorpholine (0.46 mL, 4.0 mmol) and isobutyl chloroformate (0.52 mL, 4.0 mmol) were added and the reaction mixture was stirred at −78° C. for 10 min., and then warmed to ambient temperature over 1 h. After stirring for an additional 1 h, the reaction mixture was recooled to −78° C. and sodium borohydride (0.25 g, 6.5 mmol) and methanol (6.0 mL) were added. After stirring for 1 h, the reaction mixture was allowed to warm to ambient temperature over 1 hour and then quenched with saturated aqueous ammonium chloride. The reaction mixture was diluted with saturated aqueous sodium chloride solution (100 mL) and the product was extracted with ethyl acetate. The combined organics were dried over anhydrous sodium sulfate and then concentrated on a rotary evaporator. Chromatography of the residue on a silica gel using a mixture ethyl acetate:hexanes (gradient elution 5:2 to 3:1) provided (1R/S,2R/S,3R/S,4S/R)-N-(cyanomethyl)-3-(hydroxymethyl)bicyclo[2.2.1]hept-5-ene-2-carboxamide as a colorless solid.

Step 5

A solution of triphenylphosphine (120 mg, 460 µmol) in dimethylformamide (1.0 mL) was cooled to 0° C. Diisopropyl azodicarboxylate (83 µL, 420 µmol) was added and the reaction mixture was stirred for 2 min. (1R/S,2R/S,3R/S,4S/R)-N-(cyanomethyl)-3-(hydroxymethyl)-bicyclo[2.2.1]hept-5-ene-2-carboxamide (79 mg, 380 µmol) and 4-fluorothiophenol (45 µl, 420 µmol) were added and the reaction mixture was stirred at ambient temperature for 2.5 h. The reaction mixture was partitioned between ethyl acetate (10 mL) and 1:1 water:saturated aqueous sodium chloride (10 mL). The product was extracted into ethyl acetate, dried with anhydrous sodium sulfate and concentrated. Chromatography of the residue on silica gel eluting with 4:96 methanol:dichloromethane provided (1R/S,2R/S,3R/S,4S/R)-N-(cyanomethyl)-3-{[(4-fluorophenyl)sulfanyl]methyl}bicyclo[2.2.1]hept-5-ene-2-carboxamide as a colorless syrup.

Step 6

(1R/S,2R/S,3R/S,4S/R)-N-(Cyanomethyl)-3-{[(4-fluorophenyl)sulfanyl]methyl}-bicyclo[2.2.1]hept-5-ene-2-carboxamide (17 mg, 54 µmol) was placed into a 2 mL vial and tetrahydrofuran (0.20 mL), methanol (0.20 mL), and saturated aqueous sodium bicarbonate solution (0.30 mL), were added. Oxone™ (70 mg, 110 mmol) was added and the reaction mixture was stirred at ambient temperature for 1.5 h. The reaction mixture was partitioned between 1 mL water and 1 mL ethyl acetate. The product was extracted into ethyl acetate and the combined organics were washed with 1 mL saturated aqueous sodium chloride solution, dried over anhydrous sodium sulfate and concentrated using a rotary evaporator. Chromatography of the residue on a silica gel using 1:4 acetone:benzene as eluent provided the title compound as a colorless, waxy solid. $^1$H NMR (500 MHz, acetone-d6): δ=7.98 (2H, d), 7.78 (1H, br s), 7.41 (2H, t), 6.26 (1H, dd), 6.11 (1H, dd), 4.23 (2H, m), 3.27 (1H, dd), 2.95-2.83 (4H, m), 2.79 (1H, m), 1.75 (1H, d), 1.29 (1H, dd). MS [ESI, (M−H)$^-$] m/z=347.1 amu.

Example 20

Synthesis of (1S/R,2R/S,3R/S,4R/S)-N-(cyanomethyl)-3-({[4-(methylsulfanyl)benzene]-sulfonyl}methyl)bicyclo[2.2.1]heptane-2-carboxamide

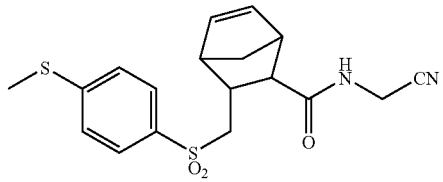

Step 1

(1R/S,2R/S,3R/S,4S/R)-N-(Cyanomethyl)-3-(hydroxymethyl)bicyclo[2.2.1]hept-5-ene-2-carboxamide (96 mg, 460 µmol) was placed in a 25 mL round bottom flask and 10% palladium on activated charcoal (11 mg) and ethyl acetate were added (5.0 mL). The flask was fitted with a rubber septum, flushed several times with nitrogen and then stirred under hydrogen atmosphere for 6 h. After flushing the reaction mixture with nitrogen, 10 mL ethyl acetate was added and then filtered through a Celite™ plug. The plug was washed with two 5 mL portions of ethyl acetate. The solvent was removed on a rotary evaporator to give (1S/R, 2R/S,3R/S,4R/S)-N-(cyanomethyl)-3-(hydroxymethyl)bicyclo[2.2.1]heptane-2-carboxamide as a colorless solid.

Step 2

A solution of triphenylphosphine (140 mg, 540 mmol) in dimethylformamide (1.0 mL) was cooled to 0° C. Diisopropyl azodicarboxylate (98 µL, 500 µmol) was added and the reaction mixture was stirred for 2 min. (1R/S,2R/S,3R/S,4S/R)-N-(Cyanomethyl)-3-(hydroxymethyl)bicyclo[2.2.1]hept-5-ene-2-carboxamide (94 mg, 450 µmol) and 4-fluorothiophenol (53 µL, 500 µmol) were added. After stirring the reaction mixture for 19 h, it was partitioned between ethyl acetate (20 mL) and 1:1 water:saturated aqueous sodium chloride (20 mL). The product was extracted into ethyl acetate and the combined organics were washed with 1 mL saturated aqueous sodium chloride solution, dried over anhydrous sodium sulfate and concentrated using a rotary evaporator. Chromatography of the residue on silica gel eluting with 1:2 ethyl acetate:hexanes provided (1S/R,2R/S,3R/S,4R/S)-N-(cyanomethyl)-3-{[(4-fluorophenyl)sulfanyl]methyl}bicyclo[2.2.1]heptane-2-carboxamide as a colorless syrup.

Step 3

(1S/R,2R/S,3R/S,4R/S)-N-(cyanomethyl)-3-{[(4-fluorophenyl)sulfanyl]methyl}bicyclo-[2.2.1]heptane-2-carboxamide (56 mg, 180 mmol) was placed into a 10 mL round bottom flask. Tetrahydrofuran (0.70 mL), methanol (0.70 mL) and saturated aqueous sodium bicarbonate solution (1.1 mL) were added. After adding Oxone™ (250 mg, 410 mmol), the reaction mixture was stirred at ambient temperature for 1 h. The product was extracted into ethyl acetate and the combined organics were washed with 1 mL saturated aqueous sodium chloride solution, dried over anhydrous sodium sulfate and concentrated using a rotary evaporator to give (1S/R,2R/S,3R/S,4R/S)-N-(cyanomethyl)-3-{[(4-fluorobenzenesulfonyl]methyl}bicyclo[2.2.1]-heptane-2-carboxamide as a colorless foam.

Step 4

(1S/R,2R/S,3R/S,4R/S)-N-(Cyanomethyl)-3-{[(4-fluorobenzenesulfonyl]methyl}bicyclo-[2.2.1]heptane-2-carboxamide (22 mg, 63 μmol) was placed into a 10 mL round bottom flask and dimethylformamide (1.6 mL) and sodium thiomethoxide (86 mg, 1.2 mmol) were added. After stirring for 5 h, the product was extracted into ethyl acetate and the combined organics were washed with 1 mL saturated aqueous sodium chloride solution, dried over anhydrous sodium sulfate and concentrated using a rotary evaporator. Chromatography of the residue on a silica gel using a 16:84 mixture of acetone:benzene provide the title compound as a colorless foam. $^1$H NMR (500 MHz, acetone-d6): δ=7.78 (2H, d), 7.65 (1H, br s), 7.44 (2H, d), 4.25 (1H, dd), 4.16 (1H, dd), 3.34 (1H, dd), 3.23 (1H, dd), 2.66 (1H, m), 2.58 (3H, s), 2.26 (1H, m), 2.22 (1H, m), 1.64 (1H, m), 1.59-1.45 (2H, m), 1.38-1.21 (2H, m), 1.20-1.11 (2H, m). MS [APCI, (M–H)$^-$] m/z=377.1 amu.

Example 21

Synthesis of (5R/S,6R/S)-N-(cyanomethyl)-6-{[(4-fluorophenyl)sulfanyl]methyl}spiro[2.4]-heptane-5-carboxamide

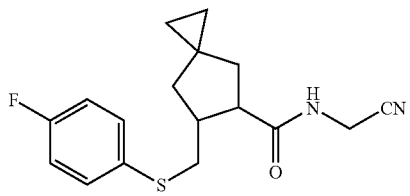

Step 1

To a 25 mL round bottom flask fitted with a rubber septum and flushed several times with nitrogen gas was added 1,2-dichloroethane (5.0 mL) and diethylzinc (0.56 mL, 5.5 mmol). The reaction mixture was cooled to 0° and chloroiodomethane (0.90 mL, 12 mmol) was added dropwise and the reaction mixture was stirred for 10 min. A solution of diethyl 4-methylenecyclopentane-trans-1,2-dicarboxylate (560 mg, 2.5 mmol) (see Gais, H.-J.; Bulow, G.; Zatorski, A.; Jentsch, M.; Maidonis, P.; Hemmerle, H. *J. Org. Chem.* 1989, 54, 5115-5122) in 1,2-dichloroethane (5 mL) was added dropwise and the reaction mixture was stirred at 0° C. for 40 min., and then at ambient temperature for 2 h. The reaction mixture was poured into saturated ammonium chloride aqueous solution and the product was extracted into ether. The combined extracts were dried over anhydrous magnesium sulfate and concentrated. The tan colored oily residue was dissolved in methanol (5.0 mL) and cooled to −78° C. Ozone was bubbled into the solution for 15 min. Dimethyl sulfide (1 mL) was added and the stirring was continued at ambient temperature overnight. The solvent was removed and the residue was chromatographed on a silica gel using 1:9 ethyl acetate:hexanes as eluent to give diethyl spiro[2.4]heptane-trans-5,6-dicarboxylate as a colorless oil.

Step 2

To a solution of diethyl spiro[2.4]heptane-trans-5,6-dicarboxylate (200 mg, 0.83 mmol) in ethanol (0.80 mL), add a solution of potassium hydroxide (70 mg, 1.1 mmol) (85% purity) in ethanol (0.50 mL) and water (0.10 mL). After stirring the reaction mixture at ambient temperature for 4 h, it was cooled to 0° C. and then acidified to pH 2 with 2 M HCl in water. The reaction mixture was diluted with 50 mL water and extracted with ether. The combined ether phases were washed with saturated aqueous sodium chloride solution, dried over anhydrous magnesium sulfate and concentrated on a rotary evaporator to give trans-6-(ethoxycarbonyl)spiro[2.4]heptane-5-carboxylic acid as a colorless oil.

Step 3 trans-6-(Ethoxycarbonyl)spiro[2.4]heptane-5-carboxylic acid (165 mg, 832 mmol) was placed in a 25 mL round bottom flask. After flushing the flask with nitrogen, tetrahydrofuran (1.6 mL) was added and the reaction mixture was cooled to −78° C. 4-Methylmorpholine (0.11 mL, 1.0 mmol) and isobutyl chloroformate (0.12 mL, 0.93 mmol) were added and the reaction mixture was allowed to warm to ambient temperature. After 15 min., the reaction mixture was recooled to −78° C. and sodium borohydride (60 mg, 1.6 mmol) was added. Methanol (1.3 mL) was added and the reaction mixture was warmed to ambient temperature over 2 h and then quenched with saturated aqueous ammonium chloride. The reaction mixture was diluted with saturated aqueous sodium chloride solution and the product was extracted with ethyl acetate. The combined organics were dried over anhydrous sodium sulfate and then concentrated on a rotary evaporator. Chromatography of the residue on silica gel using 35:65 ethyl acetate:hexanes as eluent provided ethyl(5R/S,6R/S)-6-(hydroxymethyl)spiro[2.4]heptane-5-carboxylate as a colorless oil.

Step 4

A solution of triphenylphosphine (240 mg, 910 μmol) in dimethylformamide (1.1 mL) was cooled to 0° C. Diisopropyl azodicarboxylate (0.16 mL, 0.81 mmol) was added and the reaction mixture was stirred for 5 min. Ethyl(5R/S,6R/S)-6-(hydroxymethyl)spiro[2.4]heptane-5-carboxylate (100 mg, 0.54 mmol) and 4-fluorothiophenol (86 μL, 0.81 mmol) in dimethylformamide (1.7 mL) were added. After stirring the reaction mixture for 19 h, it was partitioned between ethyl acetate (30 mL) and 1:1 water:saturated aqueous sodium chloride (30 mL). The product was extracted into ethyl acetate and the combined organics were washed with saturated aqueous sodium chloride solution, dried over anhydrous sodium sulfate and concentrated using a rotary evaporator. Chromatography of the residue on silica gel eluting with 5:95 ethyl acetate:hexanes provided ethyl(5R/S,6R/S)-6-{[(4-fluorophenyl)sulfanyl]methyl}-spiro[2.4]heptane-5-carboxylate as a colorless oil.

Step 5

To a solution of ethyl(5R/S,6R/S)-6-{[(4 fluorophenyl)sulfanyl]methyl}spiro[2.4]-heptane-5-carboxylate (66 mg, 0.22 mmol) in 0.3 mL methanol was added ethylene glycol dimethyl ether (1.0 mL) and 2 M aqueous solution of lithium hydroxide (1.0 mL). The reaction mixture was stirred at ambient temperature for 22 h and then poured into 30 mL water. The reaction mixture was washed with 30 mL ether and the aqueous layer was acidified with a 2 M aqueous solution of hydrochloric acid. The product was extracted into ethyl acetate and the combined ethyl acetate extracts were washed with saturated aqueous sodium chloride solution, dried over anhydrous sodium sulfate, and concentrated to give (5R/S,6R/S)-6-{[(4-fluorophenyl)sulfanyl]methyl}spiro[2.4]heptane-5-carboxylic acid as a colorless syrup.

Step 6

To (5R/S,6R/S)-6-{[(4-fluorophenyl)sulfanyl]methyl}spiro[2.4]heptane-5-carboxylic acid (59 mg, 0.21 mmol) was added aminoacetonitrile hydrochloride (30 mg, 0.32 mmol) and benzotriazol-1-yloxy)tripyrrolidinophosphonium hexafluorophosphate (120 mg, 0.23 mmol) and dimethylformamide (0.70 mL). The reaction mixture was cooled to 0° C. and triethylamine (90 PL, 0.65 mmol) was added. After stirring for 11 h, the reaction mixture was partitioned between water and ethyl acetate. The organic layer was separated and washed with saturated sodium chloride aqueous solution, dried over anhydrous sodium sulfate, and concentrated. Chromatography of the residue on silica gel with 35:65 ethyl acetate:hexanes provided the title compound as a of a colorless, waxy solid. $^1$H NMR (500 MHz, acetone-d6): δ=7.76 (1H, br s), 7.40 (2H, dd), 7.08 (2H, t), 4.22 (2H, d), 3.15 (1H, dd), 2.93 (1H, dd), 2.75 (1H, dd), 2.66 (1H, m), 1.90 (1H, dd), 1.86 (1H, dd), 1.50 (1H, dd), 0.45 (4H, m). MS [APCI, (M–H)$^-$] m/z=317.0 amu.

Example 22

Synthesis of (5R/S,6R/S)-N-(cyanomethyl)-6-{[(4-fluorobenzene)sulfonyl]methyl}spiro[2.4]-heptane-5-carboxamide

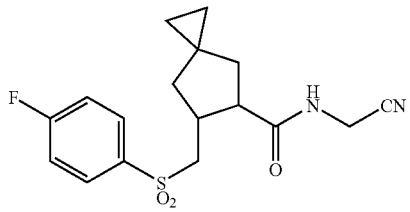

(5R/S,6R/S)-N-(Cyanomethyl)-6-{[(4-fluorophenyl)sulfanyl]methyl}spiro[2.4]heptane-5-carboxamide (55 mg, 0.17 mmol) was placed into a 10 mL round bottom flask and tetrahydrofuran (1.0 mL), methanol (1.0 mL), and water (1.0 mL) were added. After adding sodium bicarbonate (280 mg, 3.3 mmol), Oxone™ (270 mg, 0.44 mmol) were added and the reaction mixture was stirred at ambient temperature for 2.5 h. The reaction mixture was partitioned between water and ethyl acetate, the organic layer was separated and washed with saturated aqueous sodium chloride solution. The organics were dried with anhydrous sodium sulfate and concentrated to give the title compound as a colorless, waxy solid.

$^1$H NMR (400 MHz, acetone-d6): δ=8.00 (2H, m), 7.73 (1H, br s), 7.44 (2H, m), 4.20 (2H, m), 3.48 (1H, dd), 3.32 (1H, dd), 2.89-2.70 (2H, m), 1.94 (1H, m), 1.83 (2H, m), 1.60 (1H, m), 0.48 (4H, m). MS [APCI, (M–H)$^-$] m/z=349.0 amu.

Example 23

Synthesis of (1R/S,6R/S)-N-(Cyanomethyl)-6-{[(4-fluorophenyl)sulfanyl]methyl}-cyclohex-3-ene-1-carboxamide

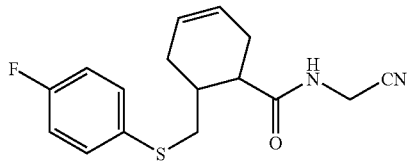

Methyl trans-6-(bromomethyl)cyclohex-3-ene-1-carboxylate (710 mg, 3.05 mmol) (Christol, H.; Donche, A.; Plenat, M. F. *Bull. Chim. Soc. Fr.* 1966, 1315-24) was placed in a 25 mL round bottom flask and dimethylformamide (6.0 mL) was added, followed by addition of potassium carbonate (1.26 g, 9.12 mmol) and 4-fluorothiophenol (0.40 mL, 3.8 mmol). After stirring the reaction mixture for 2 h, it was partitioned between ether and water. The organic layer was separated and the aqueous phase was extracted with an additional 75 mL portion of ether. The combined ethereal layers were washed with saturated aqueous sodium chloride solution, dried over anhydrous sodium sulfate, and concentrated. Chromatography of the residue on a silica gel using a 6:94 mixture of ethyl acetate:hexanes provided methyl(1R/S,6R/S)-6-{[(4-fluorophenyl)sulfanyl]methyl lcyclohex-3-ene-1-carboxylate of a colorless liquid.

Step 2

A solution of methyl(1R/S,6R/S)-6-{[(4-fluorophenyl)sulfanyl]methyl}cyclohex-3-ene-1-carboxylate (656 mg, 2.34 mmol) in methanol (1.0 ml) and ethylene glycol dimethyl ether (5.0 ml) was treated with a 2 M aqueous solution of lithium hydroxide (6.0 ml). After stirring for 19 h, the reaction mixture was adjusted to pH 2 with a 2 M aqueous solution of hydrochloric acid and partitioned between water and ethyl acetate. After separating the organic phase, the aqueous phase was extracted with an additional portion of ethyl acetate. The combined extracts were washed with saturated aqueous sodium chloride solution and dried over anhydrous sodium sulfate. Removal of the solvent on a rotary evaporator provided (1R/S,6R/S)-6-{[(4-fluorophenyl)sulfanyl]methyl}cyclohex-3-ene-1-carboxylic acid as a golden-yellow syrup.

Step 3

(1R/S,6R/S)-6-{[(4-Fluorophenyl)sulfanyl]methyl}cyclohex-3-ene-1-carboxylic acid (620 mg, 2.34 mmol) was weighed into a 25 mL round bottom flask and aminoacetonitrile hydrochloride (480 mg, 5.20 mmol) and benzotriazol-1-yloxy)tripyrrolidinophosphonium hexafluorophosphate (1.34 g, 2.60 mmol) were added. Dimethylformamide (8.0 mL) was added and the reaction mixture was cooled to 0° C. After adding triethylamine (1.2 mL, 8.6 mmol) the reaction mixture was stirred at ambient temperature for 28 h, and then partitioned between water and ethyl acetate. The organic layer was washed with saturated sodium chloride aqueous solution, dried over anhydrous sodium sulfate, and concentrated. Chromatography of the residue on silica gel with 45:55 ethyl acetate:hexanes eluent provided the title compound as a colorless solid. $^1$H NMR (500 MHz, acetone-d6): δ=7.92 (1H, br s), 7.41 (2H, dd), 7.08 (2H, dd), 5.64 (2H, m), 4.24 (2H, m), 3.22 (1H, dd), 2.72 (1H, dd), 2.50-2.40 (2H, m), 2.26-2.20 (2H, m), 2.12 (1H, m), 1.86 (1H, m). MS [ESI, (M–H)$^-$] m/z=303.1 amu.

Example 24

Synthesis of (1R/S,6R/S)-N-(cyanomethyl)-6-({[4-(methylsulfanyl)benzene]sulfonyl}-methyl)cyclohex-3-ene-1-carboxamide

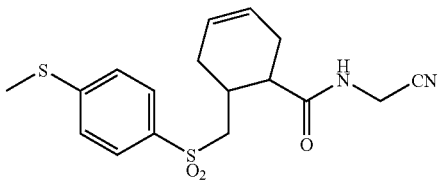

Step 1

(1R/S,6R/S)-N-(Cyanomethyl)-6-{[(4-fluorophenyl)thiolmethyl}cyclohex-3-ene-1-carboxamide (510 mg, 1.68 mmol) and sodium bicarbonate (3.00 g, 35.7 mmol) were suspended dissolved in a mixture of tetrahydrofuran (2.0 mL), 2.0 mL methanol and 2.0 mL water. The solution was cooled to 0° C. and (3.53 mmol) Oxone™ (2.17 g, 3.53 mmol) was added in portions over 5 min. After stirring at ambient temperature for 1 h, the reaction mixture was diluted with water and extracted with ethyl acetate. The combined organics were washed with saturated aqueous sodium chloride solution and dried over anhydrous sodium sulfate. Concentration in vacuo and chromatography of the residue on silica gel with 1:4 acetone:benzene as eluent afforded (1R/S,6R/S)-N-(cyanomethyl)-6-{[(4-fluorobenzene)sulfonyl]methyl}-cyclohex-3-ene-1-carboxamide as a colorless syrup.

Step 2

To (1R/S,6R/S)-N-(cyanomethyl)-6-{[(4-fluorobenzene)sulfonyl]methyl}cyclohex-3-ene-1-carboxamide (12 mg, 36 µmol), prepared by oxidation of title compound in Example 23 above, in a 10 mL round bottom flask was added dimethylformamide (1.0 mL) and sodium thiomethoxide (50 mg, 710 µmol). The reaction mixture was stirred at ambient temperature for 2.5 h and then partitioned between water and ethyl acetate. The organic layer was separated, washed with saturated sodium chloride aqueous solution, dried over anhydrous sodium sulfate, and concentrated. Chromatography of the residue on silica gel using a 1:4 mixture of acetone:benzene provided the title compound as a colorless foam.

$^1$H NMR (500 MHz, acetone-d6): δ=7.88 (1H, br s), 7.78 (2H, d), 7.46 (2H, d), 5.64 (2H, m), 4.19 (2H, m), 3.27 (1H, dd), 3.12 (1H, dd), 2.63 (1H, m), 2.58 (3H, s), 2.51 (1H, m), 2.35 (1H, m), 2.24-2.18 (2H, m), 2.06 (1H, overlapped m). MS [APCI, (M−H)$^-$] m/z=362.9 amu.

Example 25

Synthesis of (1R,2R)-N-(cyanomethyl)-2-({[4-(methylsulfanyl)benzene]-sulfonyl}methyl)-cyclohexanecarboxamide

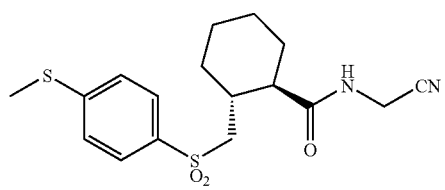

Step 1

(+)-trans-Cyclohexane-1,2-dicarboxylic anhydride (100 mg, 0.65 mmol) was weighed into a 10 mL round bottom flask and aminoacetonitrile hydrochloride (135 mg, 1.46 mmol) and 4-(dimethylamino)pyridine (7.5 mg, 61 µmol) added. After adding tetrahydrofuran (2.0 mL) and triethylamine (0.20 mL, 1.4 mmol), the reaction mixture was stirred at ambient temperature overnight. The reaction mixture was partitioned between 1 M aqueous hydrochloric acid (30 mL) and ethyl acetate (30 mL). The organic layer was separated, washed with saturated sodium chloride aqueous solution, dried over anhydrous sodium sulfate, and concentrated to give (1R,2R)-2-{[(cyanomethyl)amino]carbonyl}cyclohexanecarboxylic acid (as a colorless solid.

Step 2

(1R,2R)-2-{[(Cyanomethyl)amino]carbonyl}cyclohexanecarboxylic acid (97 mg, 0.46 mmol) in a 25 mL round bottom flask was fitted with a rubber septum and the flask was flushed with nitrogen. After adding tetrahydrofuran (1 mL), the reaction mixture was cooled to −78° C. and 4-methylmorpholine (51 µL, 0.47 mmol) and isobutyl chloroformate (51 µL, 0.46 mmol) were added. After 5 min, the reaction mixture was warmed quickly to 0° C. for 30 minutes. After recooling to −78° C., sodium borohydride (45 mg, 1.2 mmol) and methanol (1 mL) were added. After 5 min., the reaction mixture was allowed to warm to ambient temperature over 2 h. After quenching with 1 mL saturated aqueous ammonium chloride, the reaction mixture was partitioned between saturated aqueous sodium chloride solution and ethyl acetate. The organic layer was separated, washed with saturated sodium chloride aqueous solution, dried over anhydrous sodium sulfate, and concentrated. Toluene (5 mL) was added and stirring was carried out overnight. The solution was decanted and the residue was dried to give (1R,2R)-N-(cyanomethyl)-2-(hydroxymethyl)cyclohexanecarboxamide as a colorless powder.

Step 3

To (1R,2R)-N-(cyanomethyl)-2-(hydroxymethyl)cyclohexanecarboxamide (62 mg, 0.31 mmol) in a 4 mL sample vial was added 4-toluenesulfonyl chloride (73 mg, 0.38 mmol), 0.63 mL acetonitrile and pyridine (33 SL, 0.41 mmol). The reaction mixture was stirred at ambient temperature for 5 h after which the solvent was removed on a rotary evaporator. Chromatography of the residue on silica gel with 4:96 methanol:chloroform as eluent provided ((1R,2R)-2-{[(cyanomethyl)amino]carbonyl}cyclohexyl)methyl 4-methylbenzenesulfonate as a colorless, waxy solid.

Step 4

To ((1R,2R)-2-{[(cyanomethyl)amino]carbonyl}cyclohexyl)methyl 4-methylbenzene-sulfonate (35 mg, 0.10 mmol) in a 1 mL sample vial was added dimethylformamide (0.35 mL), potassium carbonate (70 mg, 0.51 mmol) and 4-fluorothiophenol (15 µL, 0.14 mmol) and the contents were stirred at ambient temperature for 20 h. The reaction mixture was partitioned between 2 mL ethyl acetate and 2 mL water. The organic layer was separated, washed with saturated sodium chloride aqueous solution, dried over anhydrous sodium sulfate, and concentrated. Chromatography of the residue on silica gel using a 2:3 mixture of ethyl acetate:hexanes provided (1R,2R)-N-(cyanomethyl)-2-{[(4-fluorophenyl)thiolmethyl]-cyclohexanecarboxamide as a colorless liquid. $^1$H NMR (500 MHz, acetone-d6): δ=7.81 (1H, br s), 7.39 (2H, dd), 7.07 (2H, t), 4.22 (2H, m), 3.11 (1H, dd), 2.60 (1H, dd), 2.20-2.08 (overlapped) (2H, m), 1.90 (1H, m), 1.82 (1H, m), 1.79-1.68 (2H, m), 1.43 (1H, m), 1.30-1.18 (2H, m), 1.03 (1H, m). MS [ESI, (M−H)$^-$] m/z=305.2 amu.

Step 5

To a solution of (1R,2R)-N-(cyanomethyl)-2-{[(4-fluorophenyl)thiolmethyl}-cyclohexanecarboxamide (20 mg, 64 [mol) in tetrahydrofuran (0.50 mL), methanol (0.50 mL) and water (0.50 mL) was added sodium bicarbonate (100 mg, 1.2 mmol). Oxone™ (100 mg, 0.16 mmol) was added and the reaction mixture was stirred at ambient temperature for 19 h. The reaction mixture was partitioned between 10 mL water and 10 mL ethyl acetate. The organic layer was separated and washed with saturated aqueous sodium chloride solution, dried over anhydrous sodium sulfate, filtered and concentrated to give (1R,2R)-N-(cyanomethyl)-2-{[(4-fluorobenzene)sulfonyl]methyl}-cyclohexanecarboxamide as a colorless, waxy solid.

Step 6

To a solution of (1R,2R)-N-(cyanomethyl)-2-{[(4-fluorobenzene)sulfonyl]methyl}-cyclohexanecarboxamide (22 mg, 64 Kmol) in 1.5 mL dimethylformamide was added sodium thiomethoxide (50 mg, 710 mmol) and the reaction mixture was stirred at ambient temperature for 19 h. The reaction mixture was partitioned between 30 mL water and 30 mL ethyl acetate. The organic layer was separated and washed with 30 mL saturated aqueous sodium chloride solution, dried over anhydrous sodium sulfate and concentrated. Chromatography of the residue on silica gel using 15:85 acetone:benzene as eluent provided the title compound.

Example 26

Synthesis of (1R/S,2R/S,3R/S,6S/R)-N-(cyanomethyl)-3-(([4-(methylsulfanyl)benzene]sulfonyl}-methyl)bicyclo[4.1.0]heptane-2-carboxamide

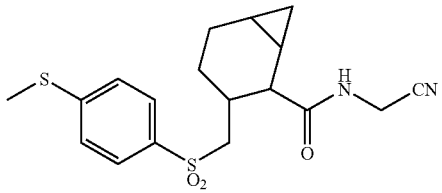

Step 1

To ethyl β-formylacrylate (20.6 g, 163.5 mmol) (see M. Schmitt, J. J. Bourguignon, C. G. Wermuth, *Tetrahedron Lett.*, 31 (15), p. 2145-2148 (1990)) and acrolein (16.4, 245.0 mmol) was added hydroquinone (180 mg, 1.64 mmol) and the reaction mixture was heated neat to 95° C. for 12 h in a sealed tube. High vacuum distillation (75-80° C., 0.2-0.3 mm Hg) yielded predominantly ethyl(1R/S,6S/R)-6-formyl-cyclohex-2-ene-1-carboxylate which was dissolved in benzene (100 mL) and equilibrated with basic alumina (50 g) under an atmosphere of dry nitrogen over 6 days to afford ethyl(1R/S,6R/S)-6-formylcyclohex-2-ene-1-carboxylate as major product (ratio>5:1).

Step 2

To ethyl(1R/S,6R/S)-6-formylcyclohex-2-ene-1-carboxylate (8.05 g, 44.23 mmol) in methanol (100 mL) at 0° C. was added NaBH$_4$ (3.34 g, 88.46 mmol) portionwise and the reaction mixture was stirred for 4 h. Water was added, and the product extracted with ethyl acetate and dried over anhydrous sodium sulfate. The solvent was removed in vacuo and the product was purified by flash chromatography over silica gel (ethyl acetate/hexanes, 3/7) to afford both the cyclized product (3αR/S,7αR/S)-3α,4,5,7α-tetrahydro-2-benzofuran-1-(3H)-one (375 mg) and the desired uncyclized product ethyl(1R/S,6R/S)-6-(hydroxymethyl)cyclohex-2-ene-1-carboxylate.

Step 3

To 1,2-dichloroethane (100 mL) at 0° C. and under a dry nitrogen atmosphere was added Et$_2$Zn (neat, 5.2 mL, 50.0 mmol) dropwise followed by chloroiodomethane (7.72 mL, 106.0 mmol) and the reaction mixture was stirred 5 min. (1R/S,6R/S)-6-(Hydroxymethyl)cyclohex-2-ene-1-carboxylate (3.67 g, 20.0 mmol) was then added and the reaction mixture was stirred 1 h at 0° C. followed by overnight stirring at room temperature. The reaction mixture was carefully quenched with water, the product extracted with ether, and dried on anhydrous sodium sulfate. The solvent was removed in vacuo and the product was purified by flash chromatography over silica gel (ethyl acetate/hexanes, 2/8) to afford the desired product (3αR/S,5αS/R,6αR/S,6βR/S)-octahydro-1H-cyclopropa[3,4]benzo[1,2-c]furan-1-one along with some of the uncyclized product ethyl(2R/S,3R/S)-3-(hydroxymethyl)bicyclo[4.1.0]heptane-2-carboxylate.

Step 4

To a suspension of NaH (165 mg, 4.05 mmol) in dry dimethylformamide (10 mL) under an atmosphere of dry nitrogen was added 4-fluorothiophenol (430 μL, 4.05 mmol) dropwise and the reaction was stirred for 15 min. A solution of (3αR/S,5αS/R,6αR/S,6βR/S)-octahydro-1H-cyclopropa[3,4]benzo[1,2-c]furan-1-one (202 mg, 1.35 mmol) in dry dimethylformamide (2 mL) was added to the reaction mixture and was heated to 110° C. for 4.5 h. The reaction mixture was cooled to room temperature and quenched with aqueous 10% HCl, the product extracted with ethyl acetate, and dried on anhydrous sodium sulfate. The solvent was removed in vacuo and the product was purified by flash chromatography over silica gel (ethyl acetate/hexanes, 2/8+ 0.5% AcOH) to afford the desired product (1R/S,2R/S,3R/S,6S/R)-3-{[(4-fluorophenyl)-sulfanyl]methyl}bicyclo[4.1.0]heptane-2-carboxylic acid.

Step 5

To (1R/S,2R/S,3R/S,6S/R)-3-{[(4-fluorophenyl)sulfanyl]methyl}bicyclo[4.1.0]heptane-2-carboxylic acid (310 mg, 1.12 mmol), PyBOP (640 mg, 1.23 mmol), and aminoacetonitrile hydrochloride (228 mg, 2.46 mmol) was added dry dimethylformamide (10 mL) under an atmosphere of dry nitrogen followed by triethylamine (550 μL, 3.92 mmol) and the reaction mixture was stirred for 4.5 h at room temperature. The reaction mixture was poured into aqueous saturated sodium hydrogen carbonate, extracted with ether, and dried over anhydrous sodium sulfate. The solvent was concentrated in vacuo and the crude product was purified by flash chromatography over silica gel (ethyl acetate/hexanes, 4/6) to yield (1R/S,2R/S,3R/S,6S/R)-N-(cyanomethyl)-3-{[(4-fluorophenyl)sulfanyl]methyl}-bicyclo[4.1.0]heptane-2-carboxamide. $^1$H NMR (400 MHz, acetone-d6): δ=7.85 (1H, br s), 7.42-7.35 (2H, m), 7.11-7.05 (2H, m), 4.31-4.19 (2H, m), 2.98 (1H, dd), 2.83 (1H, m), 2.72 (1H, dd), 1.94 (1H, m), 1.85-1.75 (2H, m), 1.54 (1H, m), 1.27-1.16 (2H, m), 0.98 (1H, m), 0.63 (1H, dt). MS [ESI, (M−H)$^-$] m/z=317.0 amu.

Step 6

To (1R/S,2R/S,3R/S,6S/R)-N-(cyanomethyl)-3-{[(4-fluorophenyl)sulfanyl]methyl}-bicyclo[4.1.0]heptane-2-carboxamide (235 mg, 0.74 mmol) in tetrahydrofuran/methanol/water (1/1/1, 5 mL) was added sodium hydrogen carbonate (1.245 g, 14.8 mmol) followed by Oxone™ (1.14 g, 1.85 mmol) and the reaction mixture was stirred for 6 h. Water was added, the product extracted with ethyl acetate, and dried on anhydrous sodium sulfate. The solvent was removed in vacuo and the crude product was purified by flash chromatography over silica gel (ethyl acetate/hexanes, 1/1) to afford (1R/S,2R/S,3R/S,6S/R)-N-(cyanomethyl)-3-{[(4-fluorobenzene)-sulfonyl]methyl}bicyclo[4.1.0]heptane-2-carboxamide. $^1$H NMR (400 MHz, acetone-d6): δ=8.01-7.96 (2H, m), 7.86 (1H, br s), 7.45-7.39 (2H, m), 4.24-4.14 (2H, m), 3.30-3.19 (2H, m), 2.67 (1H, dd), 2.16 (1H, m), 2.05 (1H, m), 1.88 (1H, dt), 1.59 (1H, m), 1.24-1.14 (2H, m), 0.97 (1H, m), 0.67 (1H, dt), 0.02 (1H, t). MS [ESI, (M+H)$^+$] m/z=351.0 amu.

Step 7

To (1R/S,2R/S,3R/S,6S/R)-N-(cyanomethyl)-3-{[(4-fluorobenzene)sulfonyl]methyl}-bicyclo[4.1.0]heptane-2-carboxamide (160 mg, 0.457 mmol) in dry dimethylformamide (5 mL) under an atmosphere of dry nitrogen was added NaSMe (640 mg, 9.14 mmol) and the reaction was stirred at room temperature for 3.5 h. Water was added, the product extracted with ethyl acetate, and dried on anhydrous sodium sulfate. The solvent was removed in vacuo and the crude product was purified by flash chromatography over silica gel (ethyl acetate/hexanes, 55/45) to afford the title compound. $^1$H NMR (400 MHz, acetone-d6): δ=7.84 (1H, br s), 7.78 (2H, d), 7.47 (2H, d), 4.24-4.13 (2H, m), 3.19 (2H, d), 2.67 (1H, dd), 2.58 (3H, s), 2.15 (1H, m), 2.05 (1H, m), 1.87 (1H, m), 1.58 (1H,m), 1.23-1.13 (2H, m), 0.96 (1H, m), 0.66 (1H, m), 0.01 (1H, dd). MS [ESI, (M+H)$^+$] m/z=379.1 amu.

Example 27

Synthesis of (1R/S,3R/S,6R/S)-N-(cyanomethyl)-5-methyl-2-({[4-(methylsulfanyl)benzene]sulfonyl}methyl)cyclohexanecarboxamide and (1R/S,3S/R,6R/S)-N-(cyanomethyl)-5-methyl-2-({[4-(methylsulfanyl)benzene]sulfonyl}methyl)cyclohexanecarboxamide

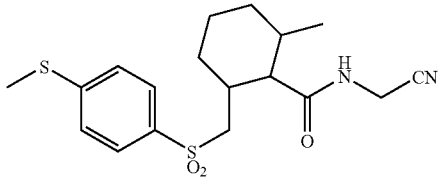

Step 1

To malonic acid (250 g, 2.4 mol) in pyridine (350 mL) at 80° C. was added, via a dropping funnel, methacrolein (125 mL, 3 mol) over 10 min. The reaction mixture was stirred at 80° C. for 15 min., followed by the addition of a further portion of methacrolein (125 mL, 3 mol). The reaction mixture was heated at 80° C. for a further 20 min and then cooled to room temperature and added to ice. The reaction mixture was acidified with concentrated HCl/water (1:1, ~500 mL) and extracted with dichloromethane. The combined organic extracts were washed with water and dried (anhydrous sodium sulfate). Hydroquinone (1 g) was added to prevent polymerization and the mixture was concentrated in vacuo. To the crude (2E)-4-methylpenta-2,4-dienoic acid thus obtained was added ethanol (500 mL) and concentrated H$_2$SO$_4$ (10 mL). The reaction mixture was refluxed overnight, poured into water and extracted with ether. Ethyl(2E)-4-methylpenta-2,4-dienoate was distilled (65° C./15 mm Hg) from the solvent mixture as a colorless oil.

Step 2

A mixture of ethyl(2E)-4-methylpenta-2,4-dienoate (8.5 g, 60.6 mmol), acrolein (5.1 g, 91 mmol) and hydroquinone (67 mg, 0.6 mmol) was heated to 95-100° C. for 24 h. The mainly cis-ethyl 6-formyl-3-methylcyclohex-2-ene-1-carboxylate was isolated by distillation (60-80° C./0.5 mm Hg) and then equilibrated with freshly activated basic alumina (~2 grams of basic alumina per gram of cis-ethyl 6-formyl-3-methylcyclohex-2-ene-1-carboxylate) in benzene as solvent (~6 mL benzene per gram of cis-ethyl 6-formyl-3-methylcyclohex-2-ene-1-carboxylate). After stirring at room temperature for 6 days, the equilibration mixture was filtered through Celite™ and the filter cake was washed with ethyl acetate. (1R/S,6R/S)-Ethyl 6-formyl-3-methylcyclohex-2-ene-1-carboxylate was then purified by distillation (65° C./15 mm Hg) as a colorless oil.

Step 3

To ethyl(1R/S,6R/S)-6-formyl-3-methylcyclohex-2-ene-1-carboxylate (516 mg, 2.6 mmol) in methanol (13 mL) at 0° C. was added NaBH$_4$ (199 mg, 5.3 mmol) and the reaction mixture was stirred for 2 h. Water was added, the product extracted with ethyl acetate, and dried over anhydrous sodium sulfate. The solvent was removed in vacuo and the product was purified by flash chromatography over silica gel (ethyl acetate/hexanes, 20/80 to 40/60) to afford ethyl (1R/S,6R/S)-6-(hydroxymethyl)-3-methylcyclohex-2-ene-1-carboxylate.

Step 4

To a solution of ethyl(1R/S,6R/S)-6-(hydroxymethyl)-3-methylcyclohex-2-ene-1-carboxylate (166 mg, 0.84 mmol) and 10% palladium on carbon (17 mg) in ethyl acetate (8 mL) was added an atmosphere of hydrogen. The suspension was stirred at room temperature overnight and then filtered through Celite™. The filter cake was washed with ethyl acetate and the combined filtrates were concentrated in vacuo to yield a residue that was still contaminated with starting material. This residue was subjected to the same hydrogenation conditions as described above except 34 mg of 10% Pd/C was used. After stirring under a hydrogen atmosphere for 15 h, the hydrogen was removed and the suspension was flushed with nitrogen. A further 17 mg of 10% Pd/C was added and subjected to a hydrogen atmosphere overnight. The suspension was then filtered through Celite™ and the filter cake was washed with ethyl acetate. The combined filtrates were concentrated in vacuo to yield a 1:1 diastereomeric mixture of (1R/S,3R/S,6R/S)-ethyl 2-(hydroxymethyl)-5-methylcyclohexanecarboxylate and (1R/S,3S/R,6R/S)-ethyl 2-(hydroxymethyl)-5-methylcyclohexanecarboxylate.

Step 5

To a cold (0° C.) solution of triphenylphosphine (260 mg, 1.0 mmol) in dimethylformamide (1 mL) was added diisopropyl azodicarboxylate (180 μL, 0.9 mmol) and the reaction mixture was stirred at 0° C. for 10 min. A mixture of (1R/S,3R/S,6R/S)-ethyl 2-(hydroxymethyl)-5-methylcyclohexanecarboxylate and (1R/S,3S/R,6R/S)-ethyl 2-(hydroxymethyl)-5-methylcyclohexanecarboxylate (1:1 mixture, 160 mg, 0.8 mmol) and 4-fluorobenzenethiol (100 μL, 0.9 mmol) in dimethylformamide (1 mL) was added to the diisopropyl azodicarboxylate/triphenylphosphine mixture. The reaction mixture was warmed to room temperature and stirred for 3 h. Ether and brine were added and the aqueous layer was extracted with ether. The combined organic extracts were concentrated in vacuo and the residue was purified by flash chromatography over silica gel (ether/hexanes, 5/95) to afford the product (1R/S,3R/S,6R/S)-ethyl 2-{[(4-fluorophenyl)sulfanyl]methyl}-5-methylcyclohexanecarboxylate and (1R/S,3S/R,6R/S)-ethyl 2-{[(4-fluorophenyl)sulfanyl]methyl}-5-methylcyclohexane-carboxylate as a 1:1 mixture of diastereomers.

Step 6

A solution of (1R/S,3R/S,6R/S)-ethyl 2-{[(4-fluorophenyl)sulfanyl]methyl}-5-methyl-cyclohexanecarboxylate and (1R/S,3S/R,6R/S)-ethyl 2-{[(4-fluorophenyl)sulfanyl]-methyl}-5-methylcyclohexanecarboxylate (1:1 mixture, 54 mg, 0.17 mmol) in a mixture of aqueous LiOH (2 M, 1.7 mL, 3.4 mmol), DME (1 mL) and ethanol (0.3 mL) was heated at 70°

C. for 7 h. The solution was cooled to room temperature, acidified with aqueous 2 M HCl (0.5 mL) and extracted with ethyl acetate. The organic extracts were concentrated in vacuo to yield (1R/S,3R/S,6R/S)-2-{[(4-fluorophenyl)sulfanyl]methyl}-5-methylcyclohexanecarboxylic acid and (1R/S,3S/R,6R/S)-2-{[(4-fluorophenyl)sulfanyl]methyl}-5-methylcyclohexanecarboxylic acid as a 1:1 mixture of diastereomers.

Step 7

To (1R/S,3R/S,6R/S)-2-{[(4-fluorophenyl)sulfanyl]methyl}-5-methylcyclohexanecarboxylic acid and (1R/S,3S/R,6R/S)-2-{[(4-fluorophenyl)sulfanyl]methyl}-5-methylcyclohexanecarboxylic acid (1:1 mixture, 52 mg, 0.18 mmol), PyBOP (144 mg, 0.28 mmol), and aminoacetonitrile hydrochloride (34 mg, 0.37 mmol) was added dry dimethylformamide (2 mL) under an atmosphere of dry nitrogen followed by triethylamine (103 µL, 0.74 mmol) and the reaction mixture was stirred for 5 h at room temperature. The reaction mixture was poured into aqueous saturated sodium hydrogen carbonate, extracted with ethyl acetate, and dried over anhydrous sodium sulfate. The solvent was concentrated in vacuo and the crude product was purified by flash chromatography over silica gel (ethyl acetate/hexanes, 30/70 to 50/50) to yield (1R/S,3R/S,6R/S)-N-(cyanomethyl)-2-{[(4-fluorophenyl)sulfanyl]-methyl}-5-methylcyclohexanecarboxamide and (1R/S,3S/R,6R/S)-N-(cyanomethyl)-2-{[(4-fluorophenyl)sulfanyl]methyl}-5-methylcyclohexanecarboxamide as a 1:1 mixture of diastereomers.

Step 8

To (1R/S,3R/S,6R/S)-N-(cyanomethyl)-2-{[(4-fluorophenyl)sulfanyl]methyl}-5-methylcyclohexanecarboxamide and (1R/S,3S/R,6R/S)-N-(cyanomethyl)-2-{[(4-fluorophenyl)sulfanyl]methyl}-5-methylcyclohexanecarboxamide (1:1 mixture, 40 mg, 0.12 mmol) in tetrahydrofuran/methanol/water (1/1/1, 3 mL) was added sodium hydrogen carbonate (199 mg, 2.4 mmol) followed by Oxone™ (192 mg, 0.3 mmol) and the reaction mixture was stirred for 1.5 h. Water was added, the product extracted with ethyl acetate, and dried over anhydrous sodium sulfate. The solvent was removed in vacuo and the crude product was purified by flash chromatography over silica gel (ethyl acetate/hexanes, 50/50 to 70/30) to afford (1R/S,3R/S,6R/S)-N-(cyanomethyl)-2-{[(4-fluorobenzene)sulfonyl]-methyl}-5-methylcyclohexanecarboxamide and (1R/S,3S/R,6R/S)-N-(cyanomethyl)-2-{[(4-fluorobenzene)sulfonyl]methyl 1-5-methylcyclohexanecarboxamide as a 1:1 mixture of diastereomers.

Step 9

To (1R/S,3R/S,6R/S)-N-(cyanomethyl)-2-{[(4-fluorobenzene)sulfonyl]methyl}-5-methyl-cyclohexanecarboxamide and (1R/S,3S/R,6R/S)-N-(cyanomethyl)-2-([(4-fluorobenzene)-sulfonyl]methyl}-5-methylcyclohexanecarboxamide (1:1 mixture, 21 mg, 0.06 mmol) in dry dimethylformamide (3 mL) under an atmosphere of dry nitrogen was added NaSMe (99 mg, 1.4 mmol) and the reaction was stirred at room temperature overnight. Water was added, the product extracted with ethyl acetate (3×), and dried over anhydrous sodium sulfate. The solvent was removed in vacuo and the crude product was purified by flash chromatography over silica gel (acetone/benzene, 20/80) to afford the desired product (1R/S,3R/S,6R/S)-N-(cyanomethyl)-5-methyl-2-({[4-(methylsulfanyl)benzene]-sulfonyl}methyl)cyclohexanecarboxamide and (1R/S,3S/R,6R/S)-N-(cyanomethyl)-5-methyl-2-({[4-(methylsulfanyl)-benzene]sulfonyl}methyl)-cyclohexanecarboxamide as a 1:1 mixture of diastereomers. $^1$H NMR (500 MHz, acetone-d6): δ=7.74-7.78 (3H, m), 7.45 (2H, d), 4.15 (2H, d), 3.11-3.18 (1H, m), 2.99 (1H, dd), 2.58 (3H, s), 2.30-2.35 (1H, m), 2.21-2.27 (1H, m), 1.66-1.78 (2H, m), 1.06-1.52 (4H, m), 0.88-0.96 (1H, m), 0.86 (3H, d). MS [ESI, (M−H)-] m/z=379.2 amu.

Example 28

Synthesis of trans-N-cyanomethyl-2-[4-(2-phenylethylsulfanyl)-benzenesulfonylmethyl]-cyclohexanecarboxamide

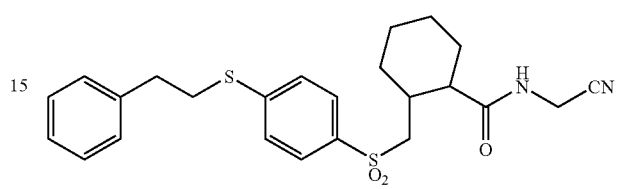

A mixture of trans-N-cyanomethyl-2-(4-methylsulfanyl-benzenesulfonylmethyl)-cyclohexanecarboxamide (0.1 g, 0.298 mmol), phenethyl mercaptan (0.103 mL, 0.764 mmol) and cesium carbonate (0.25 g, 0.764 mmol) was dissolved in dimethylformamide (1.5 mL) and heated at 100° C. for 4 h. The reaction mixture was diluted with ethyl acetate (30 mL), filtered through Celite, evaporated to dryness, and purified on a short plug of silica gel (2040% ethyl acetate/CHCl$_3$), yielding the desired product. NMR (DMSO-d6): 1.1 (3H, m); 1.3 (1H, m) 1.6-1.7 (3H, m); 2.03 (2H, m); 2.16 (1H, d): 2.92 (3H, m); 3.15 (1H, dd); 3.36 (2H, m); 4.03 (2H, d); 7.1 (1H, d); 7.25 (4H, m); 7.47 (2H, d); 7.68 (2H, d); 8.56 (1H, t). MS [ESI, (M+Na)+] m/z=479 amu.

Example 29

Synthesis of trans-N-cyanomethyl-2-[4-(tert-butoxycarbonylaminoethylsulfanyl)-benzenesulfonylmethyl]cyclohexanecarboxamide

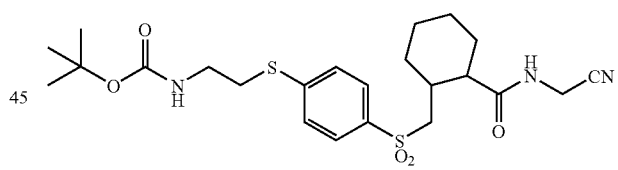

To a solution of trans-N-cyanomethyl-2-(4-methylsulfanylbenzenesulfonylmethyl)-cyclohexanecarboxamide (0.37 g, 1.09 mmol) in acetonitrile (20 mL) were added Boc-aminoethanethiol (0.369 mL, 2.18 mmol) and cesium carbonate (0.713 g, 2.18 mmol). The reaction mixture was heated at reflux for 12 h, and cooled to room temperature. Ethyl acetate (100 mL) was added. The solution was filtered through Celite, concentrated, and purified on a short plug of silica gel (20-50% ethyl acetate/dichloromethane) to yield the desired product. MS [ESI, (M+Na)+] m/z=518 amu.

Proceeding as described above but substituting Boc-aminoethanethiol with 2-pyridylethanethiol provided trans-N-cyanomethyl-2-[4-(pyridin-2-ylethylsulfanyl)-benzenesulfonylmethyl]cyclohexanecarboxamide. $^1$H NMR (DMSO-d6): 1.1 (3H, m); 1.32 (1H, m); 1.63 (3H, m); 2.01 (2H, m); 2.12 (1H, dd); 2.92 (1H, d); 3.09 (2H, t); 3.18 (1H, dd); 3.47 (2H, t); 4.06 (2H, d); 7.21 (1H, dd); 7.3 (1H, d); 7.49 (2H, d); 7.68 (2H, d); 7.69 (1H, d); 8.5 (1H, d); 8.55 (1H, t).

Example 30

Synthesis of trans-N-cyanomethyl-2-[4-(aminoethylsulfanyl)-benzenesulfonylmethyl]-cyclohexanecarboxamide mesylate salt

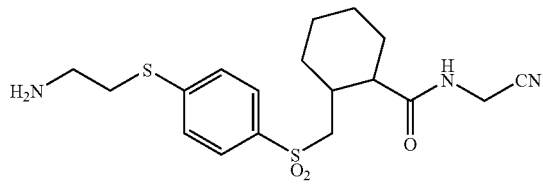

To a solution of trans-N-cyanomethyl-2-[4-(tert-butoxycarbonylaminoethylsulfanyl)-benzenesulfonylmethyl]cyclohexanecarboxamide (0.35 g, 0.706 mmol) in tetrahydrofuran (2 mL) at room temperature was added dry methanesulfonic acid (0.183 mL, 2.82 mmol). The reaction mixture was stirred overnight at room temperature. Ether (200 mL) was added. The supernatant was decanted. The residue was triturated twice with ether (50 mL each) and was then precipitated from methanol/ether, giving the title compound as its mesylate salt. MS [ESI, (M−H)⁻] m/z=394 amu.

Example 31

Synthesis of trans-N-cyanomethyl-2-[4-(2-(2-chloropyridin-3-yl)aminoethylsulfanyl)-benzenesulfonylmethyl]cyclohexanecarboxamide mesylate salt

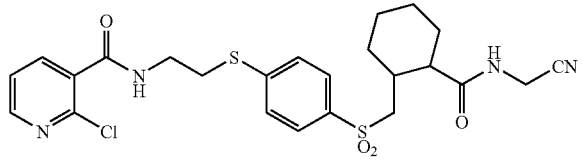

To a mixture of 2-chloronicotinic acid (20 mg, 0.112 mmol), and trans-N-cyanomethyl-2-[4-(aminoethylsulfanyl) benzenesulfonylmethyl]cyclohexanecarboxamide (50 mg, 0.102 mmol) in tetrahydrofuran (1 mL) was added diisopropylethylamine (71 μL, 0.407 mmol). The reaction mixture was stirred overnight at room temperature, then purified directly on a short plug of silica gel (0-10% methanol/dichloromethane) to give the title compound. MS [ESI, (M+H)+] m/z 535 amu, MS [ESI, (M+Na)⁺] m/z=557 amu.

Example 32

Synthesis of trans-N-cyanomethyl-2-[4-(2-pyridin-4-ylaminoethylsulfanyl)-benzenesulfonyl-methyl] cyclohexanecarboxamide mesylate salt

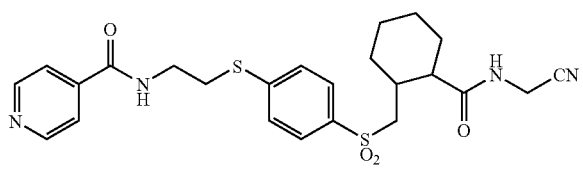

To a mixture of isonicotinoyl hydrochloride (20 mg, 0.112 mmol) and trans-N-cyanomethyl-2-[4-(aminoethylsulfanyl) benzenesulfonylmethyl]cyclohexanecarboxamide (50 mg, 0.102 mmol) in tetrahydrofuran (1 mL) was added diisopropylethylamine (71 μL, 0.407 mmol). The reaction mixture was stirred overnight at room temperature, then purified directly on a short plug of silica gel (5-10% methanol/dichloromethane) to give the title compound. MS [ESI, (M+H)⁺] m/z=501 amu.

Example 33

Synthesis of trans-N-cyanomethyl-2-[3-fluoro-4-(2-dimethylaminosulfonylaminoethylsulfanyl)-benzenesulfonylmethyl]cyclohexanecarboxamide mesylate salt

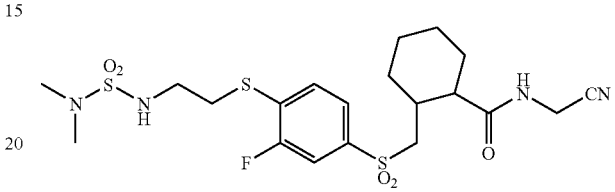

Step 1

In a 3-necked flask charged with fine magnesium turnings (1.39 g, 56.99 g-atom) in dry tetrahydrofuran (50 mL), and equipped with an addition funnel, condenser, and nitrogen inlet was added, dropwise, a solution of 3,4-difluorobromobenzene (10.0 g, 51.8 mmol) in tetrahydrofuran (50 mL). The reaction mixture was heated to boiling for 30 min, during which time the metal dissolved. The solution was then cooled to −10° C., whereupon sulfur (1.83 g, 56.99 g-atom) was added over 10 min. The reaction mixture was stirred for 2 h at room temperature. Ice (50 g) was added, followed by concentrated HCl (10 mL) and the product, 3,4-difluorothiophenol, was extracted with ether (200 mL), dried over anhydrous magnesium sulfate, filtered, and concentrated, the product being used directly in the next step. (see Terao, J. et al., Synthesis 1987, 149-153).

Step 2

To a solution of N-cyanomethyl 2-bromomethylcyclohexanecarboxamide (3.0 g, 11.58 mmol) in acetone (100 mL) at room temperature were added, in two portions, cesium carbonate (5.77 g, 17.5 mmol) and the crude 3,4-difluorothiophenol (2.69 g, 18.4 mmol). After 16 h, ethyl acetate (100 mL) was added. The solution was washed with 1M HCl (40 mL), brine (20 mL), evaporated, and purified on a short plug of silica gel (30% ethyl acetate/hexane to elute non-polar impurities, then 20-30% ethyl acetate/dichloromethane to give N-cyanomethyl 2-(3,4-difluorophenylsulfanylmethyl)-cyclohexanecarboxamide.

Step 3

N-cyanomethyl 2-(3,4-difluorophenylsulfanylmethyl)-cyclohexanecarboxamide was then dissolved in methanol (50 mL), to which a solution of Oxone® (15 g, 24.41 mmol) in water (50 mL) was added. The reaction mixture was stirred at room temperature overnight. The suspension was filtered, the solids were washed with methanol, the combined filtrates were concentrated to remove methanol, and ethyl acetate (100 mL) was added. The organic phase was washed with saturated aqueous sodium hydrogen carbonate (100 mL), brine (100 mL), dried over anhydrous magnesium sulfate, filtered, evaporated to dryness, and the residue was crystallized from dichloromethane/ether/hexane, giving N-cyanomethyl 2-(3,4-difluoro-benzenesulfonylmethyl)-cyclohexanecarboxamide. $^1$H NMR (DMSO-d6): 1.06 (3H, m); 1.15 (1H, q); 1.62 (3H, m); 2.00 (2H, m); 2.14 (1H, d); 2.96 (1H, dd) 3.23 (1H, dd); 4.02 (2H, d); 7.72 (2H, m); 7.93 (1H, m); 8.58 (1H, t). MS [ESI, (M+Na)$^+$] m/z=379 amu.

Step 4

To N-cyanomethyl 2-(3,4-difluorobenzenesulfonylmethyl)-cyclohexanecarboxamide (0.54 g, 1.49 mmol) dissolved in acetonitrile (10 mL) was added Boc-aminoethanethiol (0.251 mL, 1.49 mmol) and cesium carbonate (0.485 g, 1.49 mmol). The reaction mixture was heated at reflux for 3 h, cooled, concentrated to dryness, and purified on a short plug of silica gel, using 0-50% ethyl acetate/dichloromethane as eluent to give (2-{4-[2-(cyanomethyl-carbamoyl)-cyclohexylmethylsulfanyl]-2-fluoro-phenylsulfanyl}-ethyl)-carbamic acid tert-butyl ester.

Step 5

(2-{4-[2-(Cyanomethylcarbamoyl)-cyclohexylmethylsulfanyl]-2-fluorophenylsulfanyl}-ethyl)-carbamic acid tert-butyl ester was dissolved in tetrahydrofuran (3 mL) and methanesulfonic acid (0.428 g, 6.6 mmol) was added. The reaction mixture was stirred at room temperature overnight, whereupon ether (100 mL) was added. The supernatant was discarded. The residue was triturated three times with ether (50 mL) then 10% tetrahydrofuran/ether, resulting in a white solid, N-cyanomethyl 2-[4-(2-aminoethylsulfanyl)-3-fluoro-phenylsulfanylmethyl]-cyclohexanecarboxamide mesylate, which was isolated by filtration in near quantitative mass recovery, with a small amount of t-butyl amide present as an inseparable impurity, resulting from addition of tert-butanol across the nitrile group under the acidic Boc-cleavage conditions. MS [ESI, (M+H)$^+$] m/z=412 amu.

Step 6

N-Cyanomethyl 2-[4-(2-aminoethylsulfanyl)-3-fluorophenylsulfanylmethyl]-cyclohexanecarboxamide mesylate (0.1 g, 0.196 mmol) was suspended in dichloromethane (2 mL) at room temperature. Dimethylsulfamoyl chloride (0.025 mL, 0.235 mmol) and diisopropylethylamine (0.102 mL, 0.588 mmol) were added. The mixture was stirred at room temperature overnight. The solution was directly purified by flash chromatography (5% methanol/dichloromethane) to give the desired product. MS [ESI, (M+Na)$^+$] m/z=543 amu.

Example 34

Synthesis of trans-N-cyanomethyl-2-{4-[3-fluoro-2-(4-pyridin-2-yl)ethylsulfanyl]-benzenesulfonylmethyl cyclohexanecarboxamide mesylate salt

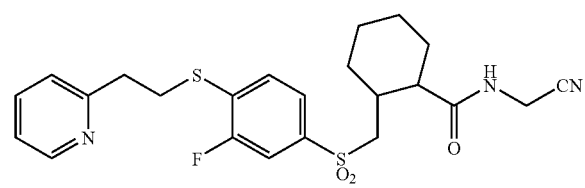

The title compound was synthesized from N-cyanomethyl 2-(3,4-difluorophenyl-sulfanylmethyl)-cyclohexanecarboxamide, described above, and 2-pyridylethanethiol according to the method described in Example 29 above. $^1$H NMR (DMSO-d6): 1.1 (3H, m); 1.35 (1H, q); 1.63 (3H, m); 2.0 (2H, m); 2.16 (1H, d): 2.96 (1H, d); 3.1 (2H, t); 3.27 (1H, dd); 3.52 (2H, t); 4.04 (2H, d); 7.21 (1H, d); 7.3 (1H, d); 7.56-7.68 (4H, m); 8.42 (1H, d); 8.57 (1H, t).

Example 35

Synthesis of trans-2-(4-pyridin-2-ylethylsulfanyl)cyclohexane carboxylic acid (1-cyanocyclopropyl amide

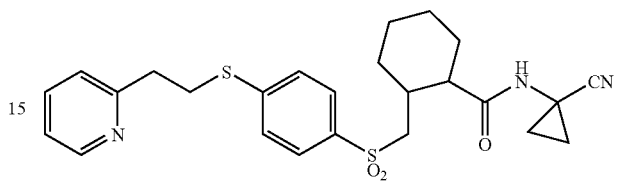

Step 1

To a mixture of trans-hexahydroisobenzofuran-1,3-dione (2.62 g, 17.01 mmol) and 1-amino-cyclopropanecarbonitrile hydrochloride (2.00 g, 17.01 mmol, (see O'Donnell, M. J., et al., Synthesis, 1984, 127-128) in dichloromethane (100 mL) at −10° C. was added triethylamine (5.22 mL, 37.43 mmol). The reaction mixture was allowed to warm to room temperature overnight. The solvent was evaporated and the residue was dissolved in tetrahydrofuran (80 mL), and cooled to −10° C. Isobutyl chloroformate (2.21 mL), 17.01 mmol) was added. After 15 min., the solution was filtered (20 mL tetrahydrofuran wash) and the filtrates were poured slowly into a solution of NaBH$_4$ (1.28 g, 34.02 mmol) in water (100 mL) at 0° C. The reaction mixture was stirred for 1 h and then saturated aqueous sodium hydrogen carbonate (100 mL) and ethyl acetate (150 mL) were added. The reaction mixture was stirred vigorously for 1 h. The organic phase was separated, washed with brine, the aqueous phases were combined, extracted with ethyl acetate, then the combined organics were dried over anhydrous magnesium sulfate, filtered, and concentrated. The residue was recrystallized from ethyl acetate/hexane to give (1-cyanocyclopropyl)-2-hydroxymethyl-cyclohexane-carboxamide.

Step 2

(1-Cyanocyclopropyl)-2-hydroxymethyl-cyclohexanecarboxamide was dissolved, along with triphenylphosphine (2.77 g, 10.58 mmol) in tetrahydrofuran (100 mL) (Note—heating was required to effect dissolution). The reaction mixture was cooled carefully in an ice/water bath, ensuring the solution remained homogeneous. N-bromosuccinimide (1.88 g, 10.58 mmol) was added in small portions. Once a clear solution had formed, the cooling bath was removed, and the reaction mixture was permitted to stir overnight. The solvent was evaporated and the residue was purified on a short plug of silica gel (30-60% ethyl acetate/hexane) to give (1-cyanocyclopropyl)-2-bromomethylcyclohexanecarboxamide. MS [ESI, (M+H)$^+$] m/z=285, 287.

Step 3

(1-Cyanocyclopropyl)-2-bromomethylcyclohexanecarboxamide was converted to (1-cyanocyclopropyl)-2-(4-fluoro-phenylsulfanylmethyl)-cyclohexanecarboxamide as a result of reaction with 4-fluorothiophenol under the reaction conditions described in Example 33 above and converted to (1-cyano-cyclopropyl)-2-(4-fluorobenzenesulfonylmethyl)-cyclohexanecarboxamide using Oxone® as described above.

Step 4

(1-Cyanocyclopropyl)-2-(4-fluorobenzenesulfonylmethyl)cyclohexanecarboxamide was converted to the title compound by reaction with 2-pyridineethanethiol in acetonitrile, according to the method in Example 29 above. NMR (¹H, DMSO-d6): 0.83 (2H, t); 1.03-1.41 (6H, m*); 1.6 (3H, m); 1.93 (2H, m); 2.1 (1H, d); 2.9 (1H, d); 3.08 (2H, t); 3.13 (1H, m); 3.43 (2H, t); 7.2 (1H, t); 7.3 (1H, d); 7.49 (2H, d); 7.68 (3H, d, m); 8.43 (1H, d); 8.78 (1H, s).

Example 36

Synthesis of trans-N-cyanomethyl-2-(4-hydroxymethylbenzenesulfonylmethyl)-cyclohexanecarboxamide

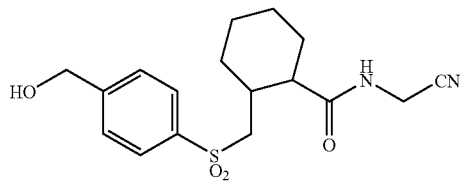

Step 1

A solution of triisopropylsilyl thiol (1.904 g, 10.0 mmol) in tetrahydrofuran (10 mL) was added to a stirred suspension of potassium hydride in tetrahydrofuran (10 mL). The resulting suspension was then added to a stirred solution of 4-bromobenzyl alcohol (1.87 g, 10 mmol) and tetrakis[triphenylphosphine]palladium(0) (0.350 g, 0.30 mmol) in benzene (25 mL). The reaction mixture was stirred at reflux for 2 h under a nitrogen atmosphere. Ethyl acetate (200 mL) was added and the solution washed with water. The organic phase was dried with magnesium sulfate, filtered, and concentrated by rotary evaporation. The crude product was purified by silica gel chromatography using a gradient of 0% to 2% ethyl acetate in dichloromethane to yield (4-triisopropylsilanylsulfanyl-phenyl)-methanol as a colorless oil.

Step 2

Cesium fluoride (0.829 g, 5.46 mmol) and cesium carbonate (0.456 g, 1.4 mmol) were added to a stirred solution of (4-triisopropylsilanylsulfanyl-phenyl)-methanol (0.808 g, 2.73 mmol) and trans-2-bromomethyl-cyclohexanecarboxylic acid cyanomethyl amide (0.906 g, 3.50 mmol) in dry dimethylformamide (910 mL). The reaction mixture was stirred at 50° C. overnight. The reaction mixture was diluted with dichloromethane and washed with 1N HCl, then with saturated aqueous sodium bicarbonate. The organic layer was dried with magnesium sulfate, filtered, and concentrated by rotary evaporation to yield trans-N-cyanomethyl-2-(4-hydroxymethyl-phenylsulfanylmethyl)-cyclohexanecarboxamide as a white solid that was carried forward without further purification.

Step 3

To a solution of the crude trans-N-cyanomethyl-2-(4-hydroxymethylphenylsulfanylmethyl)-cyclohexanecarboxamide in methanol (20 mL) was added Oxone™ (2.03 g, 3.3 mmol) of and the resulting suspension was stirred at 50° C. overnight. The reaction was not quite complete, so an additional Oxone™ (2.00 g, 3.3 mmol) was added and the reaction mixture was stirred at 50° C. for an additional 4 h. The reaction mixture was diluted with dichloromethane and then washed with water. The organic layer was dried with magnesium sulfate, filtered, and concentrated by rotary evaporation. The crude product was purified by silica gel chromatography using a gradient of 0% to 5% methanol in dichloromethane to yield the title compound as a white solid.

Example 37

Synthesis of trans-N-cyanomethyl-2-(4-benzylsulfanylmethylbenzenesulfonylmethyl)-cyclohexanecarboxamide

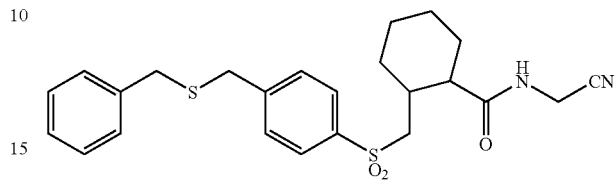

Step 1

Methanesulfonyl chloride (0.140 mL, 1.81 mmol) was added dropwise to a stirred solution of trans-N-cyanomethyl-2-(4-hydroxymethylbenzenesulfonylmethyl)-cyclohexanecarboxamide (0.576 g, 1.645 mmol) and diisopropylethylamine (0.344 mL, 1.97 mmol) in dichloromethane (5 mL) chilled to 5° C. The ice bath was removed and the reaction was allowed to proceed with stirring overnight. The reaction was not complete, so additional diisopropylethylamine (0.172 ml, 1.0 mmol) was added, followed by additional methanesulfonyl chloride (0.070 mL, 0.90 mmol). The reaction was allowed to stir an additional hour at ambient temperature. Dichloromethane (100 mL) was added and the solution was washed with water, 1N HCl, and then saturated aqueous sodium bicarbonate. The organic layer was dried with magnesium sulfate, filtered, and concentrated by rotary evaporation to yield trans-methanesulfonic acid 4-[2-(cyanomethyl-carbamoyl)-cyclohexylmethanesulfonyl]-benzyl ester as a white solid.

Step 2

Cesium carbonate (0.114 g, 0.35 mmol) was added to a solution of trans-methanesulfonic acid 4-[2-(cyanomethyl-carbamoyl)-cyclohexylmethanesulfonyl]-benzyl ester (0.150 g, 0.35 mmol) and benzyl mercaptan (0.041 mL, 0.35 mmol) in acetone (4 mL). The reaction mixture was stirred overnight at 50° C. The solids were removed by filtration and washed with warm acetone. The combined filtrates were concentrated by rotary evaporation. Purification of the residue by silica gel chromatography using a gradient of 0%-20% ethyl acetate in dichloromethane yielded the title compound as a white solid.

Example 37

Synthesis of trans-N-cyanomethyl-2-(4-benzylsulfonylmethylbenzenesulfonylmethyl)-cyclohexanecarboxamide

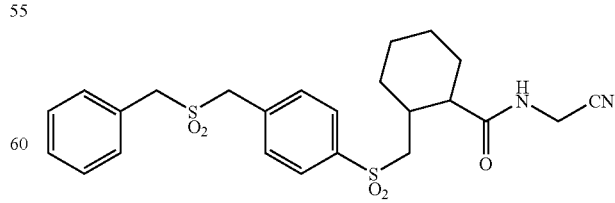

Oxone™ (0.048 g, 0.078 mmol) was added to a solution of trans-N-cyanomethyl-2-(4-benzylsulfanylmethylbenzenesulfonylmethyl)cyclohexanecarboxamide (0.013 g, 0.029 mmol) in methanol (0.5 mL). The stirred reaction mixture was heated at 50° C. overnight. Dichloromethane (100 mL)

was added and the mixture was washed with water. The organic phase was dried with magnesium sulfate, filtered, and concentrated by rotary evaporation and then dried under high vacuum to yield the title compound as a white solid. MS [ESI, (M+Na)$^+$] m/z=511.1 amu; MS [ESI, (M−H)$^−$] m/z=487.2 amu.

FORMULATION EXAMPLES

Representative Pharmaceutical Formulations Containing a Compound of Formula I are as described below:

Example 1

| ORAL FORMULATION | |
| --- | --- |
| Compound of Formula I | 10-100 mg |
| Citric Acid Monohydrate | 105 mg |
| Sodium Hydroxide | 18 mg |
| Flavoring | |
| Water | q.s. to 100 mL |

Example 2

| INTRAVENOUS FORMULATION | |
| --- | --- |
| Compound of Formula I | 0.1 to 10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

Example 3

| TABLET FORMULATION | |
| --- | --- |
| Compound of Formula I | 1% |
| Microcrystalline Cellulose | 73% |
| Stearic Acid | 25% |
| Colloidal Silica | 1% |

BIOLOGICAL EXAMPLES

Example 1

Cathepsin B Assay

Solutions of test compounds (varying concentrations in 10 μL of DMSO) were diluted into assay buffer (40 μL, comprising: BES, 50 mM (pH 6); polyoxyethylenesorbitan monolaurate, 0.05%; and DTT, 2.5 mM). Human cathepsin B (0.025 pMoles in 25 μL of assay buffer) was added to the dilutions. The assay solutions were mixed for 5-10 seconds on a shaker plate, covered and incubated for 30 minutes at room temperature. Z-FR-AMC (20 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested by the above-described assay and observed to exhibit cathepsin B inhibitory activity.

Example 2

Cathepsin K Assay

Solutions of test compounds (varying concentrations in 10 μL of DMSO) were diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5-10 seconds on a shaker plate, covered and incubated for 30 minutes at room temperature. Z-Phe-Arg-AMC (4 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested by the above-described assay and observed to exhibit cathepsin K inhibitory activity.

Example 3

Cathepsin L Assay

Solutions of test compounds (varying concentrations in 10 μL of DMSO) were diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5-10 seconds on a shaker plate, covered and incubated for 30 minutes at room temperature. Z-Phe-Arg-AMC (1 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested by the above-described assay and observed to exhibit cathepsin L inhibitory activity.

Example 4

Cathepsin S Assay

Solutions of test compounds (varying concentrations in 10 μL of DMSO) were diluted into assay buffer (40 μL, comprising: MES, 50 mM (pH 6.5); EDTA, 2.5 mM; and NaCl, 100 mM). Human cathepsin S (0.158 pMoles in 25 μL of assay buffer) was added to the dilutions. The assay solutions were mixed for 5-10 seconds on a shaker plate, covered and incubated for 30 minutes at room temperature. Z-Val-Val-Arg-AMC (9 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested by the above-described assay and observed to exhibit cathepsin S inhibitory activity.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed is:

1. A compound of Formula I:

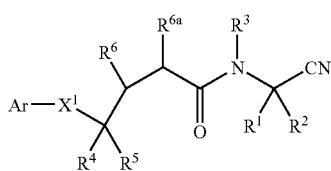

I wherein:
$X^1$ is $-S(O)_2-$;
$R^1$ is hydrogen or $(C_{1-6})$alkyl;
$R^2$ is hydrogen or $(C_{1-6})$alkyl;
$R^3$ is hydrogen or $(C_{1-6})$alkyl;
$R^6$ and $R^{6a}$ together with the carbon atoms to which they are attached form:
(i) $(C_{3-7})$monocyclic cycloalkylene;
$R^4$ and $R^5$ are each independently hydrogen or $(C_{1-6})$alkyl; and
Ar is selected from the group consisting of:
(i) $-(C_{0-3})$alkylene-$Ar^1$ where $Ar^1$ is phenyl;
(ii) $-(C_{0-3})$alkylene-$Ar^1-X^4-Ar^2$ where $Ar^1$ is as defined above;
(iii) $-(C_{0-3})$alkylene-$Ar^1-X^4-Ar^2-X^5-Ar^3$ where $Ar^1$ is as defined above; and
(iv) $-(C^{0-3})$alkylene-$Ar^1-X^4-Ar^2-X^5-Ar^3-X^6-Ar^4$ where $Ar^1$ is as defined above;
wherein:
$X^4$, $X^5$ and $X^6$ are independently selected from the group consisting of a bond, $(C_{1-6})$alkylene, $-X^7NR^{15}X^8-$, $-X^7NR^{15}C(O)X^8-$, $-X^7C(O)NR^{15}X^8-$, $-X^7NR^{15}C(O)OX^8-$, $-X^7OC(O)NR^{15}X^8-$, $-X^7NR^{15}C(O)NR^{15}X^8-$, $-X^7NR^{15}C(NR^{15})NR^{15}X^8-$, $-X^7OX^8-$, $-X^7C(O)X^8$, $-X^7C(O)OX^8-$, $-X^7OC(O)X^8-$, $-X^7S(O)_2NR^{15}X^8-$, $-X^7SX^8-$, $-X^7S(O)X^8-$, $-X^7S(O)_2X^8-$, $-X^7NR^{15}S(O)_2X^8-$, and heteroalkylene, and $X^4$ and $X^7$ can additionally be $(C_{2-6})$alk-1-ynyl, wherein $X^7$ and $X^8$ independently are a bond or $(C_{1-6})$alkylene and each $R^{15}$ is hydrogen or $(C_{1-6})$alkyl; and
$Ar^2$, $Ar^3$ and $Ar^4$ are independently selected from the group consisting of:
(i) $(C_{3-8})$cycloalkyl;
(ii) $(C_{3-8})$cycloalkenyl;
(iii) heterocycloalkyl;
(iv) heterocycloalkenyl;
(v) $(C_{6-14})$aryl; and
(vi) heteroaryl;

provided that only one of $Ar^1$, $Ar^2$, $Ar^3$, and $Ar^4$ can be cycloalkyl, cycloalkenyl, heterocycloalkyl, heterocycloalkenyl, aryl or heteroaryl having more than six ring atoms;

and furthermore when $Ar^2$, $Ar^3$, and $Ar^4$ is cycloalkyl, cycloalkenyl, heterocycloalkyl or heterocycloalkenyl it is optionally substituted with one, two, or three groups independently selected from the group consisting of $(C_{1-6})$alkyl, $(C_{1-6})$alkylidene, $(C_{1-6})$alkylimino, cyano, halo, halo-substituted $(C_{1-4})$alkyl, imino, nitro, oxo, thioxo, $-X^9NR^{16}R^{16}$, $-X^9NR^{16}C(O)R^{16}$, $-X^9C(O)NR^{16}R^{16}$, $-X^9NR^{16}C(O)OR^{16}$, $-X^9OC(O)NR^{16}R^{16}$, $-X^9NR^{16}C(O)NR^{16}R^{16}$, $-X^9NR^{16}C(NR^{16})NR^{16}R^{16}$, $-X^9OR^{16}$, $-X^9C(O)R^{16}$, $-X^9C(O)OR^{16}$, $-X^9OC(O)R^{16}$, $-X^9S(O)_2NR^{16}R^{16}$, $-X^9P(O)(OR^{16})OR^{16}$, $-X^9OP(O)(OR^{16})OR^{16}$, $-X^9SR^{16}$, $-X^9S(O)R^{17}$, $-X^9S(O)_2R^{17}$, and $-X^9NR^{16}S(O)_2R^{17}$, wherein $X^9$ is a bond, $(C_{1-6})$alkylene, or $(C_{2-6})$alk-1-ynyl, $R^{16}$ at each occurrence independently is hydrogen, $(C_{1-6})$alkyl, or halo-substituted $(C_{1-3})$alkyl, and $R^{17}$ is $(C_{1-6})$alkyl or halo-substituted $(C_{1-3})$alkyl; and when $Ar^1$, $Ar^2$, $Ar^3$, and $Ar^4$ is aryl or heteroaryl it is optionally substituted with one, two, or three groups independently selected from the group consisting of $(C_{1-6})$alkyl, cyano, halo, halo-substituted $(C_{1-4})$alkyl, nitro, $-X^9NR^{16}R^{16}$, $-X^9NR^{16}C(O)R^{16}$, $-X^9C(O)NR^{16}R^{16}$, $-X^9NR^{16}C(O)OR^{16}$, $-X^9OC(O)NR^{16}R^{16}$, $-X^9NR^{16}C(O)NR^{16}R^{16}$, $-X^9NR^{16}C(NR^{16})NR^{16}R^{16}$, $-X^9OR^{16}$, $-X^9C(O)R^{16}$, $-X^9C(O)OR^{16}$, $-X^9OC(O)R^{16}$, $-X^9S(O)_2NR^{16}R^{16}$, $-X^9P(O)(OR^{16})OR^{16}$, $-X^9OP(O)(OR^{16})OR^{16}$, $-X^9SR^{16}$, $-X^9S(O)R^{17}$, $-X^9S(O)_2R^{17}$, $-OS(O)_2R^{17}$, $-X^9NR^{16}S(O)_2R^{17}$, and heteroalkyl wherein $X^9$ is a bond or $(C_{1-6})$alkylene, $R^{16}$ at each occurrence independently is hydrogen, $(C_{1-6})$alkyl, or halo-substituted $(C_{1-3})$alkyl, and $R^{17}$ is $(C_{1-6})$alkyl, or halo-substituted $(C_{1-3})$alkyl; and individual isomers and mixtures of isomers; and pharmaceutically acceptable salts thereof provided that there are no more than 5 ring systems in a compound of Formula I.

2. The compound of claim 1 wherein $R^6$ and $R^{6a}$ together with the carbon atoms to which they are attached form $(C_{3-7})$monocyclic cycloalkylene, which is optionally substituted with hydroxy or $(C_{1-3})$alkyl.

3. The compound of claim 1 wherein $R^6$ and $R^{6a}$ together with the carbon atoms to which they are attached form:

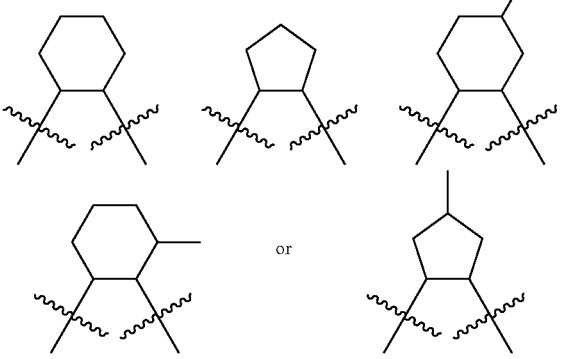

4. The compound of claim 2 wherein $R^1$, $R^2$, $R^3$, $R^4$ and $R^5$ are hydrogen.

5. The compound of claim 4 wherein $X^1$ is —$SO_2$—; and Ar is $Ar^1$ where $Ar^1$ is phenyl is optionally substituted with one or two substituents independently selected from $(C_{1-6})$alkyl, cyano, halo, halo-substituted $(C_{1-4})$alkyl, nitro, —$NR^{16}R^{16}$, —$NR^{16}C(O)R^{16}$, —$X^9OR^{16}$, —$X^9C(O)OR^{16}$, —$SR^{16}$, —$S(O)_2R^{17}$ and —$NR^7S(O)_2R^{17}$.

6. The compound of claim 4 wherein $X^1$ is —$SO_2$—; and Ar is $Ar^1$ where $Ar^1$ is phenyl substituted with heteroalkyl.

7. The compound of claim 4 wherein $X^1$ is —$SO_2$—; and Ar is $Ar^2$—$X^4$—$Ar^1$— where $Ar^1$ is phenyl; and $X^4$ is a bond, —$(C_{1-6})$alkylene, —$X^7NR^{15}C(O)X^8$—, —$X^7C(O)NR^{15}X^8$—, —$X^7OX^8$—, —$X^7SX^8$—, —$X^7S(O)X^8$—, or —$X^7S(O)_2X^8$.

8. The compound of claim 4 wherein $X^1$ is —$SO_2$—; and Ar is $Ar^2$—$X^4$—$Ar^1$— where $Ar^1$ is phenyl; and $X^4$ is heteroalkylene.

9. The compound of claim 4 wherein —$Ar^1$—$X^4$—$Ar^2$ is 4-(morpholin-4-yl)phenyl, 4-(1-methylpyrrolidin-2-ylmethoxy)phenyl, 4-(1-methylpiperidin-4-yloxy)phenyl, 4-[2-(morpholin-4-yl-N-oxide)ethoxy]phenyl, 4-(4-thiolphenylsulfanyl)-phenyl, 4-(4-methylpiperazin-1-yl)phenyl, 4-[2-(morpholin-4-yl)ethoxy]phenyl, 4-(4-tert-butoxycarbonylpiperidin-4-yloxy)phenyl, 4-piperidin-4yloxyphenyl, 4-thien-2-ylphenyl, 4-(3-aminophenyl)phenyl, 4-(pyridin-4-ylsulfanyl)phenyl, 4-(2-phenylethylsulfinyl)phenyl, 4-(4-methoxyphenylsulfanyl)phenyl, 4-[2-(phenyl)ethylsulfanyl]-phenyl, 4-(2-aminophenylsulfanyl)-phenyl, 4-(2-chlorophenylmethyl-sulfanyl)phenyl, 4-(2-methylphenylmethylsulfanyl)phenyl, 4-(pyridin-2-ylsulfanyl)phenyl, 4-(4-chlorophenylmethylsulfanyl)phenyl, 4-(3-aminophenyl-sulfanyl)-phenyl, 4-(pyridin-3-ylmethyl-aminocarbonylmethylsulfanyl)phenyl, 4-[2-(2-chloropyridin-3-ylcarbonylamino)-ethylsulfanyl]phenyl, 4-(4-aminophenylsulfanyl)phenyl, 4-[2-(pyridin-4-yl-carbonylamino)-ethylsulfanyl]phenyl, 4-(4-dimethylaminophenylmethylamino-carbonylmethylsulfanyl)phenyl, 4-(thien-2-ylsulfanyl)phenyl, 4-(furan-2-ylmethylsulfanyl)-phenyl, 4-(pyridin-4-ylmethylaminocarbonylmethylsulfanyl)phenyl, 4-[2-(furan-2-yl)ethylaminocarbonylmethylsulfanyl)-phenyl, 4-[2-(pyridin-4-yl)ethylaminocarbonylmethylsulfanyl]phenyl, 4-(1-methylpiperidin-4-ylsulfanyl)phenyl, 4-(2-chlorophenylmethylaminocarbonylmethylsulfanyl)-phenyl, 4-(4-methoxyphenylmethylaminocarbonylmethylsulfanyl)phenyl, 4-(furan-2-ylmethylaminocarbonyl-methylsulfanyl)phenyl, 4-(4-chlorophenylmethylaminocarbonyl-methylsulfanyl)phenyl, 3-fluoro-4-(1-methylimidazol-2-ylsulfanyl)phenyl, 4-(3-dimethylaminophenylmethylaminocarbonyl-methylsulfanyl)phenyl, 3-fluoro-4-[2-(phenyl)ethylsulfanyl]phenyl, 3-fluoro-4-(pyrimidin-2-ylsulfanyl)phenyl, 4-[2-(pyridin-2-yl)ethylsulfanyl]phenyl, 4-(1-tert-butylpiperazin-1-ylcarbonylmethylsulfanyl)phenyl, 4-[2-(phenyl)ethylsulfonyl]phenyl, 3-fluoro-4-[2-(pyridin-2-yl)ethylsulfanyl]phenyl, 4-(4-tert-butylpiperazin-1-ylcarbonylmethoxy)phenyl, 4-(2-phenylethoxy)phenyl, 4-[2-(thien-2-yl)ethylaminocarbonylmethylsulfonyl]phenyl, 4-[2-(pyridin-2-yl)ethylsulfonyl]phenyl, 3-fluoro-4-[2-(phenyl)ethylsulfonyl]phenyl, 4-[2-(pyridin-4-yl)ethylaminocarbonylmethyl-oxy]phenyl, 4-(3-methyl-[1,3,5]oxadiazol-4-ylmethylamino-carbonylmethylsulfanyl)phenyl, 4-[(2-morpholin-4-ylcarbonylamino)-ethylsulfanyl]phenyl, 4-[2-(pyridin-3-yloxy)ethylsulfanyl]-phenyl, 4-(piperidin-3-ylaminocarbonylmethylsulfanyl)phenyl, 4-[2-(morpholin-4-ylcarbonylamino)-ethyloxy]phenyl, 4-[2-(morpholin-4-yl)ethylaminocarbonyl-methylsulfanyl]-phenyl, 4-[2-(pyridin-2-yl)ethylsulfanyl]phenyl, 4-(4-isopropylpiperazin-4-ylcarbonylmethylsulfanyl)phenyl, 4-(furan-2-ylmethylaminocarbonylmethyl)phenyl, 4-[2-(furan-2-ylmethylaminocarbonyl)-ethyl]phenyl, 4-benzylsulfanylmethylphenyl, 4-(benzylsulfonyl-methyl) phenyl, 4-[3-(furan-2-ylmethylaminocarbonyl)propyl]phenyl, 4-[2-(pyridin-2-yl)-ethylsulfanylmethyl]phenyl, 4-[2-(pyridin-2-yl)ethylsulfonylmethyl]phenyl, 4-(thien-2-ylethylaminocarbonylmethylsulfonyl)-phenyl, or 4-(furan-2-ylmethylaminocarbonyl)phenyl.

10. The compound of claim 1 wherein $R^1$, $R^2$, $R^3$, $R^4$ and $R^5$ are hydrogen;
$R^6$ and $R^{6a}$ together with the carbon atoms to which they are attached form $(C_{3-7})$monocyclic cycloalkylene; where monocycloalkylene is optionally substituted with alkyl;
$X^1$ is —S—, or $SO_2$—; and
Ar is:
(i) phenyl optionally substituted with one or two substituents independently selected from $(C_{1-6})$alkyl, cyano, halo, halo-substituted $(C_{1-4})$alkyl, nitro, —$X^9NR^{16}R^{16}$, —$C(O)R^{16}$, —$NR^{16}C(O)R^{16}$, —$X^9OR^{16}$, —$X^9C(O)OR^{16}$, —$SR^{16}$, —$S(O)_2R^{17}$, —$OS(O)_2R^{17}$ and —$NR^7S(O)_2R^{17}$ where $X^9$ is a bond or $(C_{1-6})$alkylene, $R^{16}$ at each occurrence independently is hydrogen, $(C_{1-6})$alkyl, or halo-substituted $(C_{1-3})$alkyl, and $R^{17}$ is $(C_{1-6})$alkyl, or halo-substituted $(C_{1-3})$alkyl; or
(ii) phenyl optionally substituted with heteroalkyl; or
(iii) —$Ar^1$—$X^4$—$Ar^2$ where $Ar^1$ is phenyl, $X^4$ is selected from the group consisting of a bond, —$X^7NR^{15}C(O)X^8$—, —$X^7OX^8$—, —$X^7SX^8$—, —$X^7S(O)X^8$—, and —$X^7S(O)_2X^8$— wherein $X^7$ and $X^8$ independently are a bond or —$(C_{1-6})$alkylene and $R^{15}$ is hydrogen or —$(C_{1-6})$alkyl; or $X^4$ is heteroalkylene; and $Ar^2$ is phenyl optionally substituted with $(C_{1-6})$alkyl, —$OR^{16}$, halo, or —$NR^{16}R^{16}$; or heteroaryl containing five or six ring atoms wherein one, two or three rings atoms are heteroatoms selected from the group consisting of nitrogen, oxygen or sulfur and wherein the heteroaryl ring is optionally substituted with a group selected from halo; or heterocycloalkyl ring of six ring atoms wherein one or two ring atoms are independently selected from nitrogen or oxygen and wherein said heterocycloalkyl ring is optionally substituted with a substituent selected from $(C_{1-6})$alkyl, or —$OC(O)R^{16}$ where $R^{16}$ at each occurrence independently is hydrogen, $(C_{1-6})$alkyl, or halo-substituted $(C_{1-3})$alkyl; or
(iv) $Ar^3$—$X^5$—$Ar^2$—$X^4$—$Ar^1$— where $Ar^1$ is phenyl; $X^4$ is bond or —$COCH_2S$—; $Ar^2$ is 5 or 6 membered heteroaryl ring containing one or two heteroatoms selected from nitrogen or sulfur or 6 membered heterocycloalkyl ring containing one or two nitrogen atoms; $X^5$ is bond, —O—, or alkylene; and $Ar^3$ is phenyl optionally substituted with halo; a 6 membered heterocycloalkyl ring containing one or two nitrogen atoms and optionally substituted with $(C_{1-6})$alkyl, or —$OC(O)R^{16}$ where $R^{16}$ at each occurrence independently is hydrogen, $(C_{1-6})$alkyl, or halo-substituted $(C_{1-3})$alkyl; or a 5 or 6 membered heteroaryl ring containing one or two heteroatoms selected from nitrogen or sulfur.

11. The compound of claim 10 wherein $R^6$ and $R^{6a}$ form:

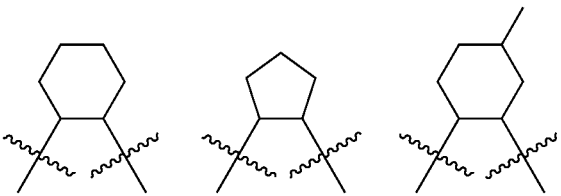

-continued

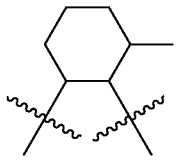 or 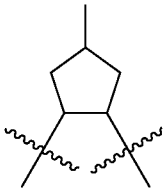

12. The compound of claim 11 wherein Ar is 4-fluorophenyl, 4-bromophenyl, 4-chlorophenyl, 4-methylphenyl, 4-methoxyphenyl, 4-(-NHCOCH₃)phenyl., 4-nitrophenyl, 4-trifluoromethylphenyl, 4-tert-butylphenyl, 4-trifluoromethylphenyl, 4-methylsulfanylphenyl, 4-methylsulfonylphenyl, 4-hydroxyphenyl, 4-aminophenyl, 2-chlorophenyl, 2,4-dichlorophenyl, 2,5-dichlorophenyl, 2-methylphenyl, 3,4-dichlorophenyl, 3,5-dichlorophenyl, 3-chlorophenyl, 4-dimethylaminophenyl, 3-methylphenyl, 4-trifluoromethoxyphenyl, 3-methoxyphenyl, 3,4-dimethoxyphenyl, 2,5-dimethoxyphenyl, 4-thiolphenyl, 4-isopropyloxyphenyl, 3-trifluoromethylphenyl, 3-(-NHCOCH₃)phenyl, 3-fluorophenyl, 3-aminophenyl, 4-carboxymethylphenyl, 4-carboxyphenyl, 3-hydroxyphenyl, 3-formylaminophenyl, 3-trifluoroacetylaminophenyl, 4-hydroxymethylphenyl, 4-trifluorosulfonyloxyphenyl, 3-carboxylphenyl, 4-ethylsulfanylphenyl, 3-methylsulfonylaminophenyl, 3,4-dimethylsulfanylphenyl, 3,4-difluorophenyl, 4-tert-butylsulfanylphenyl, 2,4-difluorophenyl, 3-fluoro-4-methylsulfanylphenyl, 4-(3-carboxypropyl)phenyl, 4-(2-carboxyethyl)phenyl, 4-carboxymethyl-phenyl, 4-iodophenyl, 4-(2,2,2-trifluoroethylsulfanyl)phenyl, 4-difluoromethoxyphenyl, 4-difluoromethylsulfanylphenyl, 4-ethoxycarbonylmethylsulfanylphenyl, 3-hydroxypropylsulfanylphenyl, 2-aminoethylsulfanylphenyl, 4-(2-tert-butoxycarbonylaminoethylsulfanyl)phenyl, 4-[2-(2,2,2-trifluoroethylamino)-ethylsulfanyl]phenyl, 4-methylaminocarbonylmethylsulfanylphenyl, 4-[2-(acetylamino)ethoxy]-phenyl, 4-[2-aminoethylsulfanyl]phenyl, 4-[2-(acetylamino)ethylsulfanyl]phenyl, 3-fluoro-4-[2-(ethylsulfonylamino)ethylsulfanyl]phenyl, 3-fluoro-4-[2-(dimethylaminosulfonylamino)-ethylsulfanyl]phenyl, 4-[2-(methylsulfonyloxy)ethylsulfanyl]phenyl, 4-[2-hydroxyethyl-sulfanyl]phenyl, 4-methoxycarbonylmethoxyphenyl, 4-[1-ethoxycarbonylethylsulfanyl]phenyl, 4-trifluoromethylsulfonyloxyphenyl, or 4-[2-bromoethylsulfanyl]phenyl, 4-(morpholin-4-yl)phenyl, 4-(1-methylpyrrolidin-2-ylmethoxy)phenyl, 4-(1-methylpiperidin-4-yloxy)phenyl, 4-[2-(morpholin-4-yl-N-oxide)ethoxy]phenyl, 4-(4-thiolphenylsulfanyl)-phenyl, 4-(4-methylpiperazin-1-yl)phenyl, 4-[2-(morpholin-4-yl)ethoxy]phenyl, 4-(4-tert-butoxycarbonylpiperidin-4-yloxy)phenyl, 4-piperidin-4-yloxyphenyl, 4-thien-2-ylphenyl, 4-(3-aminophenyl)phenyl, 4-(pyridin-4-ylsulfanyl)phenyl, 4-(2-phenylethylsulfinyl)phenyl, 4-(4-methoxyphenylsulfanyl)phenyl, 4-[2-(phenyl)ethylsulfanyl]-phenyl, 4-(2-aminophenylsulfanyl)-phenyl, 4-(2-chlorophenylmethylsulfanyl)phenyl, 4-(2-methylphenylmethylsulfanyl)phenyl, 4-(pyridin-2-ylsulfanyl)phenyl, 4-(4-chlorophenylmethylsulfanyl)phenyl, 4-(3-aminophenylsulfanyl)-phenyl, 4-(pyridin-3-ylmethylaminocarbonylmethylsulfanyl)phenyl, 4-[2-(2-chloropyridin-3-ylcarbonylamino)ethyl-sulfanyl]phenyl, 4-(4-aminophenylsulfanyl)phenyl, 4-[2-(pyridin-4-ylcarbonylamino)-ethylsulfanyl]phenyl, 4-(4-dimethylaminophenylmethylaminocarbonylmethylsulfanyl)phenyl, 4-(thien-2-ylsulfanyl)phenyl, 4-(furan-2-ylmethylsulfanyl)-phenyl, 4-(pyridin-4-ylmethylaminocarbonylmethylsulfanyl)phenyl, 4-[2-(furan-2-yl)ethylaminocarbonylmethylsulfanyl)phenyl, 4-[2-(pyridin-4-yl)ethylaminocarbonylmethylsulfanyl]phenyl, 4-(1-methylpiperidin-4-ylsulfanyl)phenyl, 4-(2-chlorophenylmethylaminocarbonylmethylsulfanyl)-phenyl, 4-(4-methoxyphenylmethylaminocarbonylmethylsulfanyl)phenyl, 4-(furan-2-ylmethylaminocarbonylmethylsulfanyl)phenyl, 4-(4-chlorophenylmethylaminocarbonyl-methylsulfanyl)phenyl, 3-fluoro-4-(1-methylimidazol-2-ylsulfanyl)phenyl, 4-(3-dimethylaminophenylmethylaminocarbonylmethylsulfanyl)phenyl, 3-fluoro-4-[2-(phenyl)ethylsulfanyl]phenyl, 3-fluoro-4-(pyrimidin-2-ylsulfanyl)phenyl, 4-[2-(pyridin-2-yl)ethylsulfanyl]phenyl, 4-(1-tert-butylpiperazin-1-ylcarbonylmethylsulfanyl)phenyl, 4-[2-(phenyl)ethylsulfonyl]phenyl, 3-fluoro-4-[2-(pyridin-2-yl)ethylsulfanyl]phenyl, 4-(4-tert-butylpiperazin-1-ylcarbonylmethoxy)phenyl, 4-(2-phenylethoxy)phenyl, 4-[2-(thien-2-yl)ethylaminocarbonylmethylsulfonyl]phenyl, 4-[2-(pyridin-2-yl)ethylsulfonyl]phenyl, 3-fluoro-4-[2-(phenyl)ethylsulfonyl]phenyl, 4-[2-(pyridin-4-yl)ethylaminocarbonylmethyl-oxy]phenyl, 4-(3-methyl-[1,3,5]oxadiazol-4-ylmethylamino-carbonylmethylsulfanyl)phenyl, 4-[(2-morpholin-4-ylcarbonylamino)-ethylsulfanyl]phenyl, 4-[2-(pyridin-3-yloxy)ethylsulfanyl]-phenyl, 4-(piperidin-3-ylaminocarbonylmethylsulfanyl)phenyl, 4-[2-(morpholin-4-ylcarbonylamino)-ethyloxy]phenyl, 4-[2-(morpholin-4-yl)ethylaminocarbonyl-methylsulfanyl]-phenyl, 4-[2-(pyridin-2-yl)ethylsulfanyl]phenyl, 4-(4-isopropylpiperazin-4-ylcarbonylmethylsulfanyl)phenyl, 4-(furan-2-ylmethylaminocarbonylmethyl)phenyl, 4-[2-(furan-2-ylmethylaminocarbonyl)-ethyl]phenyl, 4-benzylsulfanylmethylphenyl, 4-(benzylsulfonyl-methyl)phenyl, 4-[3-(furan-2-ylmethylaminocarbonyl)propyl]phenyl, 4-[2-(pyridin-2-yl)ethylsulfanylmethyl]phenyl, 4-[2-(pyridin-2-yl)ethylsulfonylmethyl]phenyl, 4-(thien-2-ylethylaminocarbonylmethylsulfonyl)-phenyl, or 4-(furan-2-ylmethylaminocarbonyl)phenyl, 4-[2-(4-isopropylpiperazin-1-yl)thiazol-4-yl]phenyl, 4-[4-(tert-butoxycarbonylpiperazin-1-yl)-phenyl]phenyl, 4-[4-(piperazin-1-yl)phenyl]phenyl, 4-[4-(morpholin-4-yl)piperidin-1-yl]phenyl, 4-[4-(piperidin-1-yloxy)phenyl]phenyl, 4-[4-(pyridin-4-yl)piperazin-1-ylcarbonylmethylsulfanyl]phenyl, 4-[4-(pyridin-2-yl)piperazin-1-ylcarbonylmethylsulfanyl]phenyl, 4-[4-(pyrimidin-2-yl)piperazin-1-ylcarbonylmethylsulfanyl]phenyl, 4-[4-(4-bromophenyl)piperazin-1-ylcarbonylmethylsulfanyl]-phenyl, or 4-[4-benzylpiperidin-4-ylaminocarbonyl-methylsulfanyl]phenyl.

13. The compound of claim 11 wherein Ar is 4-[2-(pyridin-4-yl)ethylamino-carbonylmethylsulfanyl]phenyl, 4-[2-(morpholin-4-yl)ethylaminocarbonyl-methylsulfanyl]phenyl, 4-[2-(pyridin-2-yl)ethylsulfanyl]phenyl, 4-(2-phenylethylsulfanyl)phenyl, 4-(4-dimethylaminophenylmethylaminocarbonylmethyl-sulfanyl)phenyl, 4-[2-(pyridin-3-yloxy)ethylsulfanyl]phenyl, 4-(4-chlorophenylmethylaminocarbonylmethylsulfanyl)phenyl, 3-fluoro-4-(pyridin-2-ylethylsulfanyl)phenyl, 4-(piperidin-3-ylaminocarbonylmethylsulfanyl)-phenyl, 4-(2-chlorophenylmethylamino-carbonylmethylsulfanyl)phenyl, 4-(pyridin-3-ylmethylamino-carbonylmethylsulfanyl)phenyl, 4-[2-(thien-2-yl)ethylaminocarbonylmethyl-sulfanyl]phenyl, 4-(3-dimethylaminophenylmethylaminocarbonylmethylsulfanyl)phenyl, 4-[2-(pyridin-4-ylcarbonylamino)ethylsulfanyl]phenyl, 4-(4-methoxyphenylmethylaminocarbonylmethylsulfanyl)phenyl, 4-(4- isopropylpiperazin-1-ylcarbonylmethylsulfanyl)phenyl, or 4-(furan-2-ylmethylsulfanyl)phenyl, 4-hydroxyphenyl, 4-methylsulfanylphenyl, 4-[2-aminoethyl-sulfanyl]phenyl, 4-[2-(methylsulfonyloxy)ethylsulfanyl]-phenyl, 4-[2-tert-butoxycarbonyl-aminoethylsulfanyl]phenyl, or 4-[2-bromo-ethylsulfanyl]phenyl, 4-[4-(piperazin-1-yl)phenyl]-phenyl, 4-[4-(pyridin-4-yl)piperazin-1-ylcarbonylmethylsulfanyl]-phenyl, 4-[4-(piperidin-1-yloxy)phenyl]phenyl, or 4-[4-benzylpiperidin-4-ylaminocarbonyl-methylsulfanyl]phenyl.

14. A compound selected from the group consisting of:
trans-N-cyanomethyl-2-(4-fluorophenylsulfanylmethyl) cyclohexanecarboxamide;
trans-N-cyanomethyl-2-[4-(4-piperazin-1-ylphenyl)phenylsulfanylmethyl)-cyclohexanecarboxamide;
trans-N-cyanomethyl-2-(4-bromophenylsulfanylmethyl)-cyclohexanecarboxamide;
trans-N-cyanomethyl-2-(4-bromophenylsulfinylmethyl) cyclohexanecarboxamide;
trans-N-cyanomethyl-2-(4-bromobenzenesulfonylmethyl)cyclohexanecarboxamide;
trans-N-cyanomethyl-2-(phenylsulfanylmethyl)cyclohexanecarboxamide;
trans-N-cyanomethyl-2-(4-chlorophenylsulfanylmethyl) cyclohexanecarboxamide;
trans N-cyanomethyl-2-(3,4-dichlorophenylsulfanylmethyl)cyclohexanecarboxamide;
trans-N-cyanomethyl-2-(4-methylphenylsulfanylmethyl) cyclohexanecarboxamide;
trans-N-cyanomethyl-2-(4-methoxyphenylsulfanylmethyl)cyclohexanecarboxamide;
trans-N-cyanomethyl-2-[4-(morpholin-4-yl)phenylsulfanylmethyl]-cyclohexanecarboxamide;
trans-N-cyanomethyl-2-[4-(morpholin-4-yl)benzenesulfonylmethyl]-cyclohexanecarboxamide;
trans-N-cyanomethyl-2-(4-methylcarbonylaminophenylsulfanylmethyl)-cyclohexanecarboxamide;
trans-N-cyanomethyl-2-(benzenesulfonylmethyl)cyclohexanecarboxamide;
trans-N-cyanomethyl-2-(4-chlorobenzenesulfonylmethyl)cyclohexanecarboxamide;
trans-N-cyanomethyl-2-(3,4-dichlorobenzenesulfonylmethyl)cyclohexanecarboxamide;
trans-N-cyanomethyl-2-(4-methylbenzenesulfonylmethyl)cyclohexanecarboxamide;
trans-N-cyanomethyl-2-(4-methoxybenzenesulfonylmethyl)cyclohexanecarboxamide;
trans-N-cyanomethyl-2-(4-nitrophenylsulfanylmethyl)cyclohexanecarboxamide;
trans-N-cyanomethyl-2-(4-tert-butylphenylsulfanylmethyl)cyclohexanecarboxamide.
trans-N-cyanomethyl-2-(4-trifluoromethylphenylsulfanylmethyl)-cyclohexanecarboxamide;
trans-N-cyanomethyl-2-(4-methylsulfanylphenylsulfanylmethyl)-cyclohexanecarboxamide;
trans-N-cyanomethyl-2-(4-fluorobenzenesulfonylmethyl)cyclohexanecarboxamide;
trans-N-cyanomethyl-2-(4-methylcarbonylaminobenzenesulfonylmethyl)-cyclohexane-carboxamide;
trans-N-cyanomethyl-2-(4-nitrobenzenesulfonylmethyl)cyclohexanecarboxamide;
trans-N-cyanomethyl-2-(4-tert-butylbenzenesulfonylmethyl)cyclohexanecarboxamide;
trans-N-cyanomethyl-2-(4-methylsulfonylbenzenesulfonylmethyl)-cyclohexanecarboxamide;
trans-N-cyanomethyl-2-(4-hydroxyphenylsulfanylmethyl)cyclohexanecarboxamide;
trans-N-cyanomethyl-2-(4-aminobenzenesulfonylmethyl)cyclohexanecarboxamide;
trans-N-cyanomethyl-2-(4-trifluoromethylbenzenesulfonylmethyl)-cyclohexanecarboxamide;
trans-N-cyanomethyl-2-(4-hydroxybenzenesulfonylmethyl)cyclohexanecarboxamide;
trans-N-cyanomethyl-2-{4-[2-(4-isopropylpiperazin-1-yl)thiazol-4-yl]benzenesulfonylmethyl}cyclohexanecarboxamide;
trans-N-cyanomethyl-2-[4-(4-thiolphenylsulfanyl)phenylsulfanylmethyl)-cyclohexanecarboxamide;
trans-N-cyanomethyl-2-{4-[4-(4-tert-butoxycarbonylpiperazin-1-yl)phenyl]-phenylsulfanylmethyl}cyclohexanecarboxamide
trans-N-cyanomethyl-2-(2,4-dichlorobenzylsulfanylmethyl)cyclohexanecarboxamide;
trans-N-cyanomethyl-2-(2,4-dichlorophenylsulfanylmethyl)cyclohexanecarboxamide;
trans-N-cyanomethyl-2-[4-(1-methylpyrrolidin-2-ylmethyloxy)phenylsulfanylmethyl]-cyclohexanecarboxamide;
trans-N-cyanomethyl-2-(4-dimethylaminophenylsulfanylmethyl)cyclohexanecarboxamide;
trans-N-cyanomethyl-2-(4-dimethylaminobenzenesulfonylmethyl)-cyclohexanecarboxamide;
trans-N-cyanomethyl-2-(4-trifluoromethoxyphenylsulfanylmethyl)-cyclohexanecarboxamide;
trans-N-cyanomethyl-2-(3,4-dimethoxyphenylsulfanylmethyl)-cyclohexanecarboxamide;
trans-N-cyanomethyl-2-[4-(1-methylpiperidin-4-yloxy)phenylsulfanylmethyl]-cyclohexanecarboxamide;
trans-N-cyanomethyl-2-[4-(3-dimethylaminopropyloxy)phenylsulfanylmethyl]-cyclohexanecarboxamide;
trans-N-cyanomethyl-2-[4-(2-morpholin-4-ylethyloxy)benzenesulfonylmethyl]-cyclohexanecarboxamide N-oxide;
trans-N-cyanomethyl-2-[4-(1-methylpiperazinyl)benzenesulfonylmethyl]-cyclohexanecarboxamide;
trans-N-cyanomethyl-2-[4-(4-morpholin-4-ylpiperidin-1-yl)benzenesulfonylmethyl]-cyclohexanecarboxamide;
trans-N-cyanomethyl-2-(4-methoxyphenylsulfanylmethyl)-cyclopentanecarboxamide;
trans-N-cyanomethyl-2-[4-(4-tert-butoxypiperidin-4-yloxy)phenylsulfanylmethyl]-cyclohexanecarboxamide;
trans-N-cyanomethyl-2-[4-(4-tert-butoxypiperidin-4-yloxy)benzenesulfonylmethyl]-cyclohexanecarboxamide;
trans-N-cyanomethyl-6-(4-fluorobenzenesulfonylmethyl)cyclohex-3-enecarboxamide;
trans-N-cyanomethyl-6-(4-methylsulfanylbenzenesulfonylmethyl)cyclohex-3-enecarboxamide;
trans-N-cyanomethyl-2-(3-carboxymethylphenylsulfanylmethyl)-cyclohexanecarboxamide;
trans-N-cyanomethyl-2-(4-thien-3-ylbenzenesulfonylmethyl)cyclohexanecarboxamide;
trans-N-cyanomethyl-2-(3-trifluoroacetylaminophenylsulfanylmethyl)-cyclohexanecarboxamide;
trans-N-cyanomethyl-2-(3-methylsulfonylaminophenylsulfanylmethyl)-cyclohexanecarboxamide;
trans-N-cyanomethyl-2-(4-ethoxycarbonylmethylsulfanylbenzenesulfonylmethyl)-cyclohexanecarboxamide;
trans-N-cyanomethyl-2-[4-(4-pyridin-4-yloxyphenyl)benzenesulfonylmethyl]-cyclohexanecarboxamide;
trans-N-cyanomethyl-2-[4-(3-aminophenyl)benzenesulfonylmethyl]-cyclohexanecarboxamide;
trans-N-cyanomethyl-2-[4-(pyridin-4-ylsulfanyl)benzenesulfonylmethyl]-cyclohexanecarboxamide;
trans-N-cyanomethyl-2-[4-(2-phenylethylsulfinyl)benzenesulfonylmethyl]-cyclohexanecarboxamide;

trans-N-cyanomethyl-2-[4-(2-phenylethylsulfanyl)benzenesulfonylmethyl]-cyclohexanecarboxamide;

trans-N-cyanomethyl-2-[4-(2-aminoethylsulfanyl)benzenesulfonylmethyl]-cyclohexanecarboxamide;

trans-N-cyanomethyl-2-[4-(2-chlorophenylmethylsulfanyl)benzenesulfonylmethyl]-cyclohexanecarboxamide;

trans-N-cyanomethyl-2-[4-(2-tert-butoxycarbonylaminoethylsulfanyl)benzenesulfonylmethyl]cyclohexanecarboxamide;

trans-N-cyanomethyl-2-[4-(2-(2,2,2-trifluoroethylamino)ethylsulfanyl)benzenesulfonyl-methyl]-cyclohexanecarboxamide;

trans-N-cyanomethyl-2-[4-(pyridin-3-ylmethylaminocarbonylmethylsulfanyl)benzene-sulfonylmethyl]-cyclohexanecarboxamide;

trans-N-cyanomethyl-2-[4-(2-(2-chloropyridin-3-ylcarbonylamino)ethylsulfanyl)-benzenesulfonylmethyl]-cyclohexanecarboxamide;

trans-N-cyanomethyl-2-[4-(2-pyridin-4-ylcarbonylaminoethylsulfanyl)benzenesulfonylmethyl]cyclohexanecarboxamide;

trans-N-cyanomethyl-2-[4-(2-acetylaminoethyloxy)benzenesulfonylmethyl]-cyclohexanecarboxamide;

trans-N-cyanomethyl-2-[4-(4-dimethylaminophenylmethylaminocarbonylmethylsulfanyl)benzenesulfonylmethyl]-cyclohexanecarboxamide;

trans-N-cyanomethyl-2-[3-fluoro-4-(2-aminoethylsulfanyl)benzenesulfonylmethyl]-cyclohexanecarboxamide;

trans-N-cyanomethyl-2-[4-(pyridin-4-ylmethylaminocarbonylmethylsulfanyl)benzene-sulfonylmethyl]-cyclohexanecarboxamide;

trans-N-cyanomethyl-2-[4-(2-thien-2-ylethylaminocarbonylmethylsulfanyl)-benzenesulfonylmethyl]-cyclohexanecarboxamide;

trans-N-cyanomethyl-2-[4-(2-pyridin-4-ylethylaminocarbonylmethylsulfanyl)benzenesulfonylmethyl]-cyclohexanecarboxamide;

trans-N-cyanomethyl-2-[3-fluoro-4-(2-ethylsulfonylaminoethylsulfanyl)-benzenesulfonylmethyl]-cyclohexanecarboxamide;

trans-N-cyanomethyl-2-[4-(2-chlorophenylmethylaminocarbonylmethylsulfanyl)-benzenesulfonylmethyl]-cyclohexanecarboxamide;

trans-N-cyanomethyl-2-[4-(4-methoxybenzylaminocarbonylmethylsulfanyl)-benzenesulfonylmethyl]-cyclohexanecarboxamide;

trans-N-cyanomethyl-2-[4-(furan-2-ylmethylaminocarbonylmethylsulfanyl)-benzenesulfonylmethyl]-cyclohexanecarboxamide;

trans-N-cyanomethyl-2-[4-(4-chlorophenylmethylaminocarbonylmethylsulfanyl)-benzenesulfonylmethyl]-cyclohexanecarboxamide;

trans-N-cyanomethyl-2-[3-fluoro-4-(2-dimethylsulfonylaminoethylsulfanyl)-benzenesulfonylmethyl]-cyclohexanecarboxamide;

trans-N-cyanomethyl-2-[4-(2-methylsulfonyloxyethylsulfanyl)-benzenesulfonylmethyl]-cyclohexanecarboxamide;

trans-N-cyanomethyl-2-[4-(3-dimethylaminobenzylaminocarbonylmethylsulfanyl)benzenesulfonylmethyl]cyclohexanecarboxamide;

trans-N-cyanomethyl-2-[4-(4-pyridin-4-ylpiperazin-1-ylcarbonylmethylsulfanyl)-benzenesulfonylmethyl]cyclohexanecarboxamide;

trans-N-cyanomethyl-2-(4-methoxycarbonylmethyloxybenzenesulfonylmethyl)-cyclohexanecarboxamide;

trans-N-cyanomethyl-2-[4-(1-ethyloxycarbonylethylsulfanyl)-benzenesulfonylmethyl]-cyclohexanecarboxamide;

trans-N-cyanomethyl-2-[4-(1-tert-butylpiperazin-4-ylcarbonylmethylsulfanyl)-benzenesulfonylmethyl]-cyclohexanecarboxamide;

trans-N-cyanomethyl-2-[4-(1-pyridin-2-ylpiperazin-4-ylcarbonylmethylsulfanyl)-benzenesulfonylmethyl]-cyclohexanecarboxamide;

trans-N-cyanomethyl-2-[4-(1-tert-butylpiperazin-4-ylcarbonylmethyloxy)-benzenesulfonylmethyl]-cyclohexanecarboxamide;

trans-N-cyanomethyl-2-[4-(1-pyrimidin-2-ylpiperazin-4-ylcarbonylmethylsulfanyl)-benzenesulfonylmethyl]-cyclohexanecarboxamide;

trans-N-cyanomethyl-2-[4-(2-thien-2-ylethylaminocarbonylmethylsulfonyl)-benzenesulfonylmethyl]-cyclohexanecarboxamide;

trans-N-cyanomethyl-2-{4-[1-(4-bromophenyl)piperazin-4-ylcarbonylmethylsulfanyl]-benzenesulfonylmethyl}-cyclohexanecarboxamide;

trans-N-cyanomethyl-2-[4-(2-pyridin-4-ylethylaminocarbonylmethyloxy)-benzenesulfonylmethyl]-cyclohexanecarboxamide;

trans-N-cyanomethyl-2-[4-(3-methyl-1,2,5-oxadiazol-4-ylmethylaminocarbonylmethyl-sulfanyl)-benzenesulfonylmethyl]-cyclohexanecarboxamide;

trans-N-cyanomethyl-2-[4-(2-morpholin-4-ylcarbonylaminoethylsulfanyl)-benzenesulfonylmethyl]-cyclohexanecarboxamide;

trans-N-cyanomethyl-2-[4-(pyridin-3-yloxyethylsulfanyl)-benzenesulfonylmethyl]-cyclohexanecarboxamide;

trans-N-cyanomethyl-2-[4-(2-morpholin-4-ylcarbonylaminoethyloxy)-benzenesulfonyl-methyl]-cyclohexanecarboxamide;

trans-N-cyanomethyl-2-[4-(1-benzylpiperidin-4-ylaminocarbonylmethylsulfanyl)-benzenesulfonylmethyl]-cyclohexanecarboxamide;

trans-N-cyanomethyl-2-[4-(furan-2-ylmethylaminocarbonylmethyl)-benzenesulfonylmethyl]-cyclohexanecarboxamide;

trans-N-cyanomethyl-2-[4-(2-furan-2-ylmethylaminocarbonylethyl)-benzenesulfonylmethyl]-cyclohexanecarboxamide;

trans-N-cyanomethyl-2-[4-(2-furan-2-ylmethylaminocarbonylethyl)-phenylsulfanylmethyl]-cyclohexanecarboxamide;

trans-N-cyanomethyl-2-[4-(benzylsulfanylmethyl)-benzenesulfonylmethyl]-cyclohexanecarboxamide;

trans-N-cyanomethyl-2-[4-(2-bromoethylsulfanyl)-benzenesulfonylmethyl]-cyclohexanecarboxamide;

trans-2-(4-fluorophenylsulfanylmethyl)-4-methylcyclopentanecarboxylic acid cyanomethylamide;

trans-N-cyanomethyl-2-(4-fluorophenylsulfanylmethyl)-5-methylcyclohexanecarboxamide;

cis-N-cyanomethyl-2-(4-methylsulfanylbenzenesulfonylmethyl)-cyclohexanecarboxamide;

trans-N-cyanomethyl-2-[1-(4-methylsulfanylbenzenesulfonyl)ethyl]-cyclohexanecarboxamide;

trans-N-cyanomethyl-2-{4-[3-(2-morpholin-4-ylethylaminocarbonyl)propyl]-phenylsulfanylmethyl}cyclohexanecarboxamide;

(R,R)-N-cyanomethyl-2-(4-methylsulfanylbenzenesulfonylmethyl)cyclohexanecarboxamide;

trans-N-cyanomethyl-2-[4-(2-morpholin-4-ylethylaminocarbonylmethylsulfanyl)-benzenesulfonylmethyl]cyclohexanecarboxamide;

trans-N-cyanomethyl-2-[4-(2-pyridin-2-ylethylsulfanyl)benzenesulfonylmethyl]-cyclohexanecarboxamide;

(1R/S,2R/S,5R/S)trans-N-cyanomethyl-2-(4-methylsulfanylbenzenesulfonylmethyl)-5-methylcyclohexane-carboxamide;

trans-N-cyanomethyl-2-(4-methylsulfanylbenzenesulfonylmethyl)-cyclohexanecarboxamide;

trans-N-cyanomethyl-2-[3-fluoro-4-(2-pyridin-2-ylethylsulfanyl)benzenesulfonylmethyl]cyclohexanecarboxamide;

trans-N-cyanomethyl-2-[4-(piperidin-3-ylaminocarbonylmethylsulfanyl)benzenesulfonylmethyl]cyclohexanecarboxamide;

trans-2-[4-(pyridin-2-ylethylsulfanyl)benzenesulfonylmethyl]cyclohexanecarboxylic acid (1-cyanocyclopropyl)amide;

trans-N-cyanomethyl-2-[4-(4-isopropylpiperazin-1-ylcarbonylmethylsulfanyl)benzene-sulfonylmethyl]cyclohexanecarboxamide;

trans-N-cyanomethyl-2-[4-(furan-2-ylmethylsulfanyl)benzenesulfonylmethyl]-cyclohexanecarboxamide;

trans-N-cyanomethyl-2-(3-hydroxypropylsulfanylbenzenesulfonylmethyl)-cyclohexanecarboxamide;

trans-N-cyanomethyl-2-[4-(4-thiolphenylsulfanyl)phenylsulfanylmethyl)-cyclohexanecarboxamide;

trans-2-{[(4-chlorophenyl)sulfanyl]methyl}-N-(cyanomethyl)cyclopentanecarboxamide;

trans-N-(cyanomethyl)-2-{[(4-fluorophenyl)sulfanyl]methyl}cyclopentanecarboxamide;

trans-2-{[(3-bromophenyl)sulfanyl]methyl}-N-(cyanomethyl)cyclohexanecarboxamide;

trans-N-(cyanomethyl)-2-{[(3-fluorophenyl)sulfanyl]methyl}cyclohexanecarboxamide;

trans-2-{[(3-aminophenyl)sulfanyl]methyl}-N-(cyanomethyl)cyclohexanecarboxamide;

trans-N-(cyanomethyl)-2-({[3-(trifluoromethyl)phenyl]sulfanyl}methyl)-cyclohexanecarboxamide;

3-{[(trans-2-{[(cyanomethyl)amino]carbonyl}cyclohexyl)methyl]sulfanyl}benzoic acid;

4-{[(trans-2-{[(cyanomethyl)amino]carbonyl}cyclohexyl)methyl]sulfanyl}benzoic acid;

trans-N-(cyanomethyl)-2-{[(3-hydroxyphenyl)sulfanyl]methyl}cyclohexanecarboxamide;

trans-N-(cyanomethyl)-2-({[3-(formylamino)phenyl]sulfanyl}methyl)-cyclohexanecarboxamide;

trans-2-({[3-(acetylamino)phenyl]sulfanyl}methyl)-N-(cyanomethyl)cyclohexanecarboxamide;

trans-2-[({3-[bis(methylsulfonyl)amino]phenyl}sulfanyl)methyl]-N-(cyanomethyl)-cyclohexanecarboxamide;

trans-N-(cyanomethyl)-2-{[(4-iodophenyl)sulfanyl]methyl}cyclopentanecarboxamide;

trans-N-(cyanomethyl)-2-{[4-iodobenzenesulfonyl]methyl}cyclopentanecarboxamide;

trans-N-(cyanomethyl)-2-{4-fluorobenzenesulfonylmethyl}cyclopentanecarboxamide;

trans-N-(cyanomethyl)-2-({4-methylsulfanylbenzenesulfonyl}methyl)-cyclopentanecarboxamide;

trans-N-(cyanomethyl)-2-{[(4-iodophenyl)sulfanyl]methyl}cyclohexanecarboxamide;

trans-N-(cyanomethyl)-2-{4-iodobenzenesulfonylmethyl}cyclohexanecarboxamide;

trans-N-(cyanomethyl)-2-[({4-[(2,2,2-trifluoroethyl)sulfanyl]benzene}sulfonyl)methyl]-cyclohexanecarboxamide;

trans-N-(cyanomethyl)-2-[({4-[(difluoromethyl)sulfanyl]phenyl}sulfanyl)methyl]-cyclohexanecarboxamide;

trans-N-(cyanomethyl)-2-[({4-[(difluoromethyl)sulfanyl]benzene}sulfonyl)methyl]-cyclohexanecarboxamide;

N-(cyanomethyl)-2-{4-fluorobenzenesulfonylmethyl}-4-methylcyclopentane-carboxamide;

N-(cyanomethyl)-4-methyl-2-({4-methylsulfanylbenzenesulfonyl}methyl)-cyclopentane-carboxamide;

N-(cyanomethyl)-2-{4-fluorobenzenesulfonylmethyl}-5-methylcyclohexane-carboxamide;

trans-N-(cyanomethyl)-2-({4-difluoromethoxybenzenesulfonyl}methyl)cyclohexane-carboxamide;

trans-N-(cyanomethyl)-2-{[4-(methylsulfanyl)phenoxy]methyl}cyclohexanecarboxamide;

trans-N-(cyanomethyl)-2-(1-{4-methylsulfanylbenzenesulfonyl}ethyl)cyclohexanecarboxamide;

trans-2-(4-methoxybenzylsulfonylmethyl)-cyclohexanecarboxylic acid cyanomethyl-amide;

trans-N-cyanomethyl-2-(4-carboxymethylsulfanylbenzenesulfonylmethyl)cyclohexane-carboxamide;

trans-N-(cyanomethyl)-2-({[4-(methylsulfanyl)phenyl]sulfanyl}-methyl)cyclopentane-carboxamide;

(1R,2R)-N-(cyanomethyl)-2-({[4-(methylsulfanyl)benzene]sulfonyl}methyl)-cyclohexanecarboxamide;

trans-N-cyanomethyl-2-(4-hydroxymethylbenzenesulfonylmethyl)-cyclohexanecarboxamide; and trans-N-cyanomethyl-2-(4-benzylsulfonylmethylbenzenesulfonylmethyl)-cyclohexanecarboxamide;

trans-N-cyanomethyl-2-[4-(2-morpholin-4-ylethyloxy)phenylsulfanylmethyl]-cyclohexanecarboxamide;

a pharmaceutically acceptable salt thereof.

15. A pharmaceutical composition comprising a therapeutically effective amount of a compound of claim 1 in combination with a pharmaceutically acceptable excipient.

16. A pharmaceutical composition comprising a therapeutically effective amount of a compound of claim 14 in combination with a pharmaceutically acceptable excipient.

17. A method of treating osteoporosis, which method comprises administering to a human a pharmaceutical composition comprising a therapeutically effective amount of compound of claim 1 in combination with a pharmaceutically acceptable excipient.

* * * * *